United States Patent [19]
Ishiguro et al.

[11] Patent Number: 5,959,107
[45] Date of Patent: Sep. 28, 1999

[54] ISOQUINOLINE DERIVATIVES

[75] Inventors: Susumu Ishiguro, Omiya; Shinichi Shimada, Tochigi-ken; Motohide Seya, Utsunomiya; Masayuki Okue, Tochigi-ken; Yuzo Yagi, Utsunomiya; Nobuo Ogane; Yasunari Saitou, both of Tochigi-ken, all of Japan

[73] Assignee: Snow Brand Milk Products Co., Ltd., Hokkaido, Japan

[21] Appl. No.: 09/051,404

[22] PCT Filed: Aug. 7, 1997

[86] PCT No.: PCT/JP97/02765

§ 371 Date: May 28, 1998

§ 102(e) Date: May 28, 1998

[87] PCT Pub. No.: WO98/05648

PCT Pub. Date: Dec. 2, 1998

[30] Foreign Application Priority Data

Aug. 7, 1996 [JP] Japan ..................................... 8-223271
Jul. 18, 1997 [JP] Japan ..................................... 9-208425

[51] Int. Cl.$^6$ ..................... C07D 401/00; C07D 241/36; C07D 219/00; C07D 215/38
[52] U.S. Cl. ......................... 544/284; 544/353; 546/102; 546/118; 546/171; 546/172; 546/178
[58] Field of Search ..................................... 546/172, 171, 546/178, 118, 102; 544/284, 353

[56] References Cited

PUBLICATIONS

Chemical Abstracts 121:187302, Ikegaki, 1994.
Chemical Abstracts 120:144163, Desantis, 1993.
Chemical Abstracts 119:49246, Peglion, 1993.
Chemical Abstracts 118:100528, Kajiwara, 1992.
Chemical Abstracts 117:226338, Berliner, 1992.
Chemical Abstracts 116:120903, Buxbaum, 1991.

*Primary Examiner*—D. Margaret M. Mach
*Attorney, Agent, or Firm*—Browdy and Neimark

[57] ABSTRACT

New isoquinoline derivatives and pharmaceutically acceptable acid addition salts represented by the following general formula (I)

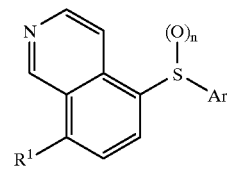

wherein Ar is an aromatic ring which may be substituted, and n shows 0, 1 or 2, have an inhibitory activity against apoptotic neuronal cell death. These compounds are useful for agents of prevention and treatment of neuronal neurodegenerative disorders such as Alzheimer's disease, Parkinson's disease, Huntington's chorea and amyotrophic lateral sclerosis, cerebral ischemic injury such as stroke, and peripheral neuropathy in diabetes mellitus.

9 Claims, 4 Drawing Sheets

Fig. 1

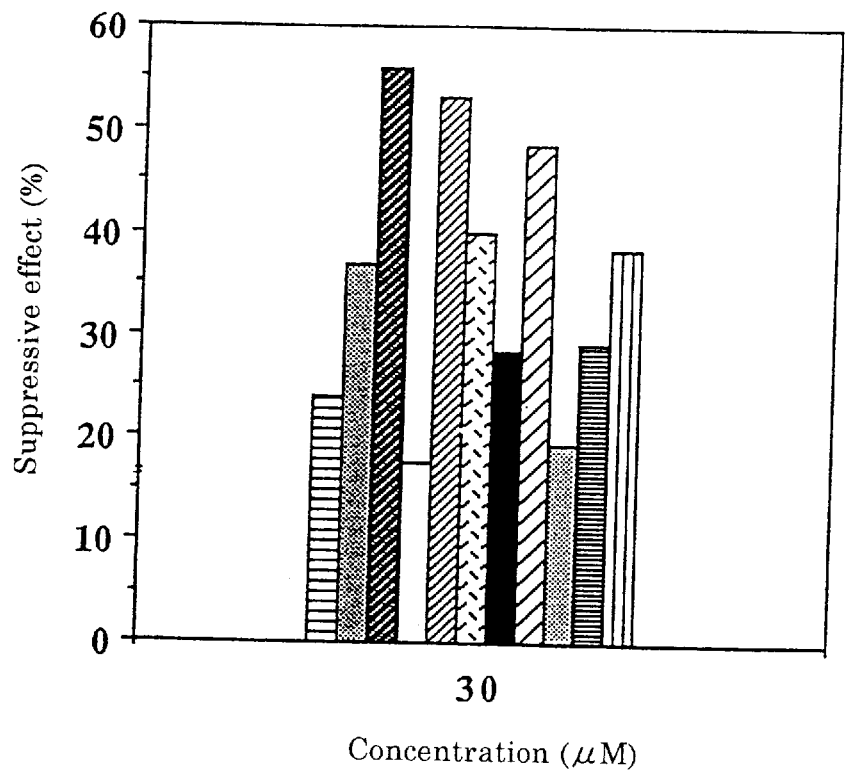

Concentration (μM)

- ☰ Example 3
  4-(5-Isoquinolylsulfonyl)aniline
- ▦ Example 48
  5(6)-(5-Isoquinolylsulfanyl)-2-methyl-1H-benzo[d]imidazole
- ▨ Example 52
  5(6)-(5-Isoquinolylsulfonyl)-2-methyl-6(5)-nitro-1H-benzo[d]imidazole
- ☐ Example 59
  5(6)-(5-Isoquinolylsulfonyl)-2-methyl-1H-benzo[d]imidazole-6(5)-carbonitrile
- ▨ Example 73
  2-Ethyl-5(6)-(5-isoquinolylsulfonyl)-6(5)-nitro-1H-benzo[d]imidazole
- ▨ Example 75
  6(5)-Chloro-2-ethyl-5(6)-(5-isoquinolylsulfonyl)-1H-benzo[d]imidazole
- ■ Example 99
  5-(5-Isoquinolylsulfonyl)-6-nitro-2,3-dihydro-1H-benzo[d]imidazol-2-one
- ▨ Example 108
  5(6)-(5-Isoquinolylsulfanyl)-4(7)-nitro-1H-benzo[d][1,2,3]triazole
- ▦ Example 127
  6(5)-Chloro-2-cyclobutyl-5(6)-(5-isoquinolylsulfonyl)-1H-benzo[d]imidazole
- ☰ Example 134
  6(5)-Bromo-5(6)-(5-isoquinolylsulfonyl)-2-methyl-1H-benzo[d]imidazole
- ⫼ Example 135
  6(5)-Bromo-2-ethyl-5(6)-(5-isoquinolylsulfonyl)-1H-benzo[d]imidazole

Fig. 2

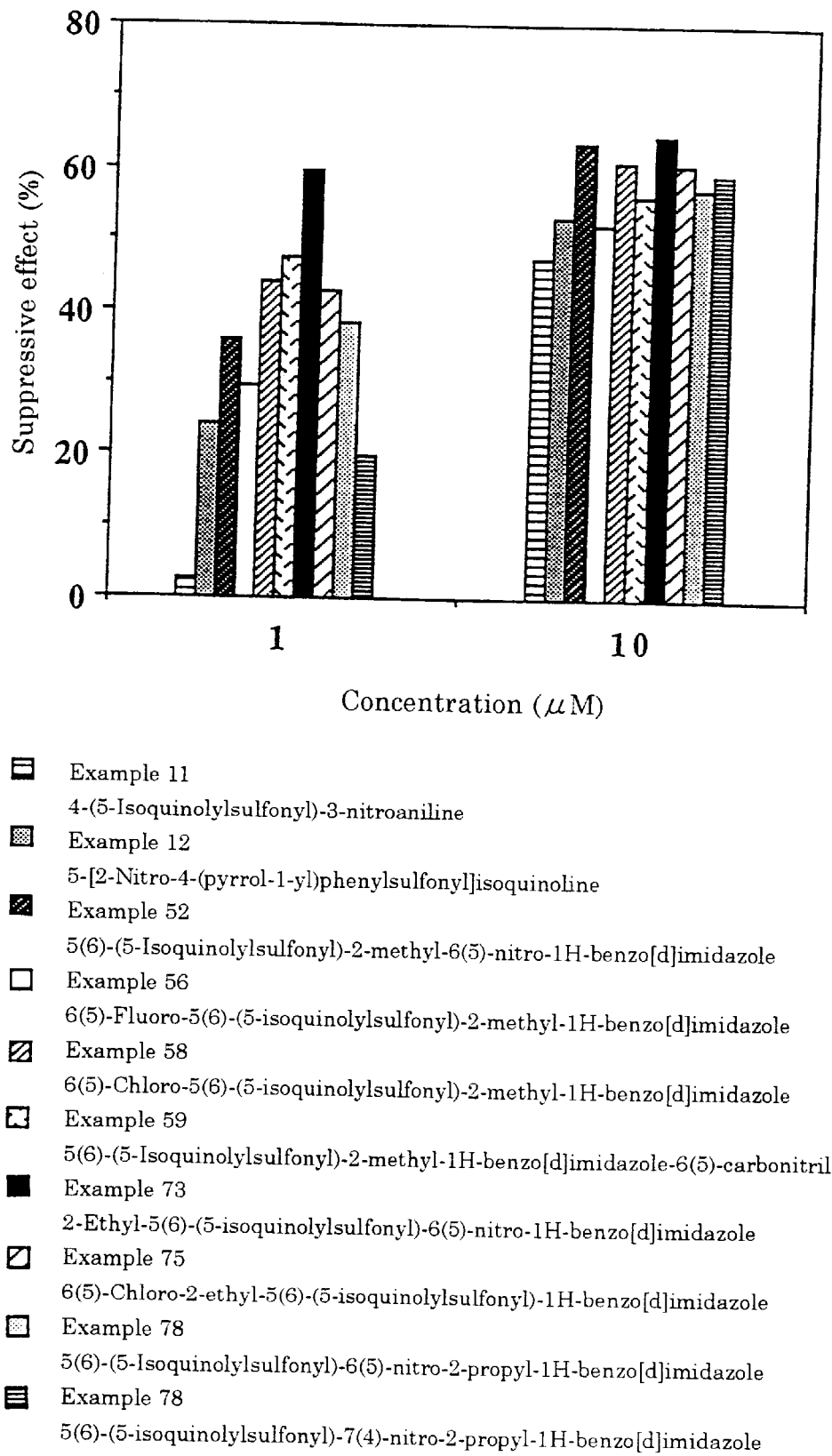

- Example 11
  4-(5-Isoquinolylsulfonyl)-3-nitroaniline
- Example 12
  5-[2-Nitro-4-(pyrrol-1-yl)phenylsulfonyl]isoquinoline
- Example 52
  5(6)-(5-Isoquinolylsulfonyl)-2-methyl-6(5)-nitro-1H-benzo[d]imidazole
- Example 56
  6(5)-Fluoro-5(6)-(5-isoquinolylsulfonyl)-2-methyl-1H-benzo[d]imidazole
- Example 58
  6(5)-Chloro-5(6)-(5-isoquinolylsulfonyl)-2-methyl-1H-benzo[d]imidazole
- Example 59
  5(6)-(5-Isoquinolylsulfonyl)-2-methyl-1H-benzo[d]imidazole-6(5)-carbonitrile
- Example 73
  2-Ethyl-5(6)-(5-isoquinolylsulfonyl)-6(5)-nitro-1H-benzo[d]imidazole
- Example 75
  6(5)-Chloro-2-ethyl-5(6)-(5-isoquinolylsulfonyl)-1H-benzo[d]imidazole
- Example 78
  5(6)-(5-Isoquinolylsulfonyl)-6(5)-nitro-2-propyl-1H-benzo[d]imidazole
- Example 78
  5(6)-(5-isoquinolylsulfonyl)-7(4)-nitro-2-propyl-1H-benzo[d]imidazole

Fig. 3

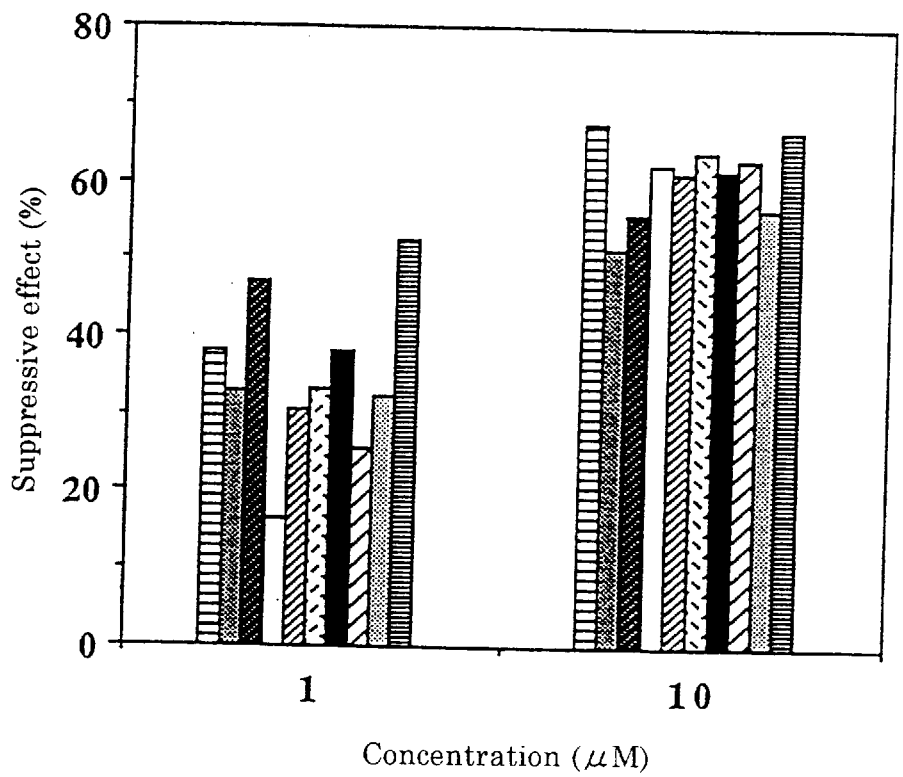

Concentration ($\mu$M)

- Example 80  
  6(5)-Chloro-5(6)-(5-isoquinolylsulfonyl)-2-propyl-1H-benzo[d]imidazole
- Example 82  
  2-Isopropyl-5(6)-(5-isoquinolylsulfonyl)-1H-benzo[d]imidazole
- Example 83  
  2-Isopropyl-5(6)-(5-isoquinolylsulfonyl)-6(5)-nitro-1H-benzo[d]imidazole
- Example 88  
  6(5)-Chloro-5(6)-(5-isoquinolylsulfonyl)-2-phenyl-1H-benzo[d]imidazole
- Example 94  
  2-Cyclobutyl-5(6)-(5-isoquinolylsulfonyl)-1H-benzo[d]imidazole
- Example 95  
  2-Cyclopentyl-5(6)-(5-isoquinolylsulfonyl)-1H-benzo[d]imidazole
- Example 96  
  2-Cyclohexyl-5(6)-(5-isoquinolylsulfonyl)-1H-benzo[d]imidazole
- Example 97  
  2-Cycloheptyl-5(6)-(5-isoquinolylsulfonyl)-1H-benzo[d]imidazole
- Example 114  
  2,3-Diphenyl-6-(5-isoquinolylsulfonyl)quinoxaline
- Example 123  
  2-Cyclohexyl-5(6)-(5-isoquinolylsulfonyl)-6(5)-nitro-1H-benzo[d]imidazole

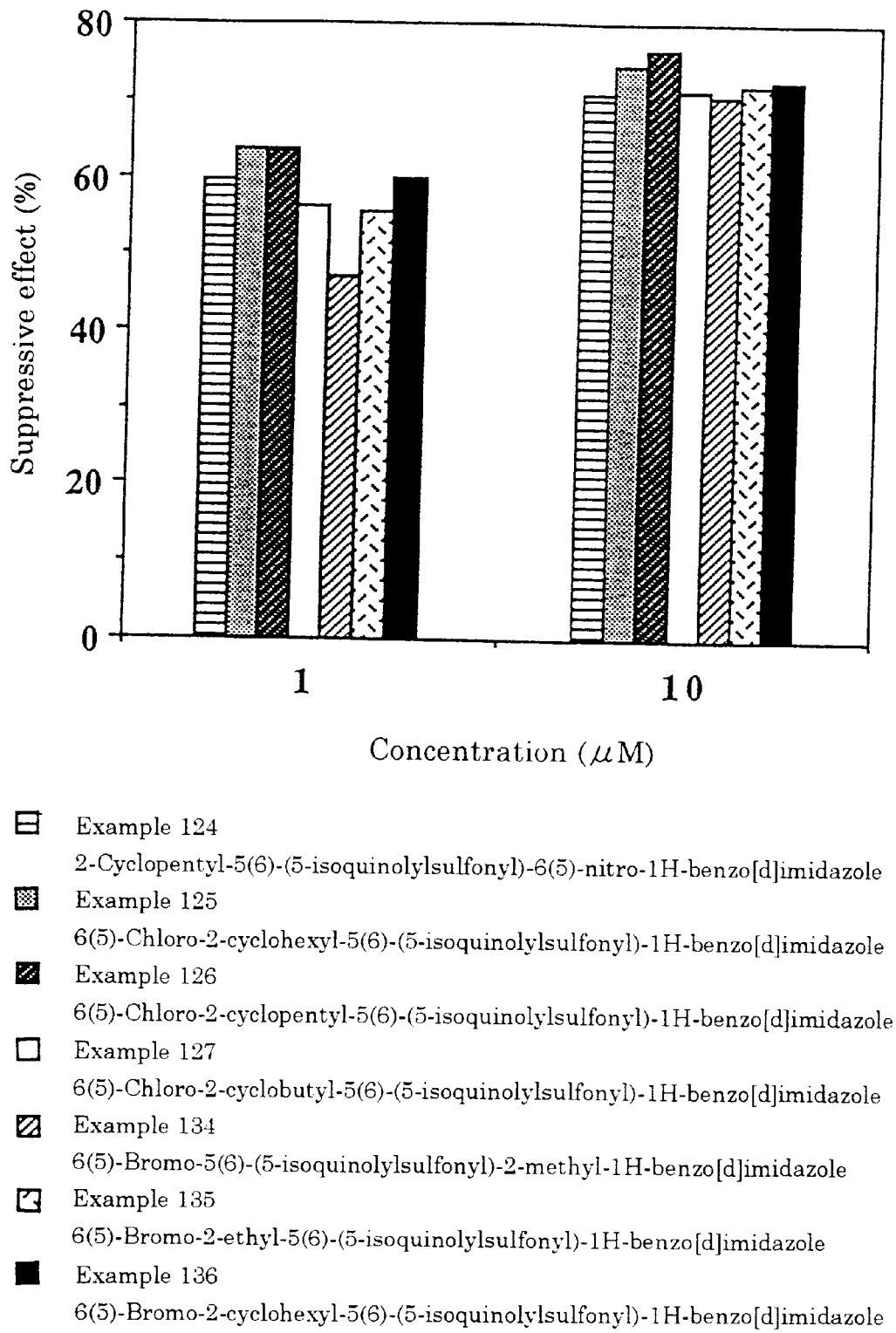

Fig. 4

☱ Example 124
2-Cyclopentyl-5(6)-(5-isoquinolylsulfonyl)-6(5)-nitro-1H-benzo[d]imidazole ▦ Example 125
6(5)-Chloro-2-cyclohexyl-5(6)-(5-isoquinolylsulfonyl)-1H-benzo[d]imidazole ▨ Example 126
6(5)-Chloro-2-cyclopentyl-5(6)-(5-isoquinolylsulfonyl)-1H-benzo[d]imidazole ☐ Example 127
6(5)-Chloro-2-cyclobutyl-5(6)-(5-isoquinolylsulfonyl)-1H-benzo[d]imidazole ▨ Example 134
6(5)-Bromo-5(6)-(5-isoquinolylsulfonyl)-2-methyl-1H-benzo[d]imidazole ▨ Example 135
6(5)-Bromo-2-ethyl-5(6)-(5-isoquinolylsulfonyl)-1H-benzo[d]imidazole ■ Example 136
6(5)-Bromo-2-cyclohexyl-5(6)-(5-isoquinolylsulfonyl)-1H-benzo[d]imidazole

ISOQUINOLINE DERIVATIVES

TECHNICAL FIELD

The present invention relates to new isoquinoline derivatives and their pharmaceutically acceptable acid addition salts. The derivatives of the present invention have inhibitory activity on neuronal cell death (apoptotic cell death-type) caused by excessive apoptosis in a nervous system and they are useful for prevention or treatment of neurodegenerative disorders such as Alzheimer's disease, Parkinson's disease, Huntington's chorea and amyotrophic lateral sclerosis, cerebral ischemic injury such as stroke, and peripheral neuropathy in diabets mellitus.

BACKGROUND ART

Cell death is classified from morphological change into necrosis that whole cells are swelled by cell membrane degeneration and die out, and apoptosis that whole cells reduce the sizes to change the nuclear structure and to fragmentize DNA into ladders and die out (Kerr and Harrnon, Apoptosis: The molecular Basis of Cell Death, Tomei and Cope (Eds), pp5–29 (1991), Cold Spring Harbor Laboratory Press). It has become clear that the apoptosis is greatly involved in pathology suffering from many diseases, and there is possibility of new treatment by controlling inappropriate apoptosis (Thompson, Science, Vol. 267, pp 1456–1462 (1995)).

Several lines of evidence suggest that neuronal cell death in neuro degenerative disorders occurs by apoptosis (Alzheimer disease, Parkinson disease, Huntington chorea, amyotrophic lateral sclerosis and the like) (Su et al., Neuro Report, Vol. 5, pp 2529–2533 (1994); Yoshiyama et al., Acta Neuropathologica, Vol. 88, pp 207–211 (1994); Lassman et al., Acta Neuropathologica, Vol. 89, pp 35–41 (1995); Smale et al., Experimental Neurology, Vol. 133, pp 225–230 (1995); Dragunow et al., Neuro Report, Vol. 6, pp 1053–1057 (1995); Portera-Cailliau et al., Journal of Neuroscience, Vol. 15, pp 3775–3787 (1995); Cotman and Anderson, Molecular Neurobiology, Vol. 10, pp 19–45 (1995); Bredesen, Annals of Neurology, Vol. 38, pp 839–851 (1995)). In addition, apoptosis has been suggested to play a role in delayed neuronal death of Mongolian gerbil following transitant ischemia (Nitatori et al., Journal of Neuroscience, Vol. 15, pp 1001–1011 (1995)). As some agents for inhibiting neuronal apoptotic cell death, protein and RNA synthesis inhibitors can be exemplified. However, specificity of these inhibitors for advanced drug development is questionable. Further, a product of Bcl-2 gene and a protein factor such as a neurotropic factor have problems because these are not safely and effectively administered in vivo, so that these are not practically used. Therefore, therapeutic method for the control of neuronal cell death in neurodegenerative disorders has not been established. Hitherto, many isoquinoline derivatives are known, especially, a compound binding an alkyl group via an sulfur atom at a 5-position of isoquinoline (Euerby, Mervin R. and Waigh, Roger D., J. Chem. Soc. Chem. Commun., Vol. 2, 127–128 (1984)). However, a compound binding an aromatic ring via a sulfur atom at a 5-position of isoquinoline has not been known.

DISCLOSURE OF INVENTION

In view of the above-mentioned conditions, the present inventors have been earnestly studied and found new compounds having excellent effects for suppression of the neuronal cell death caused by excess apoptosis in a nervous system. Accordingly, the present invention aims to provide new isoquinoline derivatives having inhibition activity for the nervous cell death caused by apoptosis acceleration in a nervous system.

The present invention relates to new isoquinoline derivatives and their pharmaceutically acceptable acid addition salts there of.

The new isoquinoline derivatives and their pharmaceutically acceptable acid addition salts there of are represented by the following general formula (I).

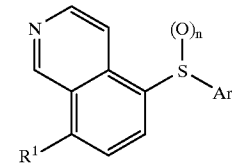

wherein Ar shows an aromatic ring or a heterocycle, n shows 0, 1 or 2, and $R^1$ shows a substituted group selected from hydrogen, nitro and amino.

Preferably, Ar of the above isoquinoline derivatives is selected from following aromatic ring:

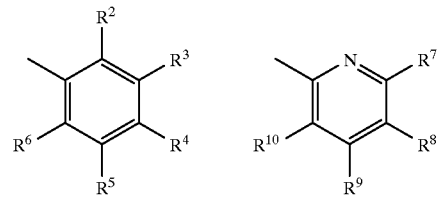

wherein $R^2$–$R^{10}$ show the same or different substituted groups selected from the group of hydrogen, nitro, amino, lower alkyl amide, aryl amide, lower alkyl amino, aryl amino, aralkyl amino, carbamoyl, hydroxy, cyano, lower alkyl substituted by halogen, aryl sulfonyl, aryl sulfonamide, imidazol, tetrazole, pyrrole, and halogen atom.

Preferably, Ar of the above isoquinoline derivatives is selected from any bicyclic compound which may be substituted by the following groups:

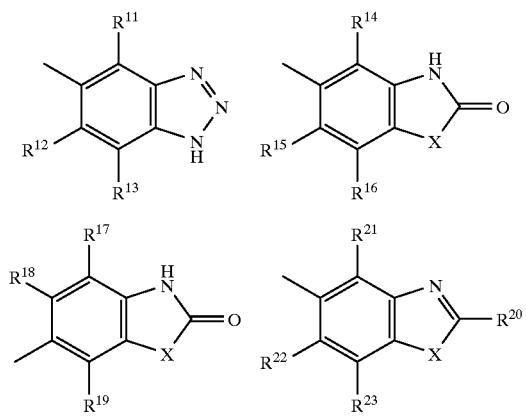

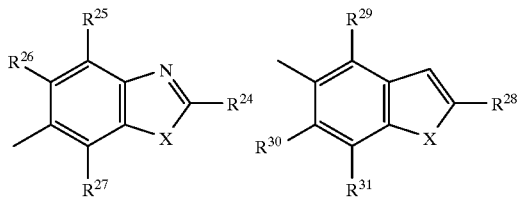

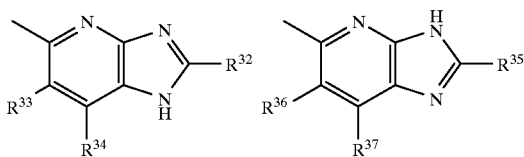

wherein X shows NH, O or S, $R^{11}$–$R^{37}$ show the same or different substituted groups selected from the group of hydrogen, lower alkyl, lower alkyl substituted by halogen, aryl, aralkyl, nitro, amino, cyano and halogen.

More preferably, Ar of the above isoquinoline derivatives is selected from following benzimidazole group:

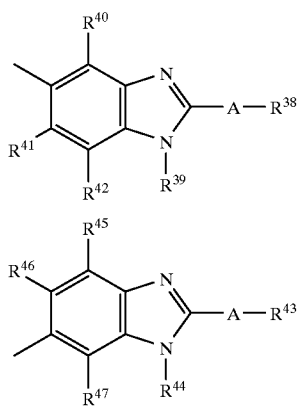

wherein $R^{38}$–$R^{47}$ show the same or different substituted groups selected from the group of hydrogen, lower alkyl, cycloalkyl, lower alkyl substituted by halogen, aryl, aralkyl, nitro, —$NR^{48}R^{49}$, —$NHCO_2R^{50}$, hydroxy, cyano and halogen, A shows a substituted group selected from bonding or lower alkylene, and $R^{48}$–$R^{50}$ show the same or different substituted groups selected from hydrogen or lower alkyl.

In addition, preferably, Ar of the above isoquinoline derivatives is selected from any polycyclic compound which may be substituted by the following groups:

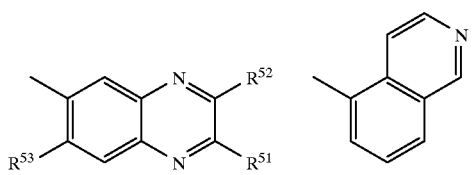

wherein $R^{51}$–$^{59}$ show the same or different substituted groups select from the group of hydrogen, lower alkyl, lower alkyl substituted by halogen, aryl, aralkyl, nitro, amino, cyano and halogen.

As embodiments of the isoquinoline derivatives of the present invention, the following compounds are exemplified:

(1) 5-(4-nitrophenylsulfanyl)isoquinoline
(2) 5-(4-nitrophenylsulfonyl)isoquinoline
(3) 4-(5-isoquinolylsulfonyl)aniline
(4) N1-[4-(5-isoquinolylsulfonyl)phenyl]acetamide
(5) 5-[4-(pyrrole-1-yl)phenylsulfonyl]isoquinoline
(6) 5-(5-isoquinolylsulfanyl)-2-nitroaniline
(7) 5-(5-isoquinolylsulfonyl)-2-nitroaniline
(8) 4-(5-isoquinolylsulfanyl)-1,2-benzenediamine
(9) 4-(5-isoquinolylsulfonyl)-1,2-benzenediamine
(10) 4-(5-isoquinolylsulfanyl)-3-nitroaniline
(11) 4-(5-isoquinolylsulfonyl)-3-nitroaniline
(12) 5-[2-nitro-4-(pyrrol-1-yl)phenylsulfonyl]isoquinoline
(13) 4-(5-isoquinolylsulfanyl)-3-nitrobenzonitrile
(14) 5-[2-nitro-4-(1(2)H-1,2,3,4-tetrazol-5-yl)phenylsulfanyl]isoquinoline
(15) 5-[2-nitro-4-(1(2)H-1,2,3,4-tetrazol-5-yl)phenylsulfonyl]isoquinoline
(16) 5-(5-isoquinolylsulfanyl)-2-nitrophenol
(17) 2-amino-5-(5-isoquinolylsulfanyl)phenol
(18) 2-amino-5-(5-isoquinolylsulfonyl)phenol
(19) 5-[3-hydroxy-4-(pyrrol-1-yl)phenylsulfonyl]isoquinoline
(20) 5-[2-fluoro-4-(1(2)H-1,2,3,4-tetrazol-5-yl)phenylsulfanyl]isoquinoline
(21) 5-[2-fluoro-4-(1(2)H-1,2,3,4-tetrazol-5-yl)phenylsulfonyl]isoquinoline

(22) 5-(2-chloro-4-nitrophenylsulfonyl)isoquinoline
(23) 3-chloro-4-(5-isoquinolylsulfonyl)aniline
(24) 5-[2-chloro-4-(pyrrol-1-yl)phenylsulfonyl]isoquinoline
(25) 3-chloro-4-(5-isoquinolylsulfanyl)benzonitrile
(26) 5-[2-chloro-4-(1(2)H-1,2,3,4-tetrazol-5-yl)phenylsulfanyl]isoquinoline
(27) 5-[2-chloro-4-(1(2)H-1,2,3,4-tetrazol-5-yl)phenylsulfonyl]isoquinoline
(28) 4-(5-isoquinolylsulfanyl)-5-nitro-1,2-benzenediamine
(29) 5-(5-isoquinolylsulfanyl)-2,4-dinitroaniline
(30) N1-[4-(5-isoquinolylsulfanyl)-2-methylcarboxamide-5-nitrophenyl]acetamide
(31) N1-[2-ethylcarboxamide-4-(5-isoquinolylsulfanyl)-5-nitrophenyl]propanamide
(32) N1-[2-amino-4-(5-isoquinolylsulfanyl)-5-nitrophenyl]butanamide
(33) N1-[2-amino-4-(5-isoquinolylsulfanyl)-5-nitrophenyl]-2-methylpropanamide
(34) 4-fluoro-5-(5-isoquinolylsulfanyl)-2-nitroaniline
(35) 4-fluoro-5-(5-isoquinolylsulfanyl)-1,2-benzenediamine
(36) 4-chloro-5-(5-isoquinolylsulfanyl)-2-nitroaniline
(37) 4-chloro-5-(5-isoquinolylsulfanyl)-1,2-benzenediamine
(38) 4-chloro-5-(5-isoquinolylsulfonyl)-2-nitroaniline
(39) 4-chloro-5-(5-isoquinolylsulfonyl)-1,2-benzenediamine
(40) 4-(5-isoquinolylsulfanyl)-5-methyl-2-nitroaniline
(41) 4-(5-isoquinolylsulfanyl)-5-methyl-1,2-benzenediamine
(42) 5(6)-(5-isoquinolylsulfanyl)-1H-benzo[d]imidazole
(43) 5(6)-(5-isoquinolylsulfonyl)-1H-benzo[d]imidazole
(44) 6(5)-chloro-5(6)-(5-isoquinolylsulfanyl)-1H-benzo[d]imidazole
(45) 6(5)-chloro-5(6)-(5-isoquinolylsulfonyl)-1H-benzo[d]imidazole
(46) 5(6)-(5-isoquinolylsulfanyl)-4(7)-nitro-1H-benzo[d]imidazole
(47) 5(6)-(5-isoquinolylsulfonyl)-4(7)-nitro-1H-benzo[d]imidazole
(48) 5(6)-(5-isoquinolylsulfanyl)-2-methyl-1H-benzo[d]imidazole
(49) 5(6)-(5-isoquinolylsulfonyl)-2-methyl-1H-benzo[d]imidazole
(50) 5(6)-(5-isoquinolylsulfanyl)-2-methyl-6(5)-nitro-1H-benzo[d]imidazole
(51) 5(6)-(5-isoquinolylsulfinyl)-2-methyl-6(5)-nitro-1H-benzo[d]imidazole
(52) 5(6)-(5-isoquinolylsulfonyl)-2-methyl-6(5)-nitro-1H-benzo[d]imidazole
(53) 5(6)-(5-isoquinolylsulfonyl)-2-methyl-7(4)-nitro-1H-benzo[d]imidazole
(54) 5(6)-(5-isoquinolylsulfonyl)-2-methyl-1H-benzo[d]imidazole-6(5)-amine
(55) 5(6)-(5-isoquinolylsulfonyl)-2-methyl-1H-benzo[d]imidazole-7(4)-amine
(56) 6(5)-fluoro-5(6)-(5-isoquinolylsulfanyl)-2-methyl-1H-benzo[d]imidazole
(57) 6(5)-fluoro-5(6)-(5-isoquinolylsulfonyl)-2-methyl-1H-benzo[d]imidazole
(58) 6(5)-chloro-5(6)-(5-isoquinolylsulfanyl)-2-methyl-1H-benzo[d]imidazole
(59) 6(5)-chloro-5(6)-(5-isoquinolylsulfonyl)-2-methyl-1H-benzo[d]imidazole
(60) 5(6)-(5-isoquinolylsulfonyl)-2-methyl-1H-benzo[d]imidazole-6(5)-carbonitrile
(61) 5(6)-(5-isoquinolylsulfanyl)-2,6(5)-dimethyl-1H-benzo[d]imidazole
(62) 5(6)-(5-isoquinolylsulfonyl)-2,6(5)-dimethyl-1H-benzo[d]imidazole
(63) 1-ethyl-6-(5-isoquinolylsulfanyl)-2-methyl-5-nitro-1H-benzo[d]imidazole
(64) 1-ethyl-6-(5-isoquinolylsulfonyl)-2-methyl-5-nitro-1H-benzo[d]imidazole
(65) 5-chloro-1-ethyl-6-(5-isoquinolylsulfonyl)-2-methyl-1H-benzo[d]imidazole
(66) 1-ethyl-5-(5-isoquinolylsulfanyl)-2-methyl-6-nitro-1H-benzo[d]imidazole
(67) 1-ethyl-5-(5-isoquinolylsulfonyl)-2-methyl-6-nitro-1H-benzo[d]imidazole
(68) N1-benzyl-5-(5-isoquinolylsulfanyl)-2-nitroaniline
(69) N2-benzyl-4-(5-isoquinolylsulfanyl)-1,2-benzenediamine
(70) 1-benzyl-6-(5-isoquinolylsulfanyl)-2-methyl-1H-benzo[d]imidazole
(71) 2-ethyl-5(6)-(5-isoquinolylsulfanyl)-1H-benzo[d]imidazole
(72) 2-ethyl-5(6)-(5-isoquinolylsulfonyl)-1H-benzo[d]imidazole
(73) 2-ethyl-5(6)-(5-isoquinolylsulfanyl)-6(5)-nitro-1H-benzo[d]imidazole
(74) 2-ethyl-5(6)-(5-isoquinolylsulfonyl)-6(5)-nitro-1H-benzo[d]imidazole
(75) 2-ethyl-5(6)-(5-isoquinolylsulfonyl)-7(4)-nitro-1H-benzo[d]imidazole
(76) 6(5)-chloro-2-ethyl-5(6)-(5-isoquinolylsulfanyl)-1H-benzo[d]imidazole
(77) 6(5)-chloro-2-ethyl-5(6)-(5-isoquinolylsulfonyl)-1H-benzo[d]imidazole
(78) 5(6)-(5-isoquinolylsulfanyl)-2-propyl-1H-benzo[d]imidazole
(79) 5(6)-(5-isoquinolylsulfonyl)-2-propyl-1H-benzo[d]imidazole
(80) 5(6)-(5-isoquinolylsulfonyl)-6(5)-nitro-2-propyl-1H-benzo[d]imidazole
(81) 5(6)-(5-isoquinolylsulfonyl)-7(4)-nitro-2-propyl-1H-benzo[d]imidazole
(82) 6(5)-chloro-5(6)-(5-isoquinolylsulfanyl)-2-propyl-1H-benzo[d]imidazole
(83) 6(5)-chloro-5(6)-(5-isoquinolylsulfonyl)-2-propyl-1H-benzo[d]imidazole
(84) 2-isopropyl-5(6)-(5-isoquinolylsulfanyl)-1H-benzo[d]imidazole
(85) 2-isopropyl-5(6)-(5-isoquinolylsulfonyl)-1H-benzo[d]imidazole
(86) 2-[5(6)-(5-isoquinolylsulfonyl)-1H-benzo[d]imidazole-2-yl]-2-propanol
(87) 2-isopropyl-5(6)-(5-isoquinolylsulfonyl)-6(5)-nitro-1H-benzo[d]imidazole
(88) 2-isopropyl-5(6)-(5-isoquinolylsulfonyl)-7(4)-nitro-1H-benzo[d]imidazole
(89) 4-(5-isoquinolylsulfanyl)-1,2-di(phenylcarboxamide)benzene
(90) 5(6)-(5-isoquinolylsulfanyl)-2-phenyl-1H-benzo[d]imidazole
(91) 4-chloro-5-(5-isoquinolylsulfanyl)-1,2-di(phenylcarboxamide)benzene
(92) 6(5)-chloro-5(6)-(5-isoquinolylsulfanyl)-2-phenyl-1H-benzo[d]imidazole
(93) 6(5)-chloro-5(6)-(5-isoquinolylsulfonyl)-2-phenyl-1H-benzo[d]imidazole
(94) 5(6)-(5-isoquinolylsulfanyl)-2-trifluoromethyl-1H-benzo[d]imidazole
(95) 5(6)-(5-isoquinolylsulfonyl)-2-trifluoromethyl-1H-benzo[d]imidazole

(96) 5(6)-(5-isoquinolylsulfonyl)-2-hexyl-1H-benzo[d]imidazole
(97) 2-cyclopropyl-5(6)-(5-isoquinolylsulfanyl)-1H-benzo[d]imidazole
(98) 2-cyclopropyl-5(6)-(5-isoquinolylsulfonyl)-1H-benzo[d]imidazole
(99) 2-cyclobutyl-5(6)-(5-isoquinolylsulfonyl)-1H-benzo[d]imidazole
(100) 2-cyclopentyl-5(6)-(5-isoquinolylsulfonyl)-1H-benzo[d]imidazole
(101) 2-cyclohexyl-5(6)-(5-isoquinolylsulfonyl)-1H-benzo[d]imidazole
(102) 2-cycloheptyl-5(6)-(5-isoquinolylsulfonyl)-1H-benzo[d]imidazole
(103) 5-(5-isoquinolylsulfonyl)-6-nitro-2,3-dihydro-1H-benzo[d]imidazol-2-one
(104) 5-(5-isoquinolylsulfonyl)-6-nitro-2,3-dihydro-1H-benzo[d]imidazol-2-one
(105) 5-(5-isoquinolylsulfanyl)-6-nitro-2,3-dihydro-benzo[d][1,3]thiazol-2-one
(106) 5-(5-isoquinolylsulfinyl)-6-nitro-2,3-dihydro-benzo[d][1,3]thiazol-2-one
(107) 5-(5-isoquinolylsulfanyl)-6-nitro-2,3-dihydro-benzo[d][1,3]oxazol-2-one
(108) 5-(5-isoquinolylsulfonyl)-6-nitro-2,3-dihydro-benzo[d][1,3]oxazol-2-one
(109) 6-(5-isoquinolylsulfanyl)-5-nitro-2,3-dihydro-benzo[d][1,3]oxazol-2-one
(110) 6-(5-isoquinolylsulfonyl)-5-nitro-2,3-dihydro-benzo[d][1,3]oxazol-2-one
(111) 6-(5-isoquinolylsulfanyl)-2-methylbenzo[d][1,3]oxazole
(112) 5-(5-isoquinolylsulfanyl)-2-methyl-6-nitrobenzo[d][1,3]thiazole
(113) 5(6)-(5-isoquinolylsulfanyl)-4(7)-nitro-1H-benzo[d][1,2,3]triazole
(114) 5(6)-(5-isoquinolylsulfonyl)-4(7)-nitro-1H-benzo[d][1,2,3]triazole
(115) 6-(5-isoquinolylsulfanyl)quinoxaline
(116) 6-(5-isoquinolylsulfanyl)-7-nitroquinoxaline
(117) 6-(5-isoquinolylsulfonyl)quinoxaline
(118) 2,3-dimethyl-6-(5-isoquinolylsulfonyl)quinoxaline
(119) 2,3-diphenyl-6-(5-isoquinolylsulfonyl)quinoxaline
(120) 7-(5-isoquinolylsulfonyl)-1,2,3,4-tetrahydrophenazine
(121) 6-chloro-7-(5-isoquinolylsulfonyl)-2,3-dimethylquinoxaline
(122) 6-chloro-7-(5-isoquinolylsulfonyl)-2,3-diphenylquinoxaline
(123) 9-(5-isoquinolylsulfonyl)acenaphtho[1,2-b]quinoxaline
(124) 9-chloro-10-(5-isoquinolylsulfonyl)acenaphtho[1,2-b]quinoxaline
(125) 11-(5-isoquinolylsulfonyl) dibenzo[a,c]phenazine
(126) 5-(5-isoquinolylsulfanyl)isoquinoline
(127) 5-(5-isoquinolylsulfonyl)isoquinoline
(128) 2-cyclohexyl-5(6)-(5-isoquinolylsulfonyl)-6(5)-nitro-1H-benzo[d]imidazole
(129) 2-cyclohexyl-5(6)-(5-isoquinolylsulfonyl)-7(4)-nitro-1H-benzo[d]imidazole
(130) 2-cyclopentyl-5(6)-(5-isoquinolylsulfonyl)-6(5)-nitro-1H-benzo[d]imidazole
(131) 2-cyclopentyl-5(6)-(5-isoquinolylsulfonyl)-7(4)-nitro-1H-benzo[d]imidazole
(132) 6(5)-chloro-2-cyclohexyl-5(6)-(5-isoquinolylsulfonyl)-1H-benzo[d]imidazole
(133) 6(5)-chloro-2-cyclopentyl-5(6)-(5-isoquinolylsulfonyl)-1H-benzo[d]imidazole
(134) 6(5)-chloro-2-cyclobutyl-5(6)-(5-isoquinolylsulfonyl)-1H-benzo[d]imidazole
(135) 5-(5-isoquinolylsulfanyl)-2-nitro-4-(trifluoromethyl)anilin
(136) 5-(5-isoquinolylsulfonyl)-2-nitro-4-(trifluoromethyl)anilin
(137) 4-(5-isoquinolylsulfonyl)-5-(trifluoromethyl)-1,2-benzenediamine
(138) 5(6)-(5-isoquinolylsulfonyl)-2-methyl-6(5)-(trifluoromethyl)-1H-benzo[d]imidazole
(139) 4-bromo-5-(5-isoquinolylsulfanyl)-2-nitroaniline
(140) 4-bromo-5-(5-isoquinolylsulfonyl)-1,2-benzenediamine
(141) 6(5)-bromo-5(6)-(5-isoquinolylsulfonyl)-2-methyl-1H-benzo[d]imidazole
(142) 6(5)-bromo-2-ethyl-5(6)-(5-isoquinolylsulfonyl)-1H-benzo[d]imidazole
(143) 6(5)-bromo-2-cyclohexyl-5(6)-(5-isoquinolylsulfonyl)-1H-benzo[d]imidazole
(144) diethyl{2-[5(6)-(5-isoquinolylsulfonyl)-1H-benzo[d]imidazole-2-yl]ethyl}amine
(145) diethyl{2-[5(6)-(5-isoquinolylsulfonyl)-6(5)-nitro-1H-benzo[d]imidazole-2-yl]ethyl}amine
(146) 6(5)-chloro-5(6)-(5-isoquinolylsulfonyl)-1H-benzo[d]imidazole-2-carbamic acid methyl ester
(147) 2-amino-4-(5-isoquinolylsulfanyl)-1-(4-methylphenyl)sulfonamide-5-nitrobenzene
(148) 3-fluoro-4-(5-isoquinolylsulfonyl)benzonitrile
(149) 3-chloro-4-(5-isoquinolylsulfonyl)benzonitrile
(150) 4-(5-isoquinolylsulfonyl)-3-nitrobenzamide
(151) 5-(5-chloro-2-nitrophenylsulfanyl)isoquinoline
(152) 5-[5-(1H-1-imidazolyl)-2-nitrophenylsulfanyl]isoquinoline
(153) 5-(5-chloro-2-nitrophenylsulfonyl)isoquinoline
(154) 5-[4-(1H-1-imidazolyl)-2-nitrophenylsulfanyl]isoquinoline
(155) 5-[4-(1H-1-imidazolyl)-2-nitrophenylsulfonyl]isoquinoline
(156) 5-{[4-(phenylsulfonyl)phenyl]sulfanyl}isoquinoline
(157) 5-{[4-(phenylsulfonyl)phenyl]sulfonyl}isoquinoline
(158) 6-(5-isoquinolylsulfanyl)-3-nitro-2-pyridylamine
(159) 6-(5-isoquinolylsulfonyl)-3-nitro-2-pyridylamine
(160) 6-(5-isoquinolylsulfanyl)-1,2-pyridine diamine
(161) 5-(5-isoquinolylsulfanyl)-2-methyl-1(3)H-imidazo[4,5-b]pyridine
(162) 7-(5-isoquinolylsulfanyl)-2-mehtyl-6-nitro-3,4-dihydro-4-quinazoline
(163) 7-(5-isoquinolylsulfanyl)-2-mehtyl-6-nitro-3,4-dihydro-4-quinazoline
(164) 5-(5-isoquinolylsulfanyl)-2-nitrobenzonitrile
(165) 2-amino-5-(5-isoquinolylsulfanyl)benzonitrile
(166) 7-(5-isoquinolylsulfonyl)-1,2,3,4-tetrahydro-9-acryldinylamine
(167) 5-[(5-nitro-2-pyridyl)sulfanyl]isoquinoline
(168) 5-[(5-nitro-2-pyridyl)sulfonyl]isoquinoline
(169) N1-{4-chloro-2-(ethylcarboxamide)-5-[(8-nitro-5-isoquinolyl)sulfanyl]phenyl}propanamide
(170) 6(5)-chloro-2-ethyl-5(6)-[(8-nitro-5-isoquinolyl)sulfanyl]-1H-benzo[d]imidazole
(171) 6(5)-chloro-2-ethyl-5(6)-[(8-nitro-5-isoquinolyl)sulfonyl]-1H-benzo[d]imidazole
(172) 2-cyclopentyl-5(6)-(5-isoquinolylsulfanyl)-6(5)-nitro-1H-benzo[d]imidazole
(173) 6(5)-chloro-2-cyclopentyl-5(6)-(5-isoquinolylsulfanyl)-1H-benzo[d]imidazole
(174) 2-(cyclopentylmethyl)-5(6)-(5-isoquinolylsulfonyl)-1H-benzo[d]imidazole (175) 2-(cyclopentylmethyl)-5(6)-(5-isoquinolylsulfonyl)-6 (5)-nitro-1H-benzo[d]imidazole As preferable compounds in the above compounds, (3), (11), (12), (48), (52), (59), (60), (74), (77), (80), (81), (83), (85), (87), (97), (99), (100), (101), (102), (104), (113), (119), (128), (130), (132), (133), (134), (141), (142), (143) can be exemplified. As most preferable compounds, (52), (60), (74), (77), (99), (100), (101), (102), (128), (130), (132), (133), (134), (141), (142), (143) can be exemplified. These compounds can be synthesized by using the same method as described in the following scheme of steps and the synthesis process described in examples.

The compounds (I) of the present invention produce salts with acids or bases. The salts of acids can be formed by using mineral acids such as hydrochloric acid, hydrobromic acid, hydroiodic acid, sulfuric acid, nitric acid and phosphoric acid; and organic acids such as formic acid, acetic acid, propionic acid, oxalic acid, malonic acid, succinic acid, fumaric acid, maleic acid, lactic acid, malic acid, citric acid, tartaric acid, carbonic acid, picric acid, methane sulfonic acid and glutamic acid.

The salts of bases can be formed by using inorganic bases such as sodium, potassium, magnesium, calcium and aluminunium; organic salts such as methyl amine, ethyl amine and ethanol amine; salts of basic amino acid such as lysine, arginine and ornithine and salts of ammonium. Further, the compounds (I) of the present invention may form hydrates, solvates of ethanol and the like, and crystalline polymorphisms.

The compounds related to the present invention can be prepared by the following (a), (b) and (c) methods.

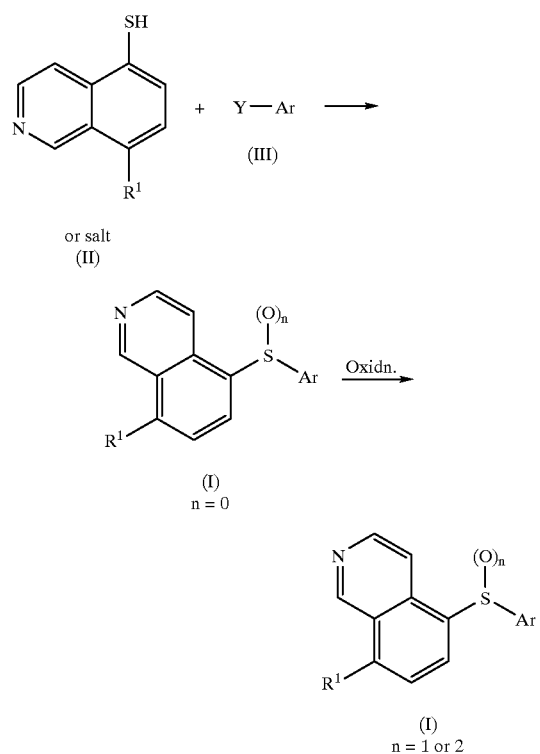

(a) Method
In the formula, Y shows a halogen atom or a diazonium halide, Ar shows an aromatic ring or heterocycle which may be substituted, $R^1$ shows a substituted group selected from the group of hydrogen, nitro and amino. The salt of a mercapto compound can be prepared by adding base such as sodium hydroxide, potassium hydroxide, sodium carbonate, potassium carbonate or sodium alkoxide to a corresponding acetylsulfanyl derivative or benzoylsulfanyl derivative in water or alcohol, and reacting the mixture at room temperature or under heat reflux.

The reaction is commonly conducted at room temperature or under heat reflux in a solvent such as dimethylformamide (DMF), dimethyl sulfoxide (DMSO), acetonitrile, acetone or tetrahydrofuran (THF). To accelerate the reaction, a base such as sodium hydroxide, potassium hydroxide, sodium hydride, potassium carbonate or sodium methoxide is preferably added. Thus obtained compound (I) of the present invention of n=0 is oxidized with an oxidizer such as hydrogen peroxide, organic peroxide, a manganese compound, chromic acid, organic peracid, peroxo sulfuric acid and oxonpersulfate compound, to produce compound (I) of the present invention of n=1 and 2.

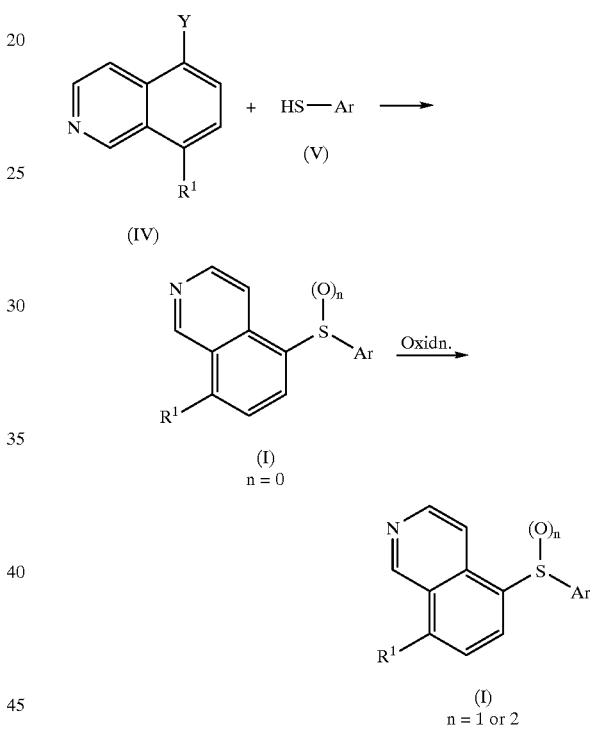

(b) method
In the formula, Y shows a halogen atom or a diazonium halide, Ar shows an aromatic ring or heterocycle which may be substituted, $R^1$ shows a substituted group selected from the group of hydrogen, nitro and amino.

Using a 5-isoquinoline halogen derivative and a mercapto derivative, compound (I) of the present invention can be produced by the same method as (a) method.

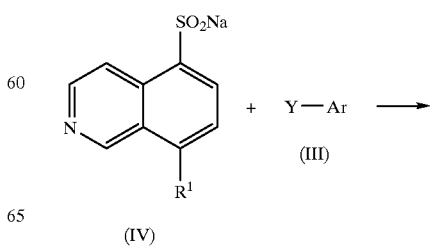

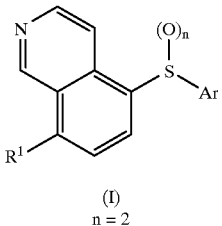

(I) n = 2

(c) method

In the formula, Y shows a halogen atom or a diazonium halide, Ar shows an aromatic ring or heterocycle which may be substituted, $R^1$ shows a substituted group selected from the group of hydrogen, nitro and amino. Using a salt of 5-isoquinolinesulfinic acid obtained from 5-isoquinoline sulfonyl chloride, compound (I) of the present invention can be produced by the same method as (a) method.

Further, the compounds of the present invention can be produced by introducing or substituting new groups into the compounds obtained by the above procedure. For example, the compound (I) wherein n is 2 and Ar is 2-methyl-6-nitrobenzimidazole can be produced by nitration of 5-(5-isoquinolylsulfonyl)-2-methyl-6-nitro-1H-benzo[d] imidazole as shown in the following scheme.

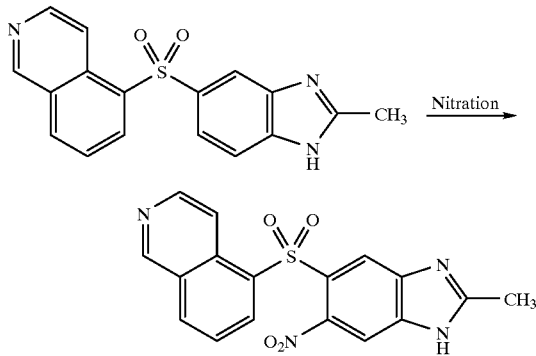

This nitration can be conducted by a process for reacting the isoquinoline derivatives of the present invention with nitric acid or its salt in sulfuric acid, acetic anhydride or acetic acid under ice cooling or heat stirring, or by a process for heating the derivatives with nitronium tetrafluoroborate in an organic solvent such as sulfolane.

Thus obtained compounds of the present invention are isolated and purified as they are or as their salts. The isolation and purification are performed by applying conventional procedure such as extraction, concentration, distillation, crystalization, filtration, recrystalization, and various types of chromatography.

The pharmaceutical preparations containing one or more the compounds of the present invention or their salts as effective ingredients can be prepared by using pharmaceutically acceptable carriers or vehicles, or the other additives. As the carriers and vehicles for preparations, solid or liquid such as lactose, magnesium stearate, starch, talc, gelatin, agar, pectin, arabic gam, olive oil, sesame oil, cacao butter, ethylene glycol or the other common use materials can be used.

The compounds of the present invention may be in any form of, for example, tablets, capsules, granules, powder, liquid for oral administration, or intravenous injection or intramuscular injection, suppository, pecutanious for parenteral administration. Although the dosage may vary by a variety of factors, including the age and sex of the patient, one mg to 1000 mg, preferably from 10 mg to 200 mg per adult per day, are useful in the oral administration at a time or several times per day, or from 1 mg to 500 mg per adult per dose in the parenteral administration, at a time or several times per day or continuously in the range of one hour to 24 hours per day. As described above, since the dosage levels vary widely depending on the condition of the patient and other factors, these may contain at less or more than the above-mentioned dosage levels.

BRIEF DESCRIPTION OF DRAWINGS

FIG. 1 is a graph showing a suppressive effect of the compounds of the present invention to nerve cells in a model of colchicine induced neuronal cell death.

FIG. 2 is a graph showing a suppressive effect of the compounds of the present invention to nerve cells in a model of 6-hydroxy dopamine induced neuronal cell death.

FIG. 3 is a graph showing a suppressive effect of the compounds of the present invention to nerve cells in a model of 6-hydroxy dopamine induced neuronal cell death.

FIG. 4 is a graph showing a suppressive effect of the compounds of the present invention to neuronal cells in a model of 6-hydroxy dopamine induced neuronal cell death.

BEST MODE FOR CARRYING OUT THE INVENTION

The following Examples are intended to further illustrate the present invention and not to limit the invention by these Examples.

EXAMPLE 1

5-(4-Nitrophenylsulfanyl)isoquinoline

5-Benzoylsulfanylisoquinoline 1.41 g (5.3 mmol) was dissolved in a mixture solution of methanol (50 ml) and chloroform (5 ml), sodium methoxide 500 mg (9.3 mmol) was added, and the mixture was stirred at room temperature for 30 minutes. The reaction mixture was concentrated under reduced pressure, the resulting residue was dissolved in DMF 50 ml, 4-nitrofluorobenzene 0.75 g (5.3 mmol) was added, and the mixture was heated and stirred at 100° C. for 3.5 hours. After cooling, water was added to the reaction mixture, the resulting precipitate was collected and washed with water to obtain 5-(4-nitrophenylsulfanyl)isoquinoline 1.36 g (90.9%).

Melting point: 137–139° C.

Mass spectrometry (m/z): 283 (M+1)

Nuclear magnetic resonance spectrum (DMSO-$d_6$) δ: 9.47(1H,s), 8.58(1H,d), 8.39(1H,d), 8.23(1H,d), 8.07(2H,d), 7.92(1H,d), 7.83(1H,dd), 7.18(2H,d).

Infrared absorption spectrum $v_{max}$ (KBr) cm$^{-1}$: 1575, 1500, 1330

Element anlysis values (calculated as $C_{15}H_{10}N_2O_2S.1/8H_2O$)

|  | C(%) | H(%) | N(%) | S(%) |
| --- | --- | --- | --- | --- |
| Theoretical values | 63.31 | 3.60 | 9.77 | 11.18 |
| Found values | 63.25 | 3.50 | 9.79 | 11.42 |

EXAMPLE 2

5-(4-Nitrophenylsulfonyl)isoquinoline 5-(4-Nitrophenylsulfonyl)isoquinoline was synthesized by the following three methods (a), (b) and (c).

(a) method 5-(4-Nitrophenylsulfanyl)isoquinoline 100 mg (0.4 mmol) was dissolved in concentrated sulfuric acid 2.0 ml, Beckman's reagent 3.0 ml (a mixture of $K_2Cr_2O_7$ 1 g-$H_2SO_4$ 1 ml-$H_2O$ 9 ml) was added dropwise, and the mixture was stirred at room temperature for 3 hours. After water was added to the reaction mixture, the solution was neutralized with 4 N sodium hydroxide, and precipitates were filtered, washed with water, and recrystallized from methanol to give 5-(4-nitrophenylsulfonyl)isoquinoline 70 mg (63.6%).

(b) method 5-(4-Nitrophenylsulfanyl)isoquinoline 2.01 g (7.1 mmol) was dissolved in concentrated sulfuric acid 20 ml, OXONE (trademark) 10.80 g (17.6 mmol) was added in portions, and the mixture was stirred at room temperature for 1 hour. After water was added to the reaction mixture, the solution was neutralized with a solution of 4 N sodium hydroxide in water and extracted with ethyl acetate. The organic layer was washed with a saturated sodium chloride, dried over anhydrous sodium sulfate and concentrated under reduced pressure. The resulting residue was recrystallized from ethyl acetate-hexane to give 5-(4-nitrophenylsulfonyl) isoquinoline 1.99 g (88.8%).

(c) method

After a mixture of 5-isoquinolinesulfonyl chloride 1.58 g (7.0 mmol), sodium sulfite 880 mg (7.0 mmol) and water 10 ml was heated and refluxed for 1 hour, the reaction mixture was concentrated under reduced pressure. Ethanol was added to the resulting residue to filter off insoluble materials, and the filtrate was concentrated under reduced pressure to give sodium 5-isoquinolinesulfinate 375 mg (25.0%).

A mixture of sodium 5-isoquinolinesulfinate 100 mg (0.5 mmol), 4-fluoronitrobenzene 70 mg (0.5 mmol), ethylene glycol 0.1 ml and ethyleneglycoldiethylether 0.1 ml was heated and refluxed for 3.5 hours. Water was added to the reaction mixture, and the solution was extracted with ethyl acetate, the organic layer washed with a saturated sodium chloride, dried over anhydrous sodium sulfate, and concentrated under reduced pressure. The resulting residue was recrystallized from methanol to give 5-(4-nitrophenylsulfonyl)isoquinoline 30 mg (20.3%).

Melting point: 192–194° C.

Mass spectrometry (m/z): 315 (M+1)

Nuclear magnetic resonance spectrum (CDCl$_3$) δ: 9.35 (1H,s), 8.75(1H,d), 8.67(1H,d), 8.34–8.30(4H,m), 8.16(1H, d), 7.84(1H,dd).

Infrared absorption spectrum $v_{max}$ (KBr) cm$^{-1}$: 3100, 1605, 1540, 1350, 1160, 1140

Element analysis values (calculated as $C_{15}H_{10}N_2O_4S$)

|  | C(%) | H(%) | N(%) | S(%) |
| --- | --- | --- | --- | --- |
| Theoretical values | 57.32 | 3.21 | 8.91 | 10.20 |
| Found values | 57.30 | 2.96 | 8.56 | 10.38 |

EXAMPLE 3

4-(5-Isoquinolylsulfonyl)aniline 5-(4-Nitrophenylsulfonyl)isoquinoline 160 mg (0.6 mmol) was dissolved in concentrated hydrochloric acid 170 ml, stannous chloride dihydrate 650 mg (2.9 mmol) was added, and the mixture was stirred overnight at room temperature. 4 N sodium hydroxide in water was added to the reaction solution, and the resulting alkaline solution was extracted with ethyl acetate. The organic layer was washed with saturated sodium chloride, dried over anhydrous sodium sulfate, and concentrated under reduced pressure. The resulting residue was recrystallized from methanol to give 4-(5-isoquinolylsulfonyl)aniline 110 mg (76.5%).

Melting point: 207–209° C.

Mass spectrometry (m/z): 285 (M+1)

Nuclear magnetic resonance spectrum (CD$_3$OD) δ: 9.32 (1H,s), 8.59–8.53(3H,m), 8.35(1H,d), 7.83(1H,dd), 7.65 (2H,d), 6.64(2H,d).

Infrared absorption spectrum $v_{max}$ (KBr) cm$^{-1}$: 3450, 3350, 1630, 1590, 1500, 1300, 1130, 1085, 700, 590.

Element anlysis values (calculated as $C_{15}H_{12}N_2O_2S$)

|  | C(%) | H(%) | N(%) | S(%) |
| --- | --- | --- | --- | --- |
| Theoretical values | 63.36 | 4.25 | 9.85 | 11.28 |
| Found values | 63.10 | 4.46 | 9.54 | 10.96 |

Example 4

N1-[4-(5-Isoquinolylsulfonyl)phenyl]acetamide 4-(5-Isoquinolylsulfonyl)aniline 20 mg (0.1 mmol) was dissolved in a mixture solution of acetic anhydride 2 ml and pyridine 2 ml, the mixture was stirred overnight at room temperature, water was added to the reaction solution, and the solution was extracted with ethyl acetate. The organic layer was washed with saturated potassium hydrogensulfate and with saturated sodium hydrogencarbonate, dried over anhydrous sodium sulfate, and concentrated under reduced pressure to give N1-[4-(5-isoquinolylsulfonyl)phenyl] acetamide 10 mg (44.3%)

Melting point: 240–244° C.

Mass spectrometry (m/z): 327 (M+1)

Nuclear magnetic resonance spectrum (DMSO-d$_6$) δ: 10.35(1H,s), 9.45(1H,s), 8.64–8.61(2H,m), 8.49(1H,d), 8.34 (1H,d), 7.99–7.90(3H,m), 7.77(2H,d), 2.04(3H,s).

Infrared absorption spectrum $v_{max}$ (KBr) cm$^{-1}$: 1700, 1590, 1540, 1320, 1310, 1160, 1140.

Element anlysis values (calculated as $C_{17}H_{14}N_2O_3S.1/8H_2O$)

|  | C(%) | H(%) | N(%) | S(%) |
| --- | --- | --- | --- | --- |
| Theoretical values | 62.13 | 4.29 | 8.52 | 9.76 |
| Found values | 62.30 | 4.61 | 8.03 | 9.84 |

EXAMPLE 5

5-[4-(Pyrrole-1-yl)phenylsulfonyl]isoquinoline

A mixture solution of 4-(5-isoquinolylsulfonyl)aniline 300 mg (1.1 mmol), 2,5-dimethoxytetrahydrofuran 160 mg (1.2 mmol) and acetic acid 2 ml was heated and refluxed for 1 hour. Water was added to the reaction solution, and the solution was extracted with ethyl acetate. The organic layer was washed with saturated sodium hydrogencarbonate and saturated sodium chloride, dried over anhydrous sodium sulfate, and concentrated under reduced pressure. The resulting residue was recrystalized from ethyl acetate-hexane to give 5-[4-(pyrrole-1-yl)phenylsulfonyl]isoquinoline 280 mg (83.0%).

Melting point: 207–210° C.

Mass spectrometry (m/z): 335 (M+1)

Nuclear magnetic resonance spectrum (DMSO-$d_6$) δ: 9.46(1H,s), 8.69(1H,dd), 8.65(1H,d), 8.51(1H,d), 8.37(1H, d), 8.05(2H,d), 7.45(1H,dd), 6.29(2H,d).

Infrared absorption spectrum $\nu_{max}$ (KBr) cm$^{-1}$: 1600, 1510, 1340, 1300, 1150, 730, 610.

Element anlysis values (calculated as $C_{19}H_{14}N_2O_2S.1/4H_2O$)

|  | C(%) | H(%) | N(%) | S(%) |
|---|---|---|---|---|
| Theoretical values | 67.34 | 4.31 | 8.27 | 9.46 |
| Found values | 67.51 | 4.38 | 8.10 | 9.26 |

EXAMPLE 6

5-(5-Isoquinolylsulfanyl)-2-nitroaniline

According to the method in Example 1, 5-(5-isoquinolylsulfanyl)2-nitroaniline 5.86 g (99.0%) was obtained from 5-benzoylsulfanylisoquinoline 5.33 g (20.1 mmol), sodium methoxide 2.79 g (51.7 mmol) and 5-chloro-2-nitroaniline 3.44 g (19.9 mmol).

Melting point: 204–206° C.

Mass spectrometry (m/z): 298 (M+1)

Nuclear magnetic resonance spectrum (DMSO-$d_6$) δ: 9.44(1H,s), 8.58(1H,d), 8.35(1H,d), 8.17(1H,d), 7.91–7.78 (3H,m), 7.33(1H,s), 6.41(1H,d), 6.29(1H,d).

Infrared absorption spectrum $\nu_{max}$ (KBr) cm$^{-1}$: 3450, 3270, 3130, 1620, 1570, 1490, 1470, 1320, 1240

Element anlysis values (calculated as $C_{15}H_{11}N_3O_2S.1/8H_2O$)

|  | C(%) | H(%) | N(%) | S(%) |
|---|---|---|---|---|
| Theoretical values | 60.14 | 3.78 | 14.01 | 10.70 |
| Found values | 59.88 | 3.69 | 14.23 | 10.94 |

EXAMPLE 7

5-(5-Isoquinolylsulfonyl)-2-nitroaniline 5-(5-Isoquinolylsulfonyl)-2-nitroaniline was prepared by the following two methods (a) and (b).

(a) method 5-(5-Isoquinolylsulfanyl)-2-nitroaniline 300 mg (1.0 mmol) was dissolved in a mixture solution of 5% sulfuric acid 2 ml and acetic acid 6 ml, potassium permanganate 200 mg (1.3 mmol) was added in an ice bath, and the mixture was stirred for 3 hours at 0° C. After stirring at room temperature for 3 hours, the mixture was neutralized with 2N sodium hydroxide and extracted with ethyl acetate (70 ml×3). The organic layer was dried over potassium carbonate, and concentrated under reduced pressure. The resulting residue was recrystalized from methanol-water to give 5-(5-isoquinolylsulfonyl)-2-nitroaniline 59 mg (17.9%).

(b) method

According to the method in (b) method of Example 2, a mixture of 5-(5-isoquinolylsulfanyl)-2-nitroaniline 5.00 g (16.8 mmol), concentrated sulfuric acid 50 ml and OXONE (trademark) 20.70 g (33.7 mmol) was stirred at room temperature for 30 minutes. Water was added to the reaction mixture, the solution was neutralized with an aqueous 4N sodium hydroxide solution, the precipitates were collected and washed with water then with ether to give 5-(5-isoquinolylsulfonyl)-2-nitroaniline 5.54 g (quantitative).

Melting point: >270° C.

Mass spectrometry (m/z): 330 (M+1)

Nuclear magnetic resonance spectrum (DMSO-$d_6$) δ: 9.34(1H,d), 8.59(1H,d), 8.14(1H,dd), 8.09(1H,dd), 8.01(1H, dd), 7.99(1H,d), 7.69(1H,dd), 6.35(1H,dd), 6.21(1H,dd), 5.99(2H,brs).

Infrared absorption spectrum $\nu_{max}$ (KBr) cm$^{-1}$: 3470, 1620, 1570, 1500, 1330, 1320, 1160, 1140, 840, 715

Element anlysis values (calculated as $C_{15}H_{11}N_3O_4S$)

|  | C(%) | H(%) | S(%) |
|---|---|---|---|
| Theoretical values | 54.71 | 3.37 | 9.74 |
| Found values | 54.86 | 3.41 | 9.96 |

EXAMPLE 8

4-(5-Isoquinolylsulfanyl)-1,2-benzenediamine

According to the method in Example 3, 4-(5-isoquinolylsulfanyl)-1,2-benzenediamine 4.27 g (81.1%) was obtained from 5-(5-isoquinolylsulfanyl)-2-nitroaniline 5.86 g (19.7 mmol), concentrated hydrochloric acid 170 ml and stannous chloride dihydrate 15.88 g (70.4 mmol).

Melting point: 182–183° C.

Mass spectrometry (m/z): 268 (M+1)

Nuclear magnetic resonance spectrum (DMSO-$d_6$) δ: 9.30(1H,d), 8.55(1H,d), 8.00(1H,d), 7.89(1H,d), 7.52(1H, dd), 7.26(1H,dd), 6.68–6.57(3H,m), 4.80(4H,brs).

Infrared absorption spectrum $\nu_{max}$ (KBr) cm$^{-1}$: 3450, 3270, 3130, 1620, 1570, 1490, 1470, 1320, 1240

Element anlysis values (calculated as $C_{15}H_{13}N_3S.1/8H_2O$)

|  | C(%) | H(%) | N(%) | S(%) |
|---|---|---|---|---|
| Theoretical values | 66.83 | 4.91 | 15.59 | 11.89 |
| Found values | 67.27 | 5.04 | 15.99 | 11.67 |

EXAMPLE 9

4-(5-Isoquinolylsulfonyl)-1,2-benzenediamine

According to the method in Example 3, 4-(5-isoquinolylsulfonyl)-1,2-benzenediamine 2.91 g (80.2%) was obtained from 4-(5-isoquinolylsulfonyl)-2-nitroaniline 4.00 g (12.1 mmol), concentrated hydrochloric acid 100 ml and stannous chloride dihydrate 17.2 g (76.2 mmol).

Melting point: 256–261° C.

Mass spectrometry (m/z): 300 (M+1)

Nuclear magnetic resonance spectrum (CD$_3$OD) δ: 9.26 (1H,s), 8.56–8.53(2H,m), 8.48(1H,dd), 8.22(1H,d), 7.71 (1H,dd), 7.18(1H,dd), 7.12(1H,d), 6.55(1H,d).

Infrared absorption spectrum $\nu_{max}$ (KBr) cm$^{-1}$: 3350, 1620, 1130

EXAMPLE 10

4-(5-Isoquinolylsulfanyl)-3-nitroaniline

5-Isoquinolinethiol 1.00 g (6.2 mmol) was dissolved in DMF 14 ml, potassium carbonate 1.01 g (7.3 mmol) and 4-fluoro-3-nitroaniline 0.96 g (6.1 mmol) were added and the mixture was heated with stirring for 2 hours at 100° C. The reaction solution was concentrated under reduced pressure, the resulting residue was washed with water to obtain 4-(5-isoquinolylsulfanyl)-3-nitroaniline 1.75 g (96.5%).

Melting point: 222–227° C.

Mass spectrometry (m/z): 298 (M+1)

Nuclear magnetic resonance spectrum (DMSO-$d_6$) δ: 9.39(1H,s), 8.53(1H,d), 8.20(1H,d), 7.85–7.87(2H,m), 7.71 (1H,dd), 7.32(1H,d), 6.69(1H,dd), 6.62(1H,d), 5.90(2H,s).

Infrared absorption spectrum $v_{max}$ (KBr) cm$^{-1}$: 3450, 1510, 1310.

Element anlysis values (calculated as $C_{15}H_{11}N_3O_2S$)

|  | C(%) | H(%) | N(%) | S(%) |
| --- | --- | --- | --- | --- |
| Theoretical values | 60.59 | 3.73 | 14.13 | 10.78 |
| Found values | 60.32 | 3.96 | 13.82 | 10.80 |

EXAMPLE 11

4-(5-Isoquinolylsulfonyl)-3-nitroaniline

According to the method in method (b) of Example 7, 4-(5-isoquinolylsulfonyl)-3-nitroaniline 340 mg (30.4%) was obtained from 4-(5-isoquinolylsulfanyl)-3-nitroaniline 1.00 g (3.4 mmol), concentrated sulfuric acid 10 ml and OXONE (trademark) 4.14 g (6.7 mmol).

Melting point: 258–260° C.

Mass spectrometry (m/z): 330 (M+1)

Nuclear magnetic resonance spectrum (DMSO-$d_6$) δ: 9.45(1H,s), 8.71(1H,d), 8.47(1H,d), 8.30(1H,d), 8.01(1H, dd), 7.72 (1H,dd), 7.68(1H,d), 7.47(1H,d), 7.24(1H,d), 6.49 (2H,s).

Infrared absorption spectrum $v_{max}$ (KBr) cm$^{-1}$: 3470, 3380, 1600, 1540, 1290, 1150.

Element anlysis values (calculated as $C_{15}H_{11}N_3O_4S$)

|  | C(%) | H(%) | N(%) | S(%) |
| --- | --- | --- | --- | --- |
| Theoretical values | 54.71 | 3.37 | 12.76 | 9.74 |
| Found values | 54.43 | 3.18 | 12.57 | 9.86 |

EXAMPLE 12

5-[2-Nitro-4-(pyrrol-1-yl)phenylsulfonyl]isoquinoline

According to the method in Example 5, 5-[2-nitro-4-(pyrrol-1-yl)phenylsulfonyl]isoquinoline 280 mg (83.0%) was obtained from 4-(5-isoquinolylsulfonyl)-3-nitroaniline 160 mg (0.5 mmol), 2,5-dimethoxytetrahydrofuran 160 mg (1.2 mmol) and acetic acid 2 ml.

Melting point: 177–180° C.

Mass spectrometry (m/z): 380 (M+1)

Nuclear magnetic resonance spectrum (DMSO-$d_6$) δ: 9.52(1H,s), 8.69(1H,d), 8.59(1H,d), 8.49(1H,dd), 8.46(1H, d), 8.38(1H,d), 8.28(1H,d), 8.13(1H,dd), 7.97(1H,dd), 7.63 (1H,dd), 6.37(1H,dd).

Infrared absorption spectrum $v_{max}$ (KBr) cm$^{-1}$: 1600, 1550, 1340, 1130.

Element anlysis values (calculated as $C_{19}H_{13}N_3O_4S$)

|  | C(%) | H(%) | N(%) | S(%) |
| --- | --- | --- | --- | --- |
| Theoretical values | 60.15 | 3.45 | 11.08 | 8.45 |
| Found values | 59.92 | 3.24 | 10.73 | 8.67 |

EXAMPLE 13

4-(5-Isoquinolylsulfanyl)-3-nitrobenzonitrile

According to the method in Example 10, 5-isoquinolinethiol 1.00 g (6.2 mmol) was dissolved in DMF 14 ml, potassium carbonate 1.60 g (11.6 mmol) and 4-chloro-3-nitrobenzonitrile 1.00 g (5.5 mmol) were added and stirred at room temperature for 15 minutes, and 4-(5-isoquinolylsulfanyl)-3-nitrobenzonitrile 1.69 g (quantitative) was obtained.

Melting point: 187–190° C.

Mass spectrometry (m/z): 308 (M+1)

Nuclear magnetic resonance spectrum (DMSO-$d_6$) δ: 9.46(1H,s), 8.79(1H,d), 8.53(1H,d), 8.44(1H,d), 8.29(1H,d), 7.85–7.90(2H,m), 7.74(1H,dd), 6.59(1H,d).

Infrared absorption spectrum $v_{max}$ (KBr) cm$^{-1}$: 2230, 1610, 1540, 1520, 1340.

Element anlysis values (calculated as $C_{16}H_9N_3O_2S$)

|  | C(%) | H(%) | N(%) | S(%) |
| --- | --- | --- | --- | --- |
| Theoretical values | 62.53 | 2.95 | 13.67 | 10.43 |
| Found values | 62.87 | 2.92 | 13.86 | 10.70 |

EXAMPLE 14

5-[2-Nitro-4-(1(2)H-1,2,3,4-tetrazol-5-yl)phenylsulfanyl]isoquinoline

According to the method in Example 10, 5-[2-nitro-4-(1(2)H-1,2,3,4-tetrazol-5-yl)phenylsulfanyl]isoquinoline 520 mg (90.8%) was obtained from 5-isoquinolinethiol 270 mg (1.6 mmol), DMF 7 ml, potassium carbonate 460 mg (3.3 mmol) and 5-(4-chloro-3-nitrophenyl)-1(2)H-1,2,3,4-tetrazol 350 mg (1.6 mmol).

Mass spectrometry (m/z): 351 (M+1)

Nuclear magnetic resonance spectrum (DMSO-$d_6$) δ: 9.46(1H,d), 8.80(1H,d), 8.54(1H,d), 8.40(1H,d), 7.91–7.94 (2H,m), 7.85(1H,dd), 6.59(1H,d).

Infrared absorption spectrum $v_{max}$ (KBr) cm$^{-1}$: 1620, 1530, 1420, 1330.

Element anlysis values (calculated as $C_{16}H_{10}N_6O_2S \cdot 1/2NH_3 \cdot 1/4H_2O$)

|  | C(%) | H(%) | N(%) | S(%) |
| --- | --- | --- | --- | --- |
| Theoretical values | 52.89 | 2.33 | 25.05 | 8.82 |
| Found values | 53.08 | 2.94 | 24.68 | 8.75 |

EXAMPLE 15

5-[2-Nitro-4-(1(2)H-1,2,3,4-tetrazol-5-yl)phenylsulfonyl]isoquinoline

According to the method in method (b) of Example 7, 5-[2-nitro-4-(1(2)H1,2,3,4-tetrazol-5-yl)phenylsulfanyl]

isoquinoline 200 mg (0.5 mmol), concentrated sulfuric acid 2 ml and OXONE (trademark) 670 mg (1.1 mmol) were reacted, the reaction solution was added to water, and the precipitates were filtered to obtain 5-[2-nitro-4-(1(2)H-1,2,3,4-tetrazol-5-yl)phenylsulfonyl]isoquinoline sulfate 200 mg (86.1%).

Mass spectrometry (m/z): 383 (M+1)

Nuclear magnetic resonance spectrum (DMSO-$d_6$) δ: 9.58(1H,s), 8.64–8.71(4H,m), 8.58(1H,dd), 8.55(1H,dd), 8.30(1H,d), 8.03(1H,dd).

Infrared absorption spectrum $v_{max}$ (KBr) cm$^{-1}$: 1550, 1140.

Element anlysis values (calculated as $C_{16}H_{10}N_6O_4S.1/2H_2SO_4.1/4H_2O$)

|  | C(%) | H(%) | N(%) | S(%) |
|---|---|---|---|---|
| Theoretical values | 44.09 | 2.66 | 19.28 | 11.03 |
| Found values | 44.04 | 2.76 | 18.94 | 11.28 |

EXAMPLE 16

5-(5-Isoquinolylsulfanyl)-2-nitrophenol

According to the method in Example 10, 5-(5-isoquinolylsulfanyl)-2-nitrophenol 1.51 g (79.4%) was obtained from 5-isoquinolinethiol 1.05 g (6.5 mmol), DMF 30 ml, potassium carbonate 1.80 g (13.0 mmol) and 3-hydroxy-4-nitrofluorobenzene 1.00 g (6.4 mmol).

Melting point: 139–141° C.

Mass spectrometry (m/z): 299 (M+1)

Nuclear magnetic resonance spectrum (DMSO-$d_6$) δ: 9.46(1H,d), 8.59(1H,d), 8.37(1H,d), 8.20(1H,dd), 7.92(1H,d), 7.79–7.83(2H,m), 6.65(1H,dd), 6.52(1H,d).

Infrared absorption spectrum $v_{max}$ (KBr) cm$^{-1}$: 1600, 1570, 1320, 1240, 750.

Element anlysis values (calculated as $C_{15}H_{10}N_2O_3S.1/8H_2O$)

|  | C(%) | H(%) | N(%) | S(%) |
|---|---|---|---|---|
| Theoretical values | 59.93 | 3.44 | 9.32 | 10.67 |
| Found values | 59.96 | 3.21 | 9.44 | 10.91 |

EXAMPLE 17

2-Amino-5-(5-isoquinolylsulfanyl)phenol

According to the method in Example 3, 2-amino-5-(5-isoquinolylsulfanyl)phenol 214 mg (92.1%) was obtained from 5-(5-isoquinolylsulfanyl)-2-nitrophenol 290 mg (0.9 mmol), concentrated hydrochloric acid 10 ml and stannous chloride dihydrate 780 mg (3.5 mmol).

Melting point: 189–191° C.

Mass spectrometry (m/z): 269 (M+1)

Nuclear magnetic resonance spectrum (DMSO-$d_6$) δ: 9.31(1H,d), 8.56(1H,d), 8.01(1H,d), 7.92(1H,d), 7.55(1H,dd), 7.32(1H,dd), 6.80(1H,dd), 6.77(1H,d), 6.66(1H,d).

Infrared absorption spectrum $v_{max}$ (KBr) cm$^{-1}$: 3450, 3360, 1600, 1505, 1290, 820.

Element anlysis values (calculated as $C_{15}H_{12}NOS.1/16H_2O$)

|  | C(%) | H(%) | N(%) | S(%) |
|---|---|---|---|---|
| Theoretical values | 66.53 | 4.52 | 10.35 | 11.85 |
| Found values | 66.90 | 4.39 | 9.99 | 12.11 |

EXAMPLE 18

2-Amino-5-(5-isoquinolylsulfonyl)phenol

According to the method in Example 3, 2-amino-5-(5-isoquinolylsulfonyl)phenol 340 mg (75.1%) was obtained from 5-(5-isoquinolylsulfonyl)-2-nitrophenol 500 mg (1.5 mmol), concentrated hydrochloric acid 5 ml and stannous chloride dihydrate 1.40 g (6.2 mmol).

Melting point: 251–253° C.

Mass spectrometry (m/z): 3011 (M+1)

Nuclear magnetic resonance spectrum (DMSO-$d_6$) δ: 9.80(1H,brs), 9.44(1H,s), 8.64(1H,d), 8.47(1H,d), 8.43(1H,d), 8.36(1H,d), 7.87(1H,dd), 7.27(1H,d), 7.09(1H,s), 6.64(1H,dd), 5.60(2H,s).

Infrared absorption spectrum $v_{max}$ (KBr) cm$^{-1}$: 3480, 3370, 1620, 1300, 1130.

Element anlysis values (calculated as $C_{15}H_{12}N_2O_3S$)

|  | C(%) | H(%) | N(%) | S(%) |
|---|---|---|---|---|
| Theoretical values | 59.99 | 4.03 | 9.33 | 10.68 |
| Found values | 60.05 | 4.28 | 9.14 | 10.52 |

EXAMPLE 19

5-[3-Hydroxy-4-(pyrrol-1-yl)phenylsulfonyl]isoquinoline

According to the method in Example 5, 5-[3-hydroxy-4-(pyrrol-1-yl)phenylsulfonyl]isoquinoline 210 mg (75.7%) was obtained from 2-amino-5-(5-isoquinolylsulfonyl)phenol 250 mg (0.8 mmol), 2,5-dimethoxytetrahydrofuran 110 mg (0.8 mmol) and acetic acid 2 ml.

Melting point: 258–264° C.

Mass spectrometry (m/z): 351 (M+1)

Nuclear magnetic resonance spectrum (DMSO-$d_6$) δ: 9.41(1H,s), 8.68(1H,d), 8.65(1H,d), 8.34(1H,d), 7.96(1H,dd), 7.55(1H,d), 7.46–7.51(2H,m), 7.18(2H,dd), 6.18(2H,dd).

Infrared absorption spectrum $v_{max}$ (KBr) cm$^{-1}$: 1590, 1520, 1410, 1320, 1160, 1140.

Element anlysis values (calculated as $C_{19}H_{14}N_2O_3S$)

|  | C(%) | H(%) | N(%) | S(%) |
|---|---|---|---|---|
| Theoretical values | 65.13 | 4.03 | 7.99 | 9.15 |
| Found values | 65.29 | 4.37 | 7.77 | 9.39 |

EXAMPLE 20

5-[2-Fluoro-4-(1(2)H-1,2,3,4-tetrazol-5-yl)phenylsulfanyl]isoquinoline

Sodium azide 60 mg (0.9 mmol) and ammonium chloride 100 mg (1.9 mmol) were added to a DMF solution 2 ml of 4-(5-isoquinolylsulfanyl)-3-fluorobenzonitrile 200 mg (0.7 mmol), and the mixture was stirred overnight at 110° C. The reaction solution was added to ice water, the precipitates were filtered, washed with water and with acetone, and 5-[2-fluoro-4-(1(2)H-1,2,3,4-tetrazol-5-yl)phenylsulfanyl]isoquinoline 150 mg (51.6%) was obtained.

Melting point: 262–264° C.

Mass spectrometry (m/z): 324 (M+1)

Nuclear magnetic resonance spectrum (DMSO-$d_6$) δ: 9.44(1H,s), 8.59(1H,d), 8.30(1H,d), 8.08(1H,d), 8.00(1H,d), 7.91(1H,dd), 7.77(1H,dd), 7.00(1H,dd).

Infrared absorption spectrum $v_{max}$ (KBr) cm$^{-1}$: 1620, 1460, 820.

Element anlysis values (calculated as $C_{16}H_{10}FN_5S$)

|  | C(%) | H(%) | N(%) | S(%) |
| --- | --- | --- | --- | --- |
| Theoretical values | 59.43 | 3.12 | 21.66 | 9.91 |
| Found values | 59.68 | 3.17 | 21.64 | 9.96 |

EXAMPLE 21

5-[2-Fluoro-4-(1(2)H-1,2,3,4-tetrazol-5-yl)phenylsulfonyl]isoquinoline

According to the method in method (b) of Example 7, 5-[2-fluoro-4-(1(2)H-1,2,3,4-tetrazol-5-yl)phenylsulfonyl]isoquinoline 100 mg (37.5%) was obtained from 5-[2-fluoro-4-(1(2)H-1,2,3,4-tetrazol-5-yl)phenylsulfanyl]isoquinoline 240 mg (0.7 mmol), concentrated sulfuric acid 5 ml and OXONE (trademark) 920 mg (1.5 mmol).

Melting point: 265–267° C.

Mass spectrometry (m/z): 356 (M+1)

Nuclear magnetic resonance spectrum (DMSO-$d_6$) δ: 9.50(1H,s), 8.75(1H,d), 8.56–8.64(3H,m), 8.22(1H,d), 8.19(1H,dd), 8.01(1H,dd), 7.93(1H,dd).

Infrared absorption spectrum $v_{max}$ (KBr) cm$^{-1}$: 1620, 1340, 1160, 620.

Element anlysis values (calculated as $C_{16}H_{10}FN_5O_2S$)

|  | C(%) | H(%) | N(%) | S(%) |
| --- | --- | --- | --- | --- |
| Theoretical values | 54.08 | 2.84 | 19.08 | 9.02 |
| Found values | 54.42 | 2.89 | 19.46 | 8.97 |

EXAMPLE 22

5-(2-Chloro-4-nitrophenylsulfonyl)isoquinoline

According to the method in method (b) of Example 7, 5-(2-chloro-4-nitrophenylsulfonyl)isoquinoline sulfate 1.40 g (97.8%) was obtained from 5-[2-chloro-4-nitrophenylsulfanyl)isoquinoline 1.14 g (3.6 mmol), 50% sulfuric acid 34 ml and OXONE (trademark) 5.60 g (9.1 mmol).

Melting point: 207–216° C.

Mass spectrometry (m/z): 349 (M+1)

Nuclear magnetic resonance spectrum (DMSO-$d_6$) δ: 9.72(1H,s), 8.93(1H,d), 8.82(1H,d), 8.76(1H,d), 8.67(1H,d), 8.47(1H,dd), 8.37(1H,d), 8.29(1H,d), 8.11(1H,dd).

Infrared absorption spectrum $v_{max}$ (KBr) cm$^{-1}$: 1530, 1350, 1160, 1140.

Element anlysis values (calculated as $C_{15}H_9ClN_2O_4S.1/4H_2SO_4$)

|  | C(%) | H(%) | N(%) | S(%) |
| --- | --- | --- | --- | --- |
| Theoretical values | 4826 | 2.57 | 7.50 | 10.74 |
| Found values | 48.34 | 2.43 | 7.49 | 10.68 |

EXAMPLE 23

3-Chloro-4-(5-isoquinolylsulfonyl)aniline

According to the method in Example 3, 3-chloro-4-(5-isoquinolylsulfonyl)aniline 1.20 g (99.8%) was obtained from 5-(2-chloro-4-nitrophenylsulfonyl)isoquinoline 1.50 g (3.8 mmol), concentrated hydrochloric acid 35 ml and stannous chloride dihydrate 3.00 g (13.3 mmol).

Mass spectrometry (m/z): 319 (M+1)

Nuclear magnetic resonance spectrum (DMSO-$d_6$) δ: 9.45(1H,d), 8.61(1H,dd), 8.58(1H,d), 8.47(1H,d), 8.14(1H,d), 8.10(1H,d), 7.90(1H,dd), 6.71(1H,dd), 6.55(1H,d), 6.49(2H,s).

Infrared absorption spectrum $v_{max}$ (KBr) cm$^{-1}$: 3450, 1590, 1310, 1140.

Element anlysis values (calculated as $C_{15}H_{11}ClN_2O_2S.1/4H_2O$)

|  | C(%) | H(%) | S(%) |
| --- | --- | --- | --- |
| Theoretical values | 55.73 | 3.59 | 9.92 |
| Found values | 55.93 | 3.81 | 9.63 |

EXAMPLE 24

5[2-Chloro-4-(pyrrol-1-yl)phenylsulfonyl]isoquinoline

According to the method in Example 5, 5[2-chloro-4-(pyrrol-1-yl)phenylsulfonyl]isoquinoline 290 mg (82.2%) was obtained from 3-chloro-4-(5-isoquinolylsulfonyl)aniline 300 mg (0.9 mmol), 2,5-dimethoxytetrahydrofuran 140 mg (1.1 mmol) and acetic acid 2 ml.

Melting point: 161–165° C.

Mass spectrometry (m/z): 369 (M+1)

Nuclear magnetic resonance spectrum (DMSO-$d_6$) δ: 9.49(1H,s), 8.75(1H,s), 8.56–8.6 (3H,m), 8.10(1H,d), 7.94–7.99(2H,m), 7.89(1H,d), 7.57(2H,s), 6.32(2H,s).

Infrared absorption spectrum $v_{max}$ (KBr) cm$^{-1}$: 1590, 1500, 1340, 1330, 620.

Element anlysis values (calculated as $C_{19}H_{13}ClN_2O_2S$)

|  | C(%) | H(%) | N(%) | S(%) |
| --- | --- | --- | --- | --- |
| Theoretical values | 61.87 | 3.55 | 7.59 | 8.69 |
| Found values | 62.04 | 3.69 | 7.51 | 8.50 |

EXAMPLE 25

3-Chloro-4-(5-isoquinolylsulfanyl)benzonitrile

According to the method in Example 10, 5-isoquinolinethiol 1.00 g (6.2 mmol), DMF 30 ml, potassium carbonate 1.60 g (11.6 mmol) and 3-chloro-4-fluorobenzonitrile 0.90 g (5.8 mmol) were stirred at 100° C. for 30 minutes, and 3-chloro-4-(5-isoquinolylsulfanyl)benzonitrile 1.55 g (90.3%) was obtained.

Melting point: 126–128° C.

Mass spectrometry (m/z): 297 (M+1)

Nuclear magnetic resonance spectrum (DMSO-$d_6$) δ: 9.47(1H,d), 8.56(1H,d), 8.41(1H,d), 8.23(1H,dd), 8.11(1H,d), 7.85(1H,d), 7.83(1H,dd), 7.47(1H,dd), 6.39(1H,d).

Infrared absorption spectrum $\nu_{max}$ (KBr) cm$^{-1}$: 2220, 1580, 1460, 1030.

Element anlysis values (calculated as $C_{16}H_9ClN_2S$)

|  | C(%) | H(%) | N(%) | S(%) |
| --- | --- | --- | --- | --- |
| Theoretical values | 64.75 | 3.06 | 9.44 | 10.80 |
| Found values | 65.15 | 3.03 | 9.47 | 10.67 |

EXAMPLE 26

5-[2-Chloro-4-(1(2)H-1,2,3,4-tetrazol-5-yl)phenylsulfanyl]isoquinoline

According to the method in Example 20, 3-chloro-4-(5-isoquinolylsulfanyl)benzonitrile 500 mg (1.7 mmol), a DMF solution 5 ml, sodium azide 140 mg (2.2 mmol) and ammonium chloride 230 mg (4.2 mmol) were reacted. The reaction solution was added to ice water and extracted with ethyl acetate, and 5-[2-chloro-4-(1(2)H-1,2,3,4-tetrazol-5-yl)phenylsulfanyl]isoquinoline 390 mg (68.1%) was obtained.

Mass spectrometry (m/z): 340 (M+1)

Nuclear magnetic resonance spectrum (DMSO-$d_6$) δ: 9.46(1H,s), 8.58(1H,d), 8.38(1H,d), 8.18(1H,d), 8.15(1H,d), 7.90(1H,d), 7.83(1H,dd), 7.71(1H,dd), 6.64(1H,d).

Infrared absorption spectrum $\nu_{max}$ (KBr) cm$^{-1}$: 1610, 1470, 1430, 1030, 830.

Element anlysis values (calculated as $C_{16}H_{10}ClN_5S \cdot 1/2H_2O$)

|  | C(%) | H(%) | N(%) | S(%) |
| --- | --- | --- | --- | --- |
| Theoretical values | 55.09 | 3.18 | 20.08 | 9.19 |
| Found values | 55.32 | 3.43 | 19.78 | 9.14 |

EXAMPLE 27

5-[2-Chloro-4-(1(2)H-1,2,3,4-tetrazol-5-yl)phenylsulfonyl]isoquinoline

According to the method in method (b) of Example 7, 5-[2-chloro-4-(1(2)H-1,2,3,4-tetrazol-5-yl)phenylsulfonyl]isoquinoline sulfate 160 mg (80.9%) was obtained from 5-[2-chloro-4-(1(2)H-1,2,3,4-tetrazol-5-yl)phenylsulfanyl]isoquinoline 160 mg (0.5 mmol), concentrated sulfuric acid 1.6 ml and OXONE (trademark) 600 mg (1.0 mmol).

Melting point: 230–231° C.

Mass spectrometry (m/z): 372 (M+1)

Nuclear magnetic resonance spectrum (DMSO-$d_6$) δ: 9.61(1H,s), 8.88(1H,d), 8.79(1H,d), 8.68(1H,d), 8.62(1H,d), 8.35(1H,d), 8.24(1H,d), 8.15(1H,d), 8.06(1H,dd).

Infrared absorption spectrum $\nu_{max}$ (KBr) cm$^{-1}$: 1650, 1550, 1140, 1105.

Element anlysis values (calculated as $C_{16}H_{10}ClN_5O_2S \cdot 1/2H_2SO_4 \cdot 1/2H_2O$)

|  | C(%) | H(%) | N(%) | S(%) |
| --- | --- | --- | --- | --- |
| Theoretical values | 44.71 | 2.81 | 16.29 | 11.12 |
| Found values | 44.71 | 2.77 | 16.36 | 11.12 |

EXAMPLE 28

4-(5-Isoquinolylsulfanyl)-5-nitro-1,2-benzenediamine

According to the method in Example 10, 4-(5-isoquinolylsulfanyl)-5-nitro-1,2-benzenediamine 980 mg (53.5%) was obtained from 5-isoquinolinethiol 1.41 g (8.8 mmol), DMF 5 ml, potassium carbonate 2.42 g (17.5 mmol) and 4-fluoro-5-nitro-1,2-benzenediamine 1.00 g (5.8 mmol).

Melting point: 253–255° C.

Mass spectrometry (m/z): 313 (M+1)

Nuclear magnetic resonance spectrum (DMSO-$d_6$) δ: 9.43(1H,s), 8.53(1H,d), 8.33(1H,d), 8.15(1H,d), 7.85(1H,d), 7.80(1H,dd), 7.49(1H,s), 5.92(2H,s), 5.52(1H,s), 5.00(2H,s).

Infrared absorption spectrum $\nu_{max}$ (KBr) cm$^{-1}$: 3430, 1510, 1260.

Element anlysis values (calculated as $C_{15}H_{12}N_4O_2S$)

|  | C(%) | H(%) | N(%) | S(%) |
| --- | --- | --- | --- | --- |
| Theoretical values | 57.68 | 3.87 | 17.97 | 10.27 |
| Found values | 57.33 | 3.74 | 17.82 | 10.07 |

EXAMPLE 29

5-(5-Isoquinolylsulfanyl)-2,4-dinitroaniline

According to the method in Example 10, 5-(5-isoquinolylsulfanyl)-2,4-dinitroaniline 4.22 g (96.1%) was obtained from 5-isoquinolinethiol 2.28 g (14.1 mmol), DMF 30 ml, potassium carbonate 3.90 g (28.2 mmol) and 2,4-dinitro-5-fluoroaniline 2.58 g (12.8 mmol).

Melting point: >270° C.

Mass spectrometry (m/z): 343 (M+1)

Nuclear magnetic resonance spectrum (DMSO-$d_6$) δ: 9.49(1H,s), 8.94(1H,s), 8.56(1H,d), 8.44(1H,d), 7.84–7.90(4H,m), 5.93(1H,s).

Infrared absorption spectrum $\nu_{max}$ (KBr) cm$^{-1}$: 3450, 1620, 1560, 1300, 1260.

Element anlysis values (calculated as $C_{15}H_{14}N_4O_4S$)

|  | C(%) | H(%) | N(%) | S(%) |
| --- | --- | --- | --- | --- |
| Theoretical values | 52.63 | 2.94 | 16.37 | 9.37 |
| Found values | 52.61 | 2.88 | 16.57 | 9.16 |

EXAMPLE 30

N1-[4-(5-Isoquinolylsulfanyl)-2-methylcarboxamide-5-nitrophenyl]acetamide

According to the method in Example 1, N1-[4-(5-isoquinolylsulfanyl)-2-methylcarboxamide-5-nitrophenyl]acetamide 1.02 g (68.4%) was obtained from 5-benzoylsulfanylisoquinoline 1.00 g (3.8 mmol), sodium methoxide 500 mg (9.3 mmol) and N1(4-fluoro-2-methylcarboxamide-5-nitrophenyl)acetamide 960 mg (3.8 mmol).

Melting point: >270° C.

Mass spectrometry (m/z): 397 (M+1)

Nuclear magnetic resonance spectrum (DMSO-$d_6$) δ: 8.54(1H,s), 8.27(2H,d), 7.78(1H,s), 7.75(2H,d), 2.11(3H,s), 2.03(3H,s).

Infrared absorption spectrum $v_{max}$ (KBr) cm$^{-1}$: 3320, 1700, 1650, 1500, 1330, 1260.

Element anlysis values (calculated as $C_{15}H_{10}N_2O_2S$)

|  | C(%) | H(%) | N(%) |
| --- | --- | --- | --- |
| Theoretical values | 57.57 | 4.07 | 14.13 |
| Found values | 57.26 | 3.99 | 14.15 |

EXAMPLE 31

N1-[2-Ethylcarboxamido-4-(5-isoquinolylsulfanyl)-5-nitrophenyl]propanamide

According to the method in Example 10, N1-[2-ethylcarboxamide-4-(5-isoquinolylsulfanyl)-5-nitrophenyl]propanamide 450 mg (37.8%) was obtained from 5-isoquinolinethiol 500 mg (3.1 mmol), DMF 30 ml, potassium carbonate 1.17 g (8.5 mmol) and N1-(2-ethylcarboxamido-4-fluoro-5-nitrophenyl)propanamide 800 mg (2.8 mmol).

Melting point: 258–261° C.

Mass spectrometry (m/z): 425 (M+1)

Nuclear magnetic resonance spectrum (DMSO-$d_6$) δ: 9.44(1H,d), 8.54(1H,s), 8.51(1H,d), 8.38(1H,d), 8.23(1H,dd), 7.88(1H,d), 7.83(1H,dd), 7.21(1H,s), 2.36(2H,q), 2.14(2H,q), 1.07(3H,t), 0.81(3H,t).

Infrared absorption spectrum $v_{max}$ (KBr) cm$^{-1}$: 3300, 1710, 1660, 1535, 1500, 1320, 1270.

Element anlysis values (calculated as $C_{21}H_2ON_4O_4S$)

|  | C(%) | H(%) | N(%) |
| --- | --- | --- | --- |
| Theoretical values | 59.42 | 4.75 | 13.20 |
| Found values | 59.59 | 4.73 | 13.14 |

EXAMPLE 32

N1-[2-Amino-4-(5-isoquinolylsulfanyl)-5-nitrophenyl]butanamide

5-Isoquinolinethiol 500 mg (3.1 mmol) was dissolved in DMF 20 ml, potassium carbonate 1.29 g (9.3 mmol) and N1-(2-amino-4-fluoro-5-nitrophenyl)butane amide 750 mg (3.1 mmol) were added, and the mixture was heated with stirring at 90° C. for 6 hours. The reaction mixture was concentrated under reduced pressure, ethyl acetate-ether was added to the resulting residue to crystallize. The crystals were collected and washed with methanol to obtain N1-[2-amino-4-(5-isoquinolylsulfanyl)-5-nitrophenyl]butanamide 150 mg (12.9%).

Melting point: 191–192° C.

Mass spectrometry (m/z): 383 (M+1)

Nuclear magnetic resonance spectrum (DMSO-$d_6$) δ: 9.46(1H,s), 8.55(1H,d), 8.45(1H,s), 8.39(1H,d), 8.22(1H,d), 7.88(1H,d), 7.83(1H,dd), 5.63(1H,s), 2.26(2H,t), 1.57(2H,m), 0.88(3H,t).

Infrared absorption spectrum $v_{max}$ (KBr) cm$^{-1}$: 1650, 1510, 1300.

EXAMPLE 33

N1-[2-Amino-4-(5-isoquinolylsulfanyl)-5-nitrophenyl]-2-methylpropanamide

5-Isoquinolinethiol 500 mg (3.1 mmol) was dissolved in DMF 20 ml, potassium carbonate 1.29 g (9.3 mmol) and N1-(2-amino-4-fluoro-5-nitrophenyl)-2-methylpropane amide) 750 mg (3.1 mmol) were added, and the mixture was heated with stirring at 100° C. for 1 hour. The reaction mixture was concentrated under reduced pressure, ether was added to the resulting residue to crystallize. The crystals were collected and washed with methanol to obtain N1-[2-amino-4-(5-isoquinolylsulfanyl)-5-nitrophenyl]-2-methylpropanamide 380 mg (31.0%).

Melting point: 219–221° C.

Mass spectrometry (m/z): 383 (M+1)

Nuclear magnetic resonance spectrum (DMSO-$d_6$) δ: 9.46(1H,s), 8.55(1H,d), 8.45(1H,s), 8.39(1H,d), 8.22(1H,d), 7.82–7.87(2H,m), 5.65(1H,s), 2.57–2.60(1H,m), 1.08(3H,s), 1.07(3H,s).

Infrared absorption spectrum $v_{max}$ (KBr) cm$^{-1}$: 3440, 1640, 1600, 1510, 1300, 1280.

Element anlysis values (calculated as $C_{19}H_{18}N_4O_3S$)

|  | C(%) | H(%) | N(%) | S(%) |
| --- | --- | --- | --- | --- |
| Theoretical values | 57.64 | 4.96 | 14.14 | 8.10 |
| Found values | 57.44 | 4.58 | 13.79 | 8.22 |

EXAMPLE 34

4-Fluoro-5-(5-isoquinolylsulfanyl)-2-nitroaniline

5-Isoquinolinethiol 1.00 g (6.2 mmol) was dissolved in DMF 25 ml, potassium carbonate 1.60 g (11.6 mmol) and 4,5-difluoro-2-nitroaniline 1.00 g (5.5 mmol) were added, and the mixture was stirred at room temperature for 2 hours. The reaction solution was poured into ice water, and the resulting precipitates were collected and washed with water to give 4-fluoro-5-(5-isoquinolylsulfanyl)-2-nitroaniline 1.95 g (quantitative).

Melting point: 217–220° C.

Mass spectrometry (m/z): 316 (M+1)

Nuclear magnetic resonance spectrum (DMSO-$d_6$) δ: 9.48(1H,s), 8.61(1H,d), 8.41(1H,s), 8.21(1H,d), 7.93(1H,d), 7.79–7.85(2H,m), 7.20(2H,s), 6.06(1H,s).

Infrared absorption spectrum $v_{max}$ (KBr) cm$^{-1}$: 3460, 3300, 3150, 1620, 1580, 1490, 1330, 1240, 1200.

Element anlysis values (calculated as $C_{15}H_{10}N_3O_2SF$)

|  | C(%) | H(%) | N(%) | S(%) |
| --- | --- | --- | --- | --- |
| Theoretical values | 57.34 | 3.20 | 13.33 | 10.17 |
| Found values | 57.09 | 3.40 | 13.62 | 9.87 |

EXAMPLE 35

4-Fluoro-5-(5-isoquinolylsulfanyl)-1,2-benzenediamine

4-Fluoro-5-(5-isoquinolylsulfanyl)-2-nitroaniline 1.60 g (5.1 mmol) was dissolved in concentrated hydrochloric acid 30 ml, stannous chloride dihydrate 4.10 g (18.2 mmol) was added, and the mixture was stirred for 2 hours at room temperature. After 50% sodium hydroxide was added, the resulting alkaline solution was extracted with ethyl acetate. The organic layer was washed with water and saturated sodium chloride, dried over anhydrous sodium sulfate, and concentrated under reduced pressure. The resulting residue was recrystallized from ethyl acetate-n-hexane to obtain 4-fluoro-5-(5-isoquinolylsulfanyl)-1,2-benzenediamine 1.00 g (69.1%).

Melting point: 185–187° C.

Mass spectrometry (m/z): 286 (M+1)

Nuclear magnetic resonance spectrum (DMSO-$d_6$) δ: 9.32(1H,s), 8.57(1H,d), 8.01(1H,d), 7.91(1H,d), 7.54(1H, dd), 7.21(1H,d), 6.65(1H,d), 6.48(1H,d), 5.27(2H,brs), 4.52 (2H,brs).

Infrared absorption spectrum $v_{max}$ (KBr) cm$^{-1}$: 1620, 1510, 1260, 820.

Element anlysis values (calculated as $C_{15}H_{12}FN_3S.1/8H_2O$)

|  | C(%) | H(%) | N(%) | S(%) |
| --- | --- | --- | --- | --- |
| Theoretical values | 62.64 | 4.29 | 14.61 | 11.15 |
| Found values | 62.33 | 4.41 | 14.72 | 10.77 |

EXAMPLE 36

4-Chloro-5-(5-isoquinolylsulfanyl)-2-nitroaniline

5-Isoquinolinethiol 500 mg (3.1 mmol) was dissolved in DMF 15 ml, potassium carbonate 830 mg (6.0 mmol) and 4,5-dichloro-2-nitroaniline 620 mg (3.0 mmol) were added, and the mixture was stirred at room temperature for 1.5 hours. The reaction mixture was poured into ice water, and the resulting precipitates were collected and washed with water to give 4-chloro-5-(5-isoquinolylsulfanyl)-2-nitroaniline 980 mg (98.4%).

Melting point: >270° C.

Mass spectrometry (m/z): 332 (M+1)

Nuclear magnetic resonance spectrum (DMSO-$d_6$) δ: 9.49(1H,s), 8.60(1H,d), 8.43(1H,s), 8.22(1H,d), 8.03(1H,d), 7.85–7.87(2H,m), 7.28(2H,brs), 5.95(1H,s).

Infrared absorption spectrum $v_{max}$ (KBr) cm$^{-1}$: 3450, 1620, 1480, 1260, 1240.

Element anlysis values (calculated as $C_{15}H_{10}N_3O_2SCl$)

|  | C(%) | H(%) | N(%) | S(%) |
| --- | --- | --- | --- | --- |
| Theoretical values | 54.30 | 3.04 | 12.67 | 9.66 |
| Found values | 54.10 | 3.00 | 12.39 | 9.86 |

EXAMPLE 37

4-Chloro-5-(5-isoquinolylsulfanyl)-1,2-benzenediamine

4-Chloro-5-(5-isoquinolylsulfanyl)-2-nitroaniline 1.78 g (5.4 mmol) was dissolved in concentrated hydrochloric acid 30 ml, stannous chloride dihydrate 4.30 g (19.1 mmol) was added, and the mixture was stirred overnight at room temperature. The reaction mixture was poured into water, 50% sodium hydroxide was added to alkalize the mixture, and the mixture was extracted with ethyl acetate. The organic layer was washed with water and with saturated sodium chloride, dried over anhydrous sodium sulfate, and concentrated under reduced pressure. The resulting residue was recrystallized from ethyl acetate-n-hexane to give 4-chloro-5-(5-isoquinolylsulfanyl)-1,2-benzenediamine 1.45 g (89.5%).

Melting point: 200–203° C.

Mass spectrometry (m/z): 302 (M+1)

Nuclear magnetic resonance spectrum (DMSO-$d_6$) δ: 9.28(1H,s), 8.53(1H,dd), 7.95(1H,dd), 7.89(1H,dd), 7.35 (1H,dd), 7.17(1H,dd), 6.70(1H,dd), 6.65(1H,dd), 5.14(2H, s), 4.74(2H,s).

Infrared absorption spectrum $v_{max}$ (KBr) cm$^{-1}$: 1620, 1560, 1480, 1300, 1280, 1260, 820, 760.

Element anlysis values (calculated as $C_{15}H_{12}ClN_3S$)

|  | C(%) | H(%) | N(%) | S(%) |
| --- | --- | --- | --- | --- |
| Theoretical values | 59.70 | 4.01 | 13.92 | 10.62 |
| Found values | 59.45 | 4.21 | 13.96 | 10.52 |

EXAMPLE 38

4-Chloro-5-(5-isoquinolylsulfonyl)-2-nitroaniline

According to the method in method (b) of Example 7, 4-chloro-5-(5-isoquinolylsulfonyl)-2-nitroaniline 750 mg (68.1%) was obtained from 4-chloro-5-(5-isoquinolylsulfanyl)-2-nitroaniline 1.00 g (3.0 mmol), concentrated sulfuric acid 10 ml and OXONE (trademark) 3.71 g (6.0 mmol).

Melting point: >270° C.

Mass spectrometry (m/z): 364 (M+1)

Nuclear magnetic resonance spectrum (DMSO-$d_6$) δ: 9.52(1H,s), 8.73(1H,d), 8.65(1H,dd), 8.61(1H,d), 8.32(1H, s), 8.07(1H,d), 7.98(1H,s), 7.98(1H,dd), 7.90(2H,s).

Infrared absorption spectrum $v_{max}$ (KBr) cm$^{-1}$: 3480, 3380, 1630, 1260, 1160.

EXAMPLE 39

4-Chloro-5-(5-isoquinolylsulfonyl)-1,2-benzenediamine

According to the method in Example 3, 4-Chloro-5-(5-isoquinolylsulfonyl)-1,2-benzenediamine 230 mg (35.3%) was obtained from 4-chloro-5-(5-isoquinolylsulfonyl)-2-nitroaniline 720 mg (2.0 mmol), concentrated hydrochloric acid 20 ml, and stannous chloride dihydrate 2.24 g (9.9 mmol).

Melting point: 255–256° C.

Mass spectrometry (m/z): 334 (M+1)

Nuclear magnetic resonance spectrum (DMSO-$d_6$) δ: 9.45(1H,s), 8.58(1H,d), 8.57(1H,d), 8.13(1H,d), 7.89(1H, dd), 7.62(1H,s), 6.47(1H,s), 5.76(2H,s), 5.16(2H,s).

Infrared absorption spectrum $v_{max}$ (KBr) cm$^{-1}$: 3480, 3380, 1630, 1560, 1300, 1140, 580.

Element anlysis values (calculated as $C_{15}H_{12}N_3O_2SCl$)

|  | C(%) | H(%) | N(%) | S(%) |
| --- | --- | --- | --- | --- |
| Theoretical values | 53.97 | 3.62 | 12.59 | 9.61 |
| Found values | 54.34 | 3.45 | 12.16 | 10.01 |

EXAMPLE 40

4-(5-Isoquinolylsulfanyl)-5-methyl-2-nitroaniline

According to the method in Example 10, 4-(5-isoquinolylsulfanyl)-5-methyl-2-nitroaniline 3.54 g (quantitative) was obtained from 5-isoquinolinethiol 2.00 g (12.4 mmol), DMF 50 ml, potassium carbonate 3.30 g (23.9 mmol) and 5-chloro-4-methyl-2-nitroaniline 2.10 g (11.3 mmol).

Melting point: 242–244° C.

Mass spectrometry (m/z): 312 (M+1)

Nuclear magnetic resonance spectrum (DMSO-$d_6$) δ: 9.46(1H,s), 8.58(1H,d), 8.36(1H,d), 8.13(1H,d), 7.88(1H,d), 7.83(1H,s), 7.80(1H,d), 7.07(2H,s), 5.98(1H,s).

Infrared absorption spectrum $v_{max}$ (KBr) cm$^{-1}$: 3450, 1620, 1480, 1240.

Element anlysis values (calculated as $C_{16}H_{13}N_3O_2S$)

|  | C(%) | H(%) | N(%) | S(%) |
| --- | --- | --- | --- | --- |
| Theoretical values | 61.72 | 4.21 | 13.50 | 10.30 |
| Found values | 61.97 | 4.09 | 13.53 | 10.30 |

EXAMPLE 41

4-(5-Isoquinolylsulfanyl)-5-methyl-1,2-benzene diamine

According to the method in Example 3, 4-(5-isoquinolylsulfanyl)-5-methyl-1,2-benzene diamine 1.78 g (56.3%) was obtained from 4-(5-isoquinolylsulfanyl)-5-methyl-2-nitroaniline 3.50 g (11.2 mmol), concentrated hydrochloric acid 80 ml, and stannous chloride dihydrate 8.90 g (39.3 mmol).

Melting point: 214–217° C.

Mass spectrometry (m/z): 282 (M+1)

Nuclear magnetic resonance spectrum (DMSO-$d_6$) δ: 9.30(1H,s), 8.56(1H,d), 7.98(1H,d), 7.84(1H,d), 7.49(1H,dd), 6.97(1H,d), 6.71(1H,s), 6.56(1H,s), 4.86(2H,s), 4.48(2H,s), 2.07(3H,s).

Infrared absorption spectrum $v_{max}$ (KBr) cm$^{-1}$: 3430, 3350, 3200, 1570, 1500, 820.

Element anlysis values (calculated as $C_{16}H_{15}N_3S$)

|  | C(%) | H(%) | N(%) | S(%) |
| --- | --- | --- | --- | --- |
| Theoretical values | 68.30 | 5.37 | 14.93 | 11.40 |
| Found values | 68.61 | 5.37 | 14.86 | 11.09 |

EXAMPLE 42

5(6)-(5-Isoquinolylsulfanyl)-1H-benzo[d]imidazole 4-(5-Isoquinolylsulfanyl)-1,2-benzenediamine 850 mg (3.2 mmol) was dissolved in 4N hydrochloric acid 20 ml, ethyl formate 0.6 ml was added, and the mixture was heated and refluxed for 2 hours. The reaction mixture was neutralized with a saturated sodium bicarbonate solution, the resulting precipitates were collected and washed with water, and 5(6)-(5-isoquinolylsulfanyl)-1H-benzo[d]imidazole 740 mg (83.4%) was obtained.

Melting point: 201–203° C.

Mass spectrometry (m/z): 278 (M+1)

Nuclear magnetic resonance spectrum (DMSO-$d_6$) δ: 9.35(1H,s), 8.56(1H,d), 8.27(1H,s), 8.07–8.05(2H,m), 7.63–7.56(4H,m), 7.25(1H,dd).

Infrared absorption spectrum $v_{max}$ (KBr) cm$^{-1}$: 1610, 1475, 1410, 1280, 1260, 960, 815.

Element anlysis values (calculated as $C_{16}H_{11}N_3S.1/2H_2O$)

|  | C(%) | H(%) | N(%) | S(%) |
| --- | --- | --- | --- | --- |
| Theoretical values | 67.11 | 4.22 | 14.67 | 11.20 |
| Found values | 67.13 | 4.07 | 14.57 | 11.14 |

EXAMPLE 43

5(6)-(5-Isoquinolylsulfonyl)-1H-benzo[d]imidazole

5(6)-(5-Isoquinolylsulfanyl)-1H-benzo[d]imidazole 500 mg (1.8 mmol) was dissolved in concentrated sulfuric acid 5.0 ml, Beckmann's reagent 10.0 ml ($K_2Cr_2O_7$ 1 g, $H_2SO_4$ 1 ml, $H_2O$ 9 ml) was added dropwise, and the mixture was stirred overnight at room temperature. After water was added to the reaction solution, the solution was neutralized with sodium hydroxide and sodium bicarbonate, the resulting precipitates were collected and washed, and 5(6)-(5-isoquinolylsulfonyl)-1H-benzo[d]imidazole 300 mg (57.5%) was obtained.

Melting point: 151–154° C.

Mass spectrometry (m/z): 310 (M+1)

Nuclear magnetic resonance spectrum (DMSO-$d_6$) δ: 9.67(1H,s), 9.24(1H,s), 8.85(1H,d), 8.69(1H,d), 8.65(1H,d), 8.59(1H,d), 8.48(1H,dd), 8.06(1H,t), 7.99(1H,dd), 7.92(1H,d).

Infrared absorption spectrum $v_{max}$ (KBr) cm$^{-1}$: 1610, 1485, 1410, 1360, 1290, 1265, 1135, 1120, 1040, 820, 720, 640, 560.

Element anlysis values (calculated as $C_{16}H_{11}N_3SO_2.3/2H_2O$)

|  | C(%) | H(%) | N(%) |
| --- | --- | --- | --- |
| Theoretical values | 51.51 | 3.65 | 11.26 |
| Found values | 51.27 | 3.60 | 10.87 |

EXAMPLE 44

6(5)-Chloro-5(6)-(5-isoquinolylsulfanyl)-1H-benzo[d]imidazole

4-Chloro-5-(5-isoquinolylsulfanyl)-1,2-benzene diamine 700 mg (2.3 mmol) was dissolved in 4N hydrochloric acid 10 ml, ethyl formate 0.75 ml was added, and the mixture was heated and refluxed overnight. The solution was neutralized with aqueous 40% sodium hydroxide solution and saturated sodium bicarbonate, and extracted with ethyl acetate. The organic layer was washed with water and with sodium chloride, dried over anhydrous sodium sulfate, and concentrated under reduced pressure. The resulting precipitates were crystallized with ethyl acetate-hexane to give 6(5)-chloro-5(6)-(5-isoquinolylsulfanyl)-1H-benzo[d]imidazole 630 mg (87.0%).

Melting point: 232–235° C.

Mass spectrometry (m/z): 312 (M+1)

Nuclear magnetic resonance spectrum (DMSO-$d_6$) δ: 9.40(1H,s), 8.57(1H,d), 8.25(1H,s), 8.17(1H,d), 8.00(1H,d), 7.86(1H,s), 7.68(1H,s), 7.67(1H,d), 7.25(1H,s).

Infrared absorption spectrum $v_{max}$ (KBr) cm$^{-1}$: 3050, 1450, 820.

Element anlysis values (calculated as $C_{16}H_{10}ClN_3S.1/8H_2O$)

| | C(%) | H(%) | N(%) | S(%) |
|---|---|---|---|---|
| Theoretical values | 61.19 | 3.29 | 13.38 | 10.21 |
| Found values | 61.13 | 3.24 | 13.46 | 10.34 |

EXAMPLE 45

6(5)-Chloro-5(6)-(5-isoquinolylsulfonyl)-1H-benzo[d]imidazole

6(5)-Chloro-5(6)-(5-isoquinolylsulfanyl)-1H-benzo[d]imidazole 320 mg (1.0 mmol) was dissolved in concentrated sulfuric acid 2.5 ml, Beckmann's reagent ($K_2Cr_2O_7$ 1 g, $H_2SO_4$ 1 ml, $H_2O$ 9 ml) 4.5 ml was added dropwise, and the mixture was stirred overnight at room temperature. The solution was neutralized with 4N sodium hydroxide and extracted with ethyl acetate. The organic layer was washed with water and with saturated sodium chloride, dried over anhydrous sodium sulfate, and concentrated under reduced pressure. The resulting residue was crystallized with ethyl acetate-hexane to give 6(5)-chloro-5(6)-(5-isoquinolylsulfonyl)-1H-benzo[d]imidazole 251 mg (70.9%).

Melting point: 250–253° C.

Mass spectrometry (m/z): 344 (M+1)

Nuclear magnetic resonance spectrum (DMSO-$d_6$) δ: 9.46(1H,s), 8.82(1H,s), 8.73(1H,d), 8.53–8.56(3H,m), 8.12(1H,d), 7.96(1H,dd), 7.77(1H,s).

Infrared absorption spectrum $v_{max}$ (KBr) cm$^{-1}$: 3350, 1620, 1370, 1320, 1310, 1130, 590, 580.

Element anlysis values (calculated as $C_{16}H_{10}ClN_3O_2S$)

| | C(%) | H(%) | N(%) | S(%) |
|---|---|---|---|---|
| Theoretical values | 55.87 | 2.93 | 12.22 | 9.33 |
| Found values | 55.91 | 3.07 | 12.06 | 9.38 |

EXAMPLE 46

5(6)-(5-Isoquinolylsulfanyl)-4-(7)-nitro-1H-benzo[d]imidazole

5-Isoquinolinethiol 250 mg (1.6 mmol) was dissolved in DMF 10 ml, 5(6)-chloro-4-(7)-nitro-1H-benzo[d]imidazole 380 mg (1.6 mmol) and potassium carbonate 860 mg (6.2 mmol) were added, and the mixture was stirred at a temperature of 130° C. for 5 hours. The reaction mixture was concentrated under reduced pressure, and the resulting residue was crystallized with ethyl acetate, 5(6)-(5-isoquinolylsulfanyl)-4-(7)-nitro-1H-benzo[d]imidazole 480 mg (96.7%) was obtained.

Melting point: >270° C.

Mass spectrometry (m/z): 323 (M+1)

Nuclear magnetic resonance spectrum (DMSO-$d_6$) δ: 9.35(1H,s), 8.53(1H,d), 8.06(1H,d), 7.96(1H,d), 7.94(1H,s), 7.61(1H,dd), 7.53–7.55(2H,m), 6.08(1H,d).

Infrared absorption spectrum $v_{max}$ (KBr) cm$^{-1}$: 1470, 1340, 1310, 1280, 1200, 1180.

EXAMPLE 47

5(6)-(5-Isoquinolylsulfonyl)-4-(7)-nitro-1H-benzo[d]imidazole

5(6)-(5-Isoquinolylsulfanyl)-4-(7)-nitro-1H-benzo[d]imidazole 200 mg (0.6 mmol) was dissolved in concentrated sulfuric acid 1.5 ml, Beckmann's reagent 3 ml ($K_2Cr_2O_7$ 1 g, $H_2SO_4$ 1 ml, $H_2O$ 9 ml) was added dropwise, and the mixture was stirred overnight at room temperature. The solution was neutralized with a aqueous 4N sodium hydroxide solution, and the resulting precipitates were collected and washed with water and with ether, and 5(6)-(5-isoquinolylsulfonyl)-4-(7)-nitro-1H-benzo[d]imidazole 130 mg (58.3%) was obtained.

Melting point: >270° C.

Mass spectrometry (m/z): 355 (M+1)

Nuclear magnetic resonance spectrum (DMSO-$d_6$) δ: 9.49(1H,s), 8.66(1H,d), 8.57(1H,s), 8.55(1H,d), 8.32(1H,d), 7.95–8.02(3H,m).

Infrared absorption spectrum $v_{max}$ (KBr) cm$^{-1}$: 1620, 1540, 1320, 1120.

EXAMPLE 48

5(6)-(5-Isoquinolylsulfanyl)-2-methyl-1H-benzo[d]imidazole

The title compound of 5(6)-(5-isoquinolylsulfanyl)-2-methyl-1H-benzo[d]imidazole was synthesized by using the following methods (a) and (b).

(a) method 4-(5-isoquinolylsulfanyl)-1,2-benzenediamine 510 mg (1.91 mmol) was dissolved in 4N hydrochloric acid 20 ml, acetic acid 0.2 ml was added, and the mixture was heated and refluxed for 5 hours. Further, the solution was stirred overnight at room temperature, the reaction solution was neutralized with ammonia water solution. The precipitates were collected and washed with water, and 5(6)-(5-isoquinolylsulfanyl)-2-methyl-1H-benzo[d]imidazole 450 mg (80.9%) was obtained.

Melting point: 226–229° C.

Mass spectrometry (m/z): 292 (M+1)

Nuclear magnetic resonance spectrum (DMSO-$d_6$) δ: 9.36(1H,s), 8.57(1H,d), 8.07–8.05(2H,m), 7.60(1H,t), 7.53–7.50(3H,m), 7.21(1H,dd), 2.50(3H,s).

Infrared absorption spectrum $v_{max}$ (KBr) cm$^{-1}$: 1615, 1580, 1540, 1450, 1380, 1260, 820, 810.

Element anlysis values (calculated as $C_{17}H_{13}N_3S \cdot 1/4H_2O$)

| | C(%) | H(%) | N(%) | S(%) |
|---|---|---|---|---|
| Theoretical values | 69.01 | 4.60 | 14.20 | 10.84 |
| Found values | 68.81 | 4.79 | 14.56 | 10.64 |

(b) method 5-(5-Isoquinolylsulfanyl)-2-nitroaniline 9.20 g (30.9 mmol) was dissolved in concentrated hydrochloric acid 120 ml, and stannous chloride dihydrate 30.20 g (133.8 mmol) and acetic acid 6 ml were added, and the mixture was heated with stirred at 130° C. for 4.5 hours. After the reaction solution was cooled, the precipitates were collected and washed with a little water, 5(6)-(5-isoquinolylsulfanyl)-2-methyl-1H-benzo[d]imidazole hydrochloride was quantitatively obtained.

Nuclear magnetic resonance spectrum (DMSO-$d_6$) δ: 9.80(1H,s), 8.67(1H,d), 8.45(1H,d), 8.43(1H,d), 8.08(1H,d), 7.90(1H,t), 7.75(1H,d), 7.71(1H,d), 7.45(1H,dd), 2.76(3H,s).

EXAMPLE 49

5(6)-(5-Isoquinolylsulfonyl)-2-methyl-1H-benzo[d]imidazole

5(6)-(5-Isoquinolylsulfanyl)-2-methyl-1H-benzo[d]imidazole 300 mg (1.0 mmol) was dissolved in concentrated sulfuric acid 3.0 ml, Beckmann's reagent 6.0 ml (K$_2$Cr$_2$O$_7$ 1 g, H$_2$SO$_4$ 1 ml, H$_2$O 9 ml) was added dropwise, and the mixture was stirred for 3 hours at room temperature. After adding water, the reaction solution was neutralized with sodium hydroxide and with sodium bicarbonate. The resulting precipitates were collected and washed with water. The resulting residue was dissolved in methanol, and a methanol solution of saturated hydrochloric acid was added. The solution was concentrated under reduced pressure, the residue was recrystallized with acetone, and 5(6)-(5-isoquinolylsulfonyl)-2-methyl-1H-benzo[d]imidazole hydrochloride 200 mg (54.0%) was obtained.

Melting point: 239–244° C.

Mass spectrometry (m/z): 324 (M+1)

Nuclear magnetic resonance spectrum (DMSO-d$_6$) δ: 9.68(1H,s), 8.86(1H,dd), 8.69(1H,d), 8.67(1H,d), 8.57(1H,d), 8.44(1H,d), 8.08–8.02(2H,m), 7.90(1H,d), 2.78(3H,s).

Infrared absorption spectrum ν$_{max}$ (KBr) cm$^{-1}$: 1650, 1620, 1605, 1585, 1320, 1220, 1135, 815, 720, 620, 500.

Element anlysis values (calculated as C$_{17}$H$_{13}$N$_3$O$_2$S.4HCl.H$_2$O)

|  | C(%) | H(%) | N(%) |
| --- | --- | --- | --- |
| Theoretical values | 41.91 | 3.93 | 8.62 |
| Found values | 42.03 | 3.92 | 8.46 |

EXAMPLE 50

5(6)-(5-Isoquinolylsulfanyl)-2-methyl-6(5)-nitro-1H-benzo[d]imidazole

N1-[4-(5-Isoquinolylsulfanyl)-2-methylcarboxamide-5-nitrophenyl]acetamide 700 mg (1.8 mmol) was dissolved in concentrated hydrochloric acid 7 ml. After heating and refluxed for 20 hours, the reaction solution was concentrated under reduced pressure, and 5(6)-(5-isoquinolylsulfanyl)-2-methyl-6(5)-nitro-1H-benzo[d]imidazole hydrochloride 810 mg (quantitative) was obtained.

Melting point: 265–270° C.

Mass spectrometry (m/z): 337 (M+1)

Nuclear magnetic resonance spectrum (DMSO-d$_6$) δ: 9.89(1H,s), 8.66(1H,d), 8.61–8.60(1H,m), 8.50(1H,d), 8.31(1H,d), 8.06(1H,t), 6.68(1H,s), 2.57(3H,s).

Infrared absorption spectrum ν$_{max}$ (KBr) cm$^{-1}$: 3450, 1650, 1530, 1450, 1320, 825.

Element anlysis values (calculated as C$_{17}$H$_{10}$N$_4$O$_2$S.3HCl.1/2H$_2$O)

|  | C(%) | H(%) | N(%) | S(%) |
| --- | --- | --- | --- | --- |
| Theoretical values | 44.90 | 3.55 | 12.32 | 7.05 |
| Found values | 45.01 | 3.53 | 12.01 | 6.57 |

EXAMPLE 51

5(6)-(5-Isoquinolylsulfinyl)-2-methyl-6(5)-nitro-1H-benzo[d]imidazole

5(6)-(5-Isoquinolylsulfanyl)-2-methyl-6(5)-nitro-1H-benzo[d]imidazole 1.02 g (3.0 mmol) was dissolved in 10% sulfuric acid 10 ml, Beckmann's agent 20 ml (K$_2$Cr$_2$O$_7$ 1 g, H$_2$SO$_4$ 1 ml, H$_2$O 9 ml) was added dropwise, and the mixture was stirred overnight at room temperature. After adding water, the resulting precipitates were collected and washed with water. 5(6)-(5-Isoquinolylsulfinyl)-2-methyl-6(5)-nitro-1H-benzo[d]imidazole sulfate 300 mg (22.2%) was obtained.

Melting point: 184–188° C.

Mass spectrometry (m/z): 353 (M+1)

Nuclear magnetic resonance spectrum (DMSO-d$_6$) δ: 9.46(1H,s), 8.77(1H,d), 8.65(1H,d), 8.55(1H,s), 8.49(1H,s), 8.28(1H,d), 7.61(1H,t), 7.50(1H,d), 2.67(3H,s).

Infrared absorption spectrum ν$_{max}$ (KBr) cm$^{-1}$: 1620, 1520, 1320, 1040, 1030, 830.

Element anlysis values (calculated as C$_{17}$H$_{12}$N$_4$SO$_3$.1/4H$_2$SO$_4$)

|  | C(%) | H(%) | N(%) | S(%) |
| --- | --- | --- | --- | --- |
| Theoretical values | 54.18 | 3.34 | 14.87 | 10.63 |
| Found values | 54.36 | 3.39 | 14.81 | 10.68 |

EXAMPLE 52

5(6)-(5-Isoquinolylsulfonyl)-2-methyl-6(5)-nitro-1H-benzo[d]imidazole and 5(6)-(5-isoquinolylsulfonyl)-2-methyl-7(4)-nitro-1H-benzo[d]imidazole 5(6)-(5-Isoquinolylsulfonyl)-2-methyl-6(5)-nitro-1H-benzo[d]imidazole was synthesized by the following two methods (a) and (b), and 5(6)-(5-isoquinolylsulfonyl)-2-methyl-7(4)-nitro-1H-benzo[d]imidazole was synthesized by the following method (b).

(a) method

Oxidation of 5(6)-(5-isoquinolylsulfanyl)-2-methyl-6(5)-nitro-1H-benzo[d]imidazole 5(6)-(5-Isoquinolylsulfanyl)-2-methyl-6(5)-nitro-1H-benzo[d]imidazole 300 mg (0.9 mmol) was dissolved in concentrated sulfuric acid 2.5 ml, Beckmann's reagent 4.5 ml (K$_2$Cr$_2$O$_7$ 1 g, H$_2$SO$_4$ 1 ml, H$_2$O 9 ml) was added dropwise, and the mixture was stirred overnight at room temperature. After adding water, the mixture solution was neutralized with 4N sodium hydroxide, and the resulting precipitates were filtered and washed with water. The resulting residue was dissolved in methanol, and methanol saturated with hydrogen chloride was added. The solution was concentrated under reduced pressure, the residue was crystallized from acetone, and 5(6)-(5-Isoquinolylsulfonyl)-2-methyl-6(5)-nitro-1H-benzo[d]imidazole hydrochloride 100 mg (23.9%) was obtained.

(b) method

Nitration of 5(6)-(5-isoquinolylsulfonyl)-2-methyl-1H-benzo[d]imidazole

5(6)-(5-Isoquinolylsulfonyl)-2-methyl-1H-benzo[d]imidazole 4.01 g (12.4 mmol) was dissolved in concentrated sulfuric acid 30 ml, fuming nitric acid 3 ml was added, and the mixture was stirred for 5 hours. Water was added to the reaction mixture, the mixture was neutralized with sodium hydroxide, and the resulting precipitates were collected and washed with water. The resulting residue was purified by silica gel column chromatography (methanol:ethyl acetate=1:9), and 5(6)-(5-Isoquinolylsulfonyl)-2-methyl-6(5)-nitro-1H-benzo[d]imidazole 1.84 g (40.3%), and 5(6)-(5-isoquinolylsulfonyl)-2-methyl-7(4)-nitro-1H-benzo[d]imidazole 400 mg (8.8%) were obtained. 5(6)-(5-isoquinolylsulfonyl)-2-methyl-6(5)-nitro-1H-benzo[d]imidazole was converted into a hydrochloride by (a) method, and 1.84 g of 5(6)-(5-isoquinolylsulfonyl)-2-methyl-6(5)-nitro-1H-benzo[d]imidazole hydrochloride was obtained.

5(6)-(5-isoquinolylsulfonyl)-2-methyl-6(5)-nitro-1H-benzo[d]imidazole hydrochloride Melting point: >270° C.

Mass spectrometry (m/z): 369 (M+1)

Nuclear magnetic resonance spectrum (DMSO-$d_6$) δ: 9.64(1H,s), 8.68(1H,d), 8.60(1H,s), 8.49(1H,dd), 8.44(1H,d), 8.29(1H,s), 7.99(1H,t), 2.63(3H,s).

Infrared absorption spectrum $\nu_{max}$ (KBr) cm$^{-1}$: 1550, 1350, 1140, 825, 725, 500.

Element anlysis values (calculated as $C_{17}H_{12}N_4O_4S \cdot HCl \cdot 1/2H_2O$)

|  | C(%) | H(%) | N(%) | S(%) |
|---|---|---|---|---|
| Theoretical values | 49.33 | 3.41 | 13.53 | 7.75 |
| Found values | 49.10 | 2.94 | 13.22 | 7.92 |

5(6)-(5-isoquinolylsulfonyl)-2-methyl-7(4)-nitro-1H-benzo[d]imidazole

Melting point: >270° C.

Mass spectrometry (m/z): 369 (M+1)

Nuclear magnetic resonance spectrum (DMSO-$d_6$) δ: 9.46(1H,s), 8.78(1H,d), 8.66(1H,d), 8.61(1H,s), 8.52(1H,d), 8.48(1H,d), 8.43(1H,d), 7.95(1H,dd), 2.59(3H,s).

Infrared absorption spectrum $\nu_{max}$ (KBr) cm$^{-1}$: 1520, 1340, 1320, 1130, 620, 580.

Element anlysis values (calculated as $C_{17}H_{12}N_4O_4S$)

|  | C(%) | H(%) | N(%) |
|---|---|---|---|
| Theoretical values | 55.43 | 3.28 | 8.70 |
| Found values | 55.76 | 3.68 | 8.90 |

EXAMPLE 53

5(6)-(5-Isoquinolylsulfonyl)-2-methyl-1H-benzo[d]imidazole-6(5)-amine

5(6)-(5-Isoquinolylsulfonyl)-2-methyl-6(5)-nitro-1H-benzo[d]imidazole 300 mg (0.8 mmol) was dissolved in concentrated hydrochloric acid 12 ml, stannous chloride dihydrate 900 mg (4.0 mmol) was added, and the mixture was stirred overnight at room temperature. 50% sodium hydroxide and saturated sodium bicarbonate were added to neutralize the reaction solution, and the solution was extracted with ethyl acetate. The organic layer was washed with saturated sodium chloride, dried over anhydrous sodium sulfate and concentrated under reduced pressure. The resulting residue was crystallized from ethyl acetate-hexane, and 5(6)-(5-isoquinolylsulfonyl)-2-methyl-1H-benzo[d]imidazole-6(5)-amine 115 mg (41.7%) was obtained.

Melting point: >270° C.

Mass spectrometry (m/z): 339 (M+1)

Nuclear magnetic resonance spectrum (DMSO-$d_6$) δ: 9.42(1H,s), 8.61(1H,d), 8.59(1H,d), 8.44(1H,d), 8.35(1H,d), 8.06(1H,s), 7.86(1H,dd), 6.74(1H,s), 5.60(2H,brs), 2.67(3H,s).

Infrared absorption spectrum $\nu_{max}$ (KBr) cm$^{-1}$: 3450, 3350, 1640, 1300, 1120, 610.

Element anlysis values (calculated as $C_{17}H_{14}N_4O_2S \cdot 5/4H_2O$)

|  | C(%) | H(%) | N(%) | S(%) |
|---|---|---|---|---|
| Theoretical values | 56.52 | 4.61 | 15.52 | 8.88 |
| Found values | 56.51 | 5.00 | 15.28 | 8.96 |

EXAMPLE 54

5(6)-(5-Isoquinolylsulfonyl)-2-methyl-1H-benzo[d]imidazole-7(4)-amine

5(6)-(5-Isoquinolylsulfonyl)-2-methyl-7(4)-nitro-1H-benzo[d]imidazole 50 mg (0.1 mmol) was dissolved in concentrated hydrochloric acid 2 ml, stannous chloride dihydrate 150 mg (0.7 mmol) was added, and the mixture was stirred overnight at room temperature. 50% sodium hydroxide and a saturated sodium bicarbonate were added to neutralize the reaction mixture, and the solution was extracted with ethyl acetate. The organic layer was washed with saturated sodium chloride, dried over anhydrous sodium sulfate and concentrated under reduced pressure. The resulting residue was crystallized from ethyl acetate, and 5(6)-(5-isoquinolylsulfonyl)-2-methyl-1H-benzo[d]imidazole-7(4)-amine 30 mg (65.3%) was obtained.

Melting point: 182–185° C.

Nuclear magnetic resonance spectrum (DMSO-$d_6$) δ: 9.44(1H,s), 8.61(1H,d), 8.56(1H,d), 8.47(1H,d), 8.36(1H,d), 7.91(1H,dd), 2.45(3H,s).

Infrared absorption spectrum $\nu_{max}$ (KBr) cm$^{-1}$: 3350, 3200, 1620, 1290, 1130, 630.

EXAMPLE 55

6(5)-Fluoro-5(6)-(5-isoquinolylsulfanyl)-2-methyl-1H-benzo[d]imidazole

4-Fluoro-5-(5-isoquinolylsulfanyl)-1,2-benzenediamine 600 mg (2.1 mmol) was dissolved in 4N hydrochloric acid 10 ml, acetic acid 0.5 ml was added, and the mixture was heated and refluxed overnight. 40% sodium hydroxide was added to neutralize the reaction solution, and the solution was extracted with ethyl acetate. The organic layer was dried over anhydrous sodium sulfate and concentrated under reduced pressure. The resulting residue was crystallized from methanol-ether-hexane, and 6(5)-fluoro-5(6)-(5-isoquinolylsulfanyl)-2-methyl-1H-benzo[d]imidazole 560 mg (85.3%) was obtained.

Melting point: 230–232° C.

Mass spectrometry (m/z): 310 (M+1)

Nuclear magnetic resonance spectrum (DMSO-$d_6$) δ: 9.39(1H,s), 8.62(1H,d), 8.11(1H,d), 8.07(1H,d), 7.61(1H,dd), 7.54(1H,d), 7.48(1H,d), 2.49(3H,s).

Infrared absorption spectrum $\nu_{max}$ (KBr) cm$^{-1}$: 1620, 1450, 1380, 810.

Element anlysis values (calculated as $C_{17}H_{12}FN_3S \cdot H_2O$)

|  | C(%) | H(%) | N(%) | S(%) |
|---|---|---|---|---|
| Theoretical values | 66.00 | 3.91 | 13.58 | 10.37 |
| Found values | 65.85 | 4.12 | 13.30 | 10.21 |

EXAMPLE 56

6(5)-Fluoro-5(6)-(5-isoquinolylsulfonyl)-2-methyl-1H-benzo[d]imidazole

6(5)-Fluoro-5(6)-(5-isoquinolylsulfanyl)-2-methyl-1H-benzo[d]imidazole 300 mg (1.0 mmol) was dissolved in concentrated sulfuric acid 2.5 ml, Beckmann's reagent (K$_2$Cr$_2$O$_7$ 1 g, H$_2$SO$_4$ 1 ml, H$_2$O 9 ml) 3.5 ml was added dropwise, and the mixture was stirred overnight at room temperature. The reaction mixture was neutralized with 50% sodium hydroxide, and extracted with ethyl acetate. The organic layer was washed with water and with saturated sodium chloride, dried over anhydrous sodium sulfate and concentrated under reduced pressure. The resulting residue was crystallized from ethyl acetate-hexane, and 6(5)-fluoro-5(6)-(5-isoquinolylsulfonyl)-2-methyl-1H-benzo[d]imidazole 160 mg (47.1%) was obtained.

Melting point: >270° C.

Mass spectrometry (m/z): 342 (M+1)

Nuclear magnetic resonance spectrum (DMSO-d$_6$) δ: 9.46(1H,s), 8.69(1H,d), 8.59(1H,d), 8.53(1H,d), 8.38(1H,d), 8.23(1H,d), 7.96(1H,dd), 7.38(1H,d), 2.49(3H,s).

Infrared absorption spectrum $v_{max}$ (KBr) cm$^{-1}$: 1620, 1315, 1040, 720, 585, 500.

Element anlysis values (calculated as C$_{17}$H$_{12}$FN$_3$O$_2$S.1/4H$_2$O)

|  | C(%) | H(%) | N(%) | S(%) |
| --- | --- | --- | --- | --- |
| Theoretical values | 59.04 | 3.64 | 12.15 | 9.27 |
| Found values | 59.09 | 3.84 | 11.85 | 9.23 |

EXAMPLE 57

6(5)-Chloro-5(6)-(5-isoquinolylsulfanyl)-2-methyl-1H-benzo[d]imidazole

4-Chloro-5-(5-Isoquinolylsulfanyl)-2-nitroaniline 600 mg (1.8 mmol) was dissolved in concentrated hydrochloric acid 8 ml, stannous chloride dihydrate 1.65 g (7.3 mmol) and ethyl acetate 0.4 ml were added, and the mixture was heated and refluxed for 4 hours. The reaction mixture was neutralized with ammonia water, and extracted with ethyl acetate. The organic layer was washed with saturated sodium chloride, dried over anhydrous magnesium sulfate and concentrated under reduced pressure to obtain 6(5)-chloro-5(6)-(5-isoquinolylsulfanyl)-2-methyl-1H-benzo[d]imidazole 204 mg (54.9%).

Melting point: 219–222° C.

Mass spectrometry (m/z): 326 (M+1)

Nuclear magnetic resonance spectrum (DMSO-d$_6$) δ: 9.39(1H,s), 8.57(1H,d), 8.13(1H,d), 7.99(1H,d), 7.72(1H,s), 7.64(1H,dd), 7.57(1H,d), 7.21(1H,s), 2.43(3H,s).

Infrared absorption spectrum $v_{max}$ (KBr) cm$^{-1}$: 1620, 1440, 1380, 1280, 1270, 830, 760.

Element anlysis values (calculated as C$_{17}$H$_{12}$N$_3$SCl)

|  | C(%) | H(%) | N(%) | S(%) |
| --- | --- | --- | --- | --- |
| Theoretical values | 62.67 | 3.71 | 12.90 | 9.84 |
| Found values | 62.68 | 3.84 | 12.61 | 9.49 |

EXAMPLE 58

6(5)-Chloro-5(6)-(5-isoquinolylsulfonyl)-2-methyl-1H-benzo[d]imidazole

6(5)-Chloro-5(6)-(5-isoquinolylsulfanyl)-2-methyl-1H-benzo[d]imidazole 115 mg (0.4 mmol) was dissolved in concentrated sulfuric acid 1.5 ml, Beckmann's reagent 3 ml (K$_2$Cr$_2$O$_7$ 1 g, H$_2$SO$_4$ 1 ml, H$_2$O 9 ml) was added dropwise, and the mixture was stirred overnight at room temperature. The reaction mixture was neutralized with 4N sodium hydroxide, and extracted with ethyl acetate. The organic layer was washed with water and with saturated sodium chloride, dried over anhydrous sodium sulfate and concentrated under reduced pressure. The resulting residue was crystallized from ethyl acetate-hexane, and 6(5)-chloro-5(6)-(5-isoquinolylsulfonyl)-2-methyl-1H-benzo[d]imidazole 50 mg (37.4%) was obtained.

Mass spectrometry (m/z): 358 (M+1)

Nuclear magnetic resonance spectrum (DMSO-d$_6$) δ: 9.39(1H,s), 8.65(1H,d), 8.58(1H,s), 8.46–8.48(2H,m), 8.04 (1H,d), 7.89(1H,dd), 7.55(1H,s), 2.49(3H,s).

Infrared absorption spectrum $v_{max}$ (KBr) cm$^{-1}$: 1620, 1450, 1380, 1300, 1120, 570, 500.

Element anlysis values (calculated as C$_{17}$H$_{12}$ClN$_3$O$_2$S.H$_2$O)

|  | C(%) | H(%) | N(%) | S(%) |
| --- | --- | --- | --- | --- |
| Theoretical values | 54.33 | 3.75 | 11.18 | 8.53 |
| Found values | 54.24 | 3.55 | 10.85 | 8.72 |

EXAMPLE 59

5(6)-(5-Isoquinolylsulfonyl)-2-methyl-1H-benzo[d]imidazole-6(5)-carbonitrile

6(5)-Chloro-5(6)-(5-isoquinolylsulfonyl)-2-methyl-1H-benzo[d]imidazole 330 mg (0.9 mmol) was dissolved in DMF 2.5 ml, copper cyanide 100 mg was added, and the mixture was heated with stirring at 165° C. overnight. A water solution of ethylene diamine was added to the reaction solution, and the solution was extracted with ethyl acetate. The organic layer was washed with water, with saturated sodium chloride, dried over anhydrous sodium sulfate and concentrated under reduced pressure. The resulting residue was purified by silica gel column chromatography (NH silica gel, chloroform-methanol=19:1), and 5(6)-(5-isoquinolylsulfonyl)-2-methyl-1H-benzo[d]imidazole-6(5)-carbonitrile 60 mg (19.0%) was obtained.

Melting point: 170–177° C.

Mass spectrometry (m/z): 349 (M+1)

Nuclear magnetic resonance spectrum (DMSO-d$_6$) δ: 9.46(1H,s), 8.78(1H,d), 8.67(1H,s), 8.60(1H,d), 8.56(1H,d), 8.24(1H,d), 8.16(1H,s), 7.99(1H,dd), 2.58(3H,s).

Infrared absorption spectrum $v_{max}$ (KBr) cm$^{-1}$: 2230, 1620, 1340, 1160, 1130, 580.

Element anlysis values (calculated as C$_{18}$H$_{12}$N$_4$O$_2$S.1/2H$_2$O)

|  | C(%) | H(%) | N(%) |
| --- | --- | --- | --- |
| Theoretical values | 60.49 | 3.67 | 8.97 |
| Found values | 60.37 | 3.66 | 8.82 |

EXAMPLE 60

5(6)-(5-Isoquinolylsulfanyl)-2,6(5)-dimethyl-1H-benzo[d]imidazole 4-(5-Isoquinolylsulfanyl)-5-methyl-1,2-benzene diamine 500 mg (1.8 mmol) was dissolved in 6N hydrochloric acid 10 ml, acetic acid 0.5 ml was added and heated and refluxed overnight. The reaction solution was neutralized with ammonia water and extracted with ethyl acetate. The organic layer was washed with saturated sodium chloride, dried over anhydrous sodium sulfate and concentrated under reduced pressure. 5(6)-(5-Isoquinolylsulfanyl)-2,6(5)-dimethyl-1H-benzo[d]imidazole 490 mg (90.8%) was obtained.

Melting point: 189–191° C.

Mass spectrometry (m/z): 306 (M+1)

Nuclear magnetic resonance spectrum (DMSO-$d_6$) δ: 9.38(1H,s), 8.61(1H,d), 8.06(1H,d), 8.00(1H,d), 7.53–7.57 (3H,m), 7.17(1H,dd).

Infrared absorption spectrum $\nu_{max}$ (KBr) cm$^{-1}$: 1570, 1450, 1290, 820, 750.

Element anlysis values (calculated as $C_{18}H_{15}N_3S$)

|  | C(%) | H(%) | N(%) | S(%) |
|---|---|---|---|---|
| Theoretical values | 70.79 | 4.95 | 13.76 | 10.50 |
| Found values | 70.59 | 5.24 | 13.37 | 10.66 |

EXAMPLE 61

5(6)-(5-Isoquinolylsulfonyl)-2,6(5)-dimethyl-1H-benzo[d]imidazole

According to the method in (a) method of Example 2, 5(6)-(5-isoquinolylsulfonyl)-2,6(5)-dimethyl-1H-benzo[d]imidazole 180 mg (38.3%) was obtained from 5(6)-(5-isoquinolylsulfanyl)-2,6(5)-dimethyl-1H-benzo[d]imidazole 430 mg (1.4 mmol), concentrated sulfuric acid 3.7 ml, and Beckmann's reagent 5 ml ($K_2Cr_2O_7$ 1 g, $H_2SO_4$ 1 ml, $H_2O$ 9 ml).

Melting point: 338° C.

Nuclear magnetic resonance spectrum (DMSO-$d_6$) δ: 8.64(1H,s), 7.78(1H,d), 7.74(1H,d), 7.70(1H,d), 7.64(1H,s), 7.34(1H,d), 7.12(1H,dd), 6.55(1H,s), 1.71(3H,s), 1.49(3H, s).

Infrared absorption spectrum $\nu_{max}$ (KBr) cm$^{-1}$: 1620, 1460, 1400, 1300, 1150, 720, 600, 580, 500.

Element anlysis values (calculated as $C_{18}H_{15}N_3O_2S.1/4H_2O$)

|  | C(%) | H(%) | N(%) |
|---|---|---|---|
| Theoretical values | 63.23 | 4.57 | 12.29 |
| Found values | 63.49 | 4.89 | 12.26 |

EXAMPLE 62

1-Ethyl-6-(5-isoquinolylsulfanyl)-2-methyl-5-nitro-1H-benzo[d]imidazole

5-Isoquinolinethiol 500 mg (3.1 mmol) was dissolved in DMF 20 ml, 6-chloro-1-ethyl-2-methyl-5-nitro-1H-benzo[d]imidazole 910 mg (3.1 mmol) and potassium carbonate 1.29 g (9.3 mmol) were added, and the mixture was stirred for 6 hours at 130° C. The reaction mixture was concentrated under reduced pressure, the residue was crystallized with ethyl acetate, and 1-ethyl-6-(5-isoquinolylsulfanyl)-2-methyl-5-nitro-1H-benzo[d]imidazole 410 mg (35.8%) was obtained.

Melting point: 226–229 ° C.

Mass spectrometry (m/z): 365 (M+1)

Nuclear magnetic resonance spectrum (DMSO-$d_6$) δ: 9.42(1H,s), 8.48(1H,d), 8.44(1H,d), 8.32(1H,d), 8.13(1H,d), 7.78–7.82(2H,m), 6.66(1H,s), 3.79(2H,q), 2.48(3H,s), 0.74 (3H,t).

Infrared absorption spectrum $\lambda_{max}$ (KBr) cm$^{-1}$: 1510, 1310, 760.

Element anlysis values (calculated as $C_{19}H_{16}N_4O_2S.1/4H_2O$)

|  | C(%) | H(%) | N(%) |
|---|---|---|---|
| Theoretical values | 61.86 | 4.51 | 15.19 |
| Found values | 61.48 | 4.27 | 15.00 |

EXAMPLE 63

1-Ethyl-6-(5-isoquinolylsulfonyl)-2-methyl-5-nitro-1H-benzo[d]imidazole

1-Ethyl-6-(5-isoquinolylsulfanyl)-2-methyl-5-nitro-1H-benzo[d]imidazole 300 mg (0.8 mmol) was dissolved in concentrated sulfuric acid 3 ml, Beckmann's reagent 6 ml ($K_2Cr_2O_7$ 1 g, $H_2SO_4$ 1 ml, $H_2O$ 9 ml) was added dropwise, and the mixture was stirred overnight at room temperature. The reaction mixture was neutralized with 4N sodium hydroxide, and the resulting precipitates were collected and washed with water and with ether, and 1-ethyl-6-(5-isoquinolylsulfonyl)-2-methyl-5-nitro-1H-benzo[d]imidazole 320 mg (98.1%) was obtained.

Mass spectrometry (m/z): 397 (M+1)

Nuclear magnetic resonance spectrum (DMSO-$d_6$) δ: 9.48(1H,s), 8.43–8.75(5H,m), 8.23(1H,s), 7.91(1H,dd), 4.52 (2H,q), 2.67(3H,s), 1.37(3H,t).

Infrared absorption spectrum $\nu_{max}$ (KBr) cm$^{-1}$: 1540, 1350, 1320, 1140, 620.

Element anlysis values (calculated as $C_{19}H_{16}N_4O_4S.H_2O$)

|  | C(%) | H(%) | N(%) | S(%) |
|---|---|---|---|---|
| Theoretical values | 55.06 | 4.38 | 13.52 | 7.74 |
| Found values | 54.89 | 4.34 | 13.25 | 7.72 |

EXAMPLE 64

5-Chloro-1-ethyl-6-(5-isoquinolylsulfanyl)-2-methyl-1H-benzo[d]imidazole 5-(4-Amino-5-ethylamino-2-chlorophenylsulfanyl) isoquinoline 210 mg (0.6 mmol) was dissolved in 6N hydrochloric acid 3 ml, acetic acid 0.1 ml was added, and the mixture was heated and refluxed overnight. The reaction mixture was neutralized with ammonia water and extracted with ethyl acetate. The organic layer was washed with saturated sodium chloride, dried over anhydrous magnesium sulfate and concentrated under reduced pressure, and 5-chloro-1-ethyl-6-(5-isoquinolylsulfanyl)-2-methyl-1H-benzo[d]imidazole 130 mg (58.5%) was obtained.

Melting point: 181–184 ° C.

Mass spectrometry (m/z): 354 (M+1)

Nuclear magnetic resonance spectrum (DMSO-$d_6$) δ: 9.33(1H,d), 8.54(1H,dd), 8.26(1H,d), 7.98–8.01(2H,m), 7.76(1H,d), 7.63(1H,d), 7.53(1H,dd), 7.32(1H,dd), 4.07(2H, q), 2.49(3H,s), 1.09(3H,t).

Infrared absorption spectrum $v_{max}$ (KBr) cm$^{-1}$: 3000, 1460, 1400, 820, 750.

Element anlysis values (calculated as $C_{19}H_{16}ClN_3S$)

|  | C(%) | H(%) | N(%) | S(%) |
|---|---|---|---|---|
| Theoretical values | 64.49 | 4.56 | 11.87 | 9.06 |
| Found values | 64.30 | 4.82 | 11.75 | 8.75 |

EXAMPLE 65

1-Ethyl-5-(5-isoquinolylsulfanyl)-2-methyl-6-nitro-1H-benzo[d]imidazole

5-Isoquinolinethiol 500 mg (3.1 mmol) was dissolved in DMF 20 ml, 5-chloro-1-ethyl-2-methyl-6-nitro-1H-benzo[d]imidazole 910 mg (3.1 mmol) and potassium carbonate 1.29 g (9.3 mmol) were added, and the mixture was stirred for 3 hours at 130° C. The reaction mixture was concentrated under reduced pressure, the residue was crystallized with ethyl acetate, and 1-ethyl-5-(5-isoquinolylsulfanyl)-2-methyl-6-nitro-1H-benzo[d]imidazole 480 mg (42.3%) was obtained.

Melting point: 236–242 ° C.

Mass spectrometry (m/z): 365 (M+1)

Nuclear magnetic resonance spectrum (DMSO-d$_6$) δ: 9.45(1H,d), 8.62(1H,s), 8.49(1H,d), 8.37(1H,d), 8.21(1H,dd), 7.82–7.86(2H,m), 6.54(1H,s), 4.28(2H,q), 2.46(3H,s), 1.27(3H,t).

Infrared absorption spectrum $v_{max}$ (KBr) cm$^{-1}$: 1520, 1440, 1310.

Element anlysis values (calculated as $C_{19}H_{16}N_4O_2S.1/2H_2O$)

|  | C(%) | H(%) | N(%) |
|---|---|---|---|
| Theoretical values | 61.11 | 4.59 | 15.00 |
| Found values | 60.96 | 4.25 | 15.09 |

EXAMPLE 66

1-Ethyl-5-(5-isoquinolylsulfonyl)-2-methyl-6-nitro-1H-benzo[d]imidazole

1-Ethyl-5-(5-isoquinolylsulfanyl)-2-methyl-6-nitro-1H-benzo[d]imidazole 300 mg (0.8 mmol) was dissolved in concentrated sulfuric acid 3 ml, Beckmann's reagent ($K_2Cr_2O_7$ 1 g, $H_2SO_4$ 1 ml, $H_2O$ 9 ml) 6 ml was added dropwise, and the mixture was stirred overnight at room temperature. The reaction mixture was neutralized with 4N sodium hydroxide and extracted with ethyl acetate. The organic layer was dried over anhydrous magnesium sulfate and concentrated under reduced pressure, and 1-ethyl-5-(5-isoquinolylsulfonyl)-2-methyl-6-nitro-1H-benzo[d]imidazole 70 mg (20.8%) was obtained.

Melting point: 245–250 ° C.

Mass spectrometry (m/z): 397 (M+1)

Nuclear magnetic resonance spectrum (DMSO-d$_6$) δ: 9.48(1H,s), 8.64(1H,d), 8.55(1H,d), 8.52(1H,d), 8.43–8.45(2H,m), 8.32(1H,d), 7.91(1H,dd), 4.32(2H,q), 2.66(3H,s), 1.31(3H,t).

Infrared absorption spectrum $v_{max}$ (KBr) cm$^{-1}$: 1540, 1350, 1310.

Element anlysis values (calculated as $C_{19}H_{16}N_4O_4S.1/4H_2O$)

|  | C(%) | H(%) | N(%) | S(%) |
|---|---|---|---|---|
| Theoretical values | 56.92 | 4.15 | 13.97 | 8.00 |
| Found values | 56.74 | 4.14 | 14.36 | 8.26 |

EXAMPLE 67

N1-Benzyl-5-(5-isoquinolylsulfanyl)-2-nitroaniline 5-(5-Isoquinolylsulfanyl)-2-nitroaniline 2.00 g (6.7 mmol) was dissolved in DMF 40 ml, 60% NaH 300 mg (7.4 mmol) and benzilbromide 1.26 g (7.4 mmol) were added, and the mixture was stirred overnight at room temperature. The reaction mixture was poured into ice water and extracted with ethyl acetate. The organic layer was washed with saturated sodium chloride, dried over anhydrous magnesium sulfate and concentrated under reduced pressure. The resulting residue was purified by silica gel column chromatography (silica gel 30 g, chloroform: ethyl acetate= 5:1), and N1-benzyl-5-(5-isoquinolylsulfanyl)-2-nitroaniline 1.51 g (57.9%) was obtained.

Melting point: 153–154° C.

Mass spectrometry (m/z): 388 (M+1)

Nuclear magnetic resonance spectrum (CDCl$_3$) δ: 9.29 (1H,d), 8.52(1H,d), 8.45(1H,brs), 8.07(1H,d), 8.01(1H,d), 7.95(1H,dd), 7.90(1H,d), 7.58(1H,dd), 7.13–7.17(3H,m), 6.88–6.89(2H,m), 6.35(1H,dd), 6.08(1H,d), 4.13(2H,d).

Infrared absorption spectrum $v_{max}$ (KBr) cm$^{-1}$: 1600, 1565, 1480, 1320, 1240, 1200.

Element anlysis values (calculated as $C_{22}H_{17}N_3O_2S$)

|  | C(%) | H(%) | N(%) | S(%) |
|---|---|---|---|---|
| Theoretical values | 68.20 | 4.42 | 10.84 | 8.28 |
| Found values | 67.83 | 4.63 | 10.67 | 8.12 |

EXAMPLE 68

N2-Benzyl-4-(5-isoquinolylsulfanyl)-1,2-benzene diamine

N1-Benzyl-5-(5-isoquinolylsulfanyl)-2-nitroaniline 840 mg (2.2 mmol) was dissolved in concentrated hydrochloric acid 25 ml, stannous chloride dihydrate 2.45 g (10.8 mmol) was added, and the mixture was stirred overnight at room temperature. 50% sodium chloride was added to obtain an alkaline solution, and the solution was extracted with ethyl acetate. The organic layer was washed with water and with saturated sodium chloride, dried over anhydrous magnesium sulfate and concentrated under reduced pressure, and N2-benzyl-4-(5-isoquinolylsulfanyl)-1,2-benzene diamine 730 mg (94.1%) was obtained.

Melting point: 125–127° C.

Mass spectrometry (m/z): 358 (M+1)

Nuclear magnetic resonance spectrum (DMSO-d$_6$) δ: 9.15(1H,s), 8.49(1H,d), 8.02(1H,d), 7.70(1H,d), 7.21–7.35 (7H,m), 6.79(1H,dd), 6.73(1H,d), 6.67(1H,d), 4.17(2H,s).

Infrared absorption spectrum $v_{max}$ (KBr) cm$^{-1}$: 1590, 1570, 1520, 820, 740, 695.

Element anlysis values (calculated as $C_{22}H_{19}N_3S.1/4H_2O$)

|                   | C(%)  | H(%) | N(%)  |
|-------------------|-------|------|-------|
| Theoretical values | 73.00 | 5.43 | 11.61 |
| Found values      | 73.05 | 5.22 | 11.36 |

|                   | C(%)  | H(%) | N(%)  | S(%)  |
|-------------------|-------|------|-------|-------|
| Theoretical values | 69.76 | 5.04 | 13.56 | 10.35 |
| Found values      | 69.84 | 4.96 | 13.58 | 10.43 |

EXAMPLE 69

1-Benzyl-6-(5-isoquinolylsulfanyl)-2-methyl-1H-benzo[d]imidazole

N2-Benzyl-4-(5-isoquinolylsulfanyl)-1,2-benzenediamine 730 mg (2.0 mmol) was dissolved in 4N hydrochloric acid 20 ml, acetic acid 0.3 ml was added, and the mixture was heated and refluxed overnight. 40% sodium chloride was added to obtain an alkaline solution, and the solution was extracted with ethyl acetate. The organic layer was dried over anhydrous magnesium sulfate and concentrated under reduced pressure. The resulting residue was purified by silica gel column chromatography (chloroform:acetone=5:1), and 1-benzyl-6-(5-isoquinolylsulfanyl)-2-methyl-1H-benzo[d]imidazole 330 mg (43.3%) was obtained.

Melting point: 174–177° C.

Mass spectrometry (m/z): 382 (M+1)

Nuclear magnetic resonance spectrum (DMSO-$d_6$) δ: 9.21(1H,s), 8.50(1H,d), 8.03(1H,d), 7.81(1H,d), 7.65(1H,d), 7.46(1H,dd), 7.41(1H,dd), 7.23–7.27(5H,m), 6.93–6.95(2H,m), 5.20(2H,s), 2.55(3H,s).

Infrared absorption spectrum $v_{max}$ (KBr) cm$^{-1}$: 1450, 1400, 1360, 1280, 820, 730.

Element anlysis values (calculated as $C_{24}H_{19}N_3S.1/2H_2O$)

|                   | C(%)  | H(%) | N(%)  | S(%) |
|-------------------|-------|------|-------|------|
| Theoretical values | 73.82 | 5.16 | 10.76 | 8.21 |
| Found values      | 73.56 | 5.44 | 11.15 | 8.53 |

EXAMPLE 70

-2-Ethyl-5(6)-(5-isoquinolylsulfanyl)-1H-benzo[d]imidazole 5-(5-Isoquinolylsulfanyl)-2-nitroaniline 3.10 g (10.4 mmol) was dissolved in concentrated hydrochloric acid 40 ml, stannous chloride dihydrate 10.10 g (44.9 mmol) and propionic acid 4.2 ml were added, and the mixture was heated and refluxed overnight. 40% sodium chloride was added, the solution was neutralized with a saturated sodium bicarbonate and extracted with ethyl acetate. The organic layer was dried over anhydrous sodium sulfate and concentrated under reduced pressure. The resulting residue was crystallized with ethyl acetate, and 2-ethyl-5(6)-(5-isoquinolylsulfanyl)-1H-benzo[d]imidazole 3.18 g (59.1%) was obtained.

Melting point: 185–188° C.

Mass spectrometry (m/z): 306 (M+1)

Nuclear magnetic resonance spectrum (DMSO-$d_6$) δ: 9.34(1H,s), 8.56(1H,d), 8.02–8.06(2H,m), 7.49–7.59(4H,m), 7.20(1H,d), 2.82(2H,q), 1.29(3H,t).

Infrared absorption spectrum $v_{max}$ (KBr) cm$^{-1}$: 1620, 1540, 820.

Element anlysis values (calculated as $C_{18}H_{15}N_3S.1/4H_2O$)

EXAMPLE 71

2-Ethyl-5(6)-(5-isoquinolylsulfonyl)-1H-benzo[d]imidazole

2-Ethyl-5(6)-(5-isoquinolylsulfanyl)-1H-benzo[d]imidazole 6.90 g (22.6 mmol) was dissolved in concentrated sulfuric acid 69 ml, Beckmann's reagent 138 ml ($K_2Cr_2O_7$ 1 g, $H_2SO_4$ 1 ml, $H_2O$ 9 ml) was added dropwise, and the mixture was stirred for 4.5 hours at room temperature. The reaction mixture was neutralized with 50% sodium hydroxide and extracted with ethyl acetate. The organic layer was washed with water and with saturated sodium chloride, dried over anhydrous magnesium sulfate and concentrated under reduced pressure. The resulting residue was crystallized with chloroform, and 2-ethyl-5(6)-(5-isoquinolylsulfonyl)-1H-benzo[d]imidazole 4.33 g (56.8%) was obtained.

Melting point: 241–243° C.

Mass spectrometry (m/z): 338 (M+1)

Nuclear magnetic resonance spectrum (DMSO-$d_6$) δ: 9.34(1H,s), 8.67(1H,d), 8.63(1H,d), 8.48(1H,d), 8.41(1H,d), 8.17(1H,brs), 7.92(1H,t), 7.70(1H,d), 7.62(1H,brs), 2.85(2H,q), 1.28(3H,t).

Infrared absorption spectrum $v_{max}$ (KBr) cm$^{-1}$: 1620, 1380, 1130, 630.

Element anlysis values (calculated as $C_{18}H_{15}FN_3O_2S.1/4H_2O$)

|                   | C(%)  | H(%) | N(%)  | S(%) |
|-------------------|-------|------|-------|------|
| Theoretical values | 63.23 | 4.57 | 12.29 | 9.38 |
| Found values      | 62.89 | 4.63 | 12.22 | 9.55 |

EXAMPLE 72

2-Ethyl-5(6)-(5-isoquinolylsulfanyl)-6(5)-nitro-1H-benzo[d]imidazole

N1-[2-Ethylcarboxamide-4-(5-isoquinolylsulfanyl)-5-nitrophenyl]propanamide 350 mg (0.8 mmol) was dissolved in concentrated hydrochloric acid 4 ml, and the mixture was heated and refluxed for 18 hours. The reaction mixture was concentrated under reduced pressure, the residue was crystallized from ethanol, and 2-ethyl-5(6)-(5-isoquinolylsulfanyl)-6(5)nitro-1H-benzo[d]imidazole hydochloride 300 mg (64.8%) was obtained.

Melting point: >270° C.

Mass spectrometry (m/z): 351 (M+1)

Nuclear magnetic resonance spectrum (DMSO-$d_6$) δ: 9.93(1H,s), 8.69(1H,d), 8.62(1H,d), 8.60(1H,s), 8.52(1H,dd), 8.37(1H,d), 8.09(1H,t), 6.69(1H,s).

Infrared absorption spectrum $v_{max}$ (KBr) cm$^{-1}$: 2625, 1525, 1455, 1330, 820, 515.

Element anlysis values (calculated as $C_{18}H_{14}N_4O_2S.3HCl.1/2H_2O$)

|                   | C(%)  | H(%) | N(%)  |
| ----------------- | ----- | ---- | ----- |
| Theoretical values | 46.12 | 3.87 | 11.95 |
| Found values      | 45.74 | 3.53 | 11.69 |

EXAMPLE 73

2-Ethyl-5(6)-(5-isoquinolylsulfonyl)-6(5)-nitro-1H-benzo[d]imidazole and 2-ethyl-5(6)-(5-isoquinolylsulfonyl)-7(4)-nitro-1H-benzo[d]imidazole According to the same method in Example 30, 2-ethyl-5(6)-(5-isoquinolylsulfonyl)-6(5)-nitro-1H-benzo[d]imidazole was synthesized by the following (a) and (b) methods, and 2-ethyl-5(6)-(5-isoquinolylsulfonyl)-7(4)-nitro-1H-benzo[d]imidazole was synthesized by (b) method.

(a) method: 2-ethyl-5(6)-(5-isoquinolylsulfonyl)-6(5)-nitro-1H-benzo[d]imidazole 2-Ethyl-5(6)-(5-isoquinolylsulfanyl)-6(5)-nitro-1H-benzo[d]imidazole 200 mg (0.4 mmol) was dissolved in concentrated sulfuric acid 1.5 ml, Beckmann's reagent ($K_2Cr_2O_7$ 1 g, $H_2SO_4$ 1 ml, $H_2O$ 9 ml) 3.0 ml was added dropwise, and the mixture was stirred for 5 hours at room temperature. After adding water, the reaction mixture was neutralized with 4N sodium hydroxide, and the resulting precipitates were filtered and washed with water. The resulting residue was dissolved in methanol, and methanol saturated with hydrogen chloride was added. The solution was concentrated under reduced pressure, the residue was crystallized from ethyl acetate, and 2-ethyl-5(6)-(5-isoquinolylsulfonyl)-6(5)-nitro-1H-benzo[d]imidazole hydrochloride 40 mg (23.1%) was obtained.

Melting point: 249–256° C.

Mass spectrometry (m/z): 383 (M+1)

Nuclear magnetic resonance spectrum (DMSO-$d_6$) δ: 9.70(1H,s), 8.71(1H,d), 8.66(1H,d), 8.61(1H,s), 8.54–8.50 (2H,m), 8.31(1H,s), 8.12(1H,t), 2.99(2H,q), 1.36(3H,t).

Infrared absorption spectrum $v_{max}$ (KBr) cm$^{-1}$: 1550, 1350, 1140.

Element anlysis values (calculated as $C_{18}H_{14}N_4O_4S.4HCl$)

|                    | C(%)  | H(%) | N(%)  |
| ------------------ | ----- | ---- | ----- |
| Theoretical values | 40.93 | 3.43 | 10.61 |
| Found values       | 40.50 | 3.51 | 10.81 |

(b) method: nitration of 2-ethyl-5(6)-(5-isoquinolylsulfonyl)-1H-benzo[d]imidazole According to the method in Example 30, 2-ethyl-5(6)-(5-isoquinolylsulfonyl)-1H-benzo[d]imidazole 4.10 g (12.2 mmol) was nitrated, and 2-ethyl-5(6)-(5-isoquinolylsulfonyl)-6(5)-nitro-1H-benzo[d]imidazole 2.58 g (55.5%) and 2-ethyl-5(6)-(5-isoquinolylsulfonyl)-7(4)-nitro-1H-benzo[d]imidazole 560 mg (12.1%) were obtained.

2-Ethyl-5(6)-(5-isoquinolylsulfonyl)-6(5)-nitro-1H-benzo[d]imidazole

Melting point: 222–227° C.

Mass spectrometry (m/z): 383 (M+1)

Nuclear magnetic resonance spectrum (DMSO-$d_6$) δ: 9.50(1H,s), 8.65(1H,d), 8.54(1H,s), 8.53(1H,d), 8.43(1H,d), 8.29(1H,s), 7.94(1H,t), 7.92(1H,dd), 2.96(2H,q), 1.34(3H,t).

Infrared absorption spectrum $v_{max}$ (KBr) cm$^{-1}$: 1535, 1320, 1140, 820.

Element anlysis values (calculated as $C_{17}H_{12}N_4S$)

|                    | C(%)  | H(%) | N(%)  | S(%) |
| ------------------ | ----- | ---- | ----- | ---- |
| Theoretical values | 56.54 | 3.69 | 14.65 | 8.39 |
| Found values       | 56.23 | 3.90 | 14.43 | 8.02 |

2-Ethyl-5(6)-(5-isoquinolylsulfonyl)-7(4)-nitro-1H-benzo[d]imidazole

Melting point: 172–175° C.

Mass spectrometry (m/z): 383 (M+1)

Nuclear magnetic resonance spectrum (DMSO-$d_6$) δ: 9.45(1H,s), 8.77(1H,d), 8.67(1H,d), 8.63(1H,s), 8.51(1H,d), 8.44(1H,d), 7.94(1H,d), 2.93(2H,q), 1.29(3H,t).

Infrared absorption spectrum $v_{max}$ (KBr) cm$^{-1}$: 1620, 1540, 1370, 1360, 1320, 1140, 1000, 820, 730, 620, 500.

Element anlysis values (calculated as $C_{18}H_{14}N_4O_4S.3/4H_2O$)

|                    | C(%)  | H(%) | N(%)  | S(%) |
| ------------------ | ----- | ---- | ----- | ---- |
| Theoretical values | 54.61 | 3.95 | 14.15 | 8.10 |
| Found values       | 54.42 | 4.19 | 14.25 | 8.04 |

EXAMPLE 74

6(5)-Chloro-2-ethyl-5(6)-(5-isoquinolylsulfanyl)-1H-benzo[d]imidazole

4-Chloro-5-(5-isoquinolylsulfanyl)-1,2-benzenediamine 600 mg (2.0 mmol) was dissolved in 4N hydrochloric acid 8.5 ml, propionic acid 0.6 ml was added, and the mixture was heated and refluxed overnight. 40% sodium chloride was added to neutralize the solution, and the solution was extracted with ethyl acetate. The organic layer was dried over anhydrous sodium sulfate and concentrated under reduced pressure. The resulting residue was purified by silica gel column chromatography (chloroform:methanol= 10:1), and 6(5)-chloro-2-ethyl-5(6)-(5-isoquinolylsulfanyl)-1H-benzo[d]imidazole 580 mg (85.8%) was obtained.

Mass spectrometry (m/z): 340 (M+1)

Nuclear magnetic resonance spectrum (DMSO-$d_6$) δ: 9.39(1H,s), 8.57(1H,d), 8.30(1H,d), 8.13(1H,d), 8.00(1H,d), 7.73(1H,s), 7.65(1H,dd), 7.60(1H,d), 7.19(1H,brs), 2.77(2H,q), 1.25(3H,t).

Infrared absorption spectrum $v_{max}$ (KBr) cm$^{-1}$: 1620, 1450, 750.

Element anlysis values (calculated as $C_{18}H_{14}ClN_3S.H_2O$)

|                    | C (%) | H (%) | N (%) | S (%) |
| ------------------ | ----- | ----- | ----- | ----- |
| Theoretical values | 60.41 | 4.51  | 11.77 | 8.96  |
| Found values       | 60.19 | 4.18  | 11.53 | 9.06  |

EXAMPLE 75

6(5)-Chloro-2-ethyl-5(6)-(5-isoquinolylsulfonyl)-1H-benzo[d]imidazole

6(5)-Chloro-2-ethyl-5(6)-(5-isoquinolylsulfanyl)-1H-benzo[d]imidazole 480 mg (1.4 mmol) was dissolved in concentrated sulfuric acid 5.0 ml, Beckmann's reagent 3.5 ml ($K_2Cr_2O_7$ 1 g, $H_2SO_4$ 1 ml, $H_2O$ 9 ml) was added dropwise, and the mixture was stirred overnight at room temperature. The reaction mixture was neutralized with 50% sodium hydroxide and extracted with ethyl acetate. The organic layer was washed with water and with saturated sodium chloride, dried over anhydrous sodium sulfate, and concentrated under reduced pressure. The resulting residue was crystallized from ethyl acetate-hexane, and 6(5)-chloro-2-ethyl-5(6)-(5-isoquinolylsulfonyl)1H-benzo[d]imidazole 377 mg (72.1%) was obtained.

Mass spectrometry (m/z): 372 (M+1)

Nuclear magnetic resonance spectrum (DMSO-$d_6$) δ: 9.45(1H,d), 8.72(1H,d), 8.66(1H,brs), 8.53–8.56(2H,m), 8.12(1H,d), 7.95(1H,dd), 7.63(1H,brs), 2.91(2H,q), 1.33 (3H,t).

Infrared absorption spectrum $v_{max}$ (KBr) cm$^{-1}$: 1620, 1460, 1320, 1150, 1130, 575, 500.

Element anlysis values (calculated as $C_{18}H_{14}ClN_3O_2S$)

|  | C (%) | H (%) | N (%) | S (%) |
|---|---|---|---|---|
| Theoretical values | 58.14 | 3.79 | 11.30 | 8.62 |
| Found values | 58.06 | 4.13 | 11.06 | 8.40 |

EXAMPLE 76

5(6)-(5-Isoquinolylsulfanyl)-2-propyl-1H-benzo[d]imidazole 5-(5-Isoquinolylsulfanyl)-2-nitroaniline 3.10 g (10.4 mmol) was dissolved in concentrated hydrochloric acid 40 ml, stannous chloride dihydrate 10.10 g (44.9 mmol) and butylic acid 2.2 ml were added, and the mixture was heated and refluxed for 4.5 hours. The reaction solution was neutralized with saturated sodium bicarbonate and extracted with ethyl acetate. The organic layer was washed with saturated sodium chloride, dried over anhydrous sodium sulfate and concentrated under reduced pressure, and 5(6)-(5-isoquinolylsulfanyl)-2-propyl-1H-benzo[d]imidazole 1.24 g (37.2%) was obtained.

Melting point: 202–207° C.

Mass spectrometry (m/z): 320 (M+1)

Nuclear magnetic resonance spectrum (DMSO-$d_6$) δ: 9.35(1H,s), 8.57(1H,d), 8.07(1H,d), 8.04(1H,d), 7.49–7.60 (4H,m), 7.20(1H,dd), 2.76(2H,t), 1.74–1.78(2H,m), 0.92 (3H,t).

Infrared absorption spectrum $v_{max}$ (KBr) cm$^{-1}$: 1440, 1410, 1290, 810, 750.

Element anlysis values (calculated as $C_{19}H_{17}N_3S.1/2H_2O$)

|  | C (%) | H (%) | N (%) |
|---|---|---|---|
| Theoretical values | 69.48 | 5.52 | 12.79 |
| Found values | 69.61 | 5.57 | 12.56 |

EXAMPLE 77

5(6)-(5-Isoquinolylsulfonyl)-2-propyl-1H-benzo[d]imidazole

5(6)-(5-Isoquinolylsulfanyl)-2-propyl-1H-benzo[d]imidazole 460 mg (1.4 mmol) was dissolved in concentrated sulfuric acid 10 ml, Beckmann's reagent 22 ml ($K_2Cr_2O_7$ 1 g, $H_2SO_4$ 1 ml, $H_2O$ 9 ml) was added dropwise, and the mixture was stirred overnight at room temperature. The reaction mixture was neutralized with 4N sodium hydroxide, the resulting precipitates were collected and washed with water and with ether, and 5(6)-(5-isoquinolylsulfonyl)-2-propyl-1H-benzo[d]imidazole 390 mg (76.8%) was obtained.

Melting point: 220–222° C.

Mass spectrometry (m/z): 352 (M+1)

Nuclear magnetic resonance spectrum (DMSO-$d_6$) δ: 9.26(1H,s), 8.63(1H,dd), 8.53(1H,d), 8.47(1H,d), 8.21(1H, d), 8.17(1H,d), 7.70–7.73(2H,m), 7.50(1H,d), 2.83(2H,t), 1.77–1.81(2H,m),0.90(3H,t).

Infrared absorption spectrum $v_{max}$ (KBr) cm$^{-1}$: 1310, 1280, 1150, 1130, 630, 600, 500.

Element anlysis values (calculated as $C_{19}H_{17}N_3O_2S.3/4H_2O$)

|  | C (%) | H (%) | N (%) | S (%) |
|---|---|---|---|---|
| Theoretical values | 62.53 | 5.11 | 11.51 | 8.79 |
| Found values | 62.39 | 4.72 | 11.14 | 8.71 |

EXAMPLE 78

5(6)-(5-Isoquinolylsulfonyl)-6(5)-nitro-2-propyl-1H-benzo[d]imidazole and 5(6)-(5-isoquinolylsulfonyl)-7(4)-nitro-2-propyl-1H-benzo[d]imidazole According to the method in Example 30, 5(6)-(5-isoquinolylsulfonyl)-2-propyl-1H-benzo[d]imidazole 1.87 g (5.3 mmol) was nitrated, and 5(6)-(5-isoquinolylsulfonyl)-6(5)-nitro-2-propyl-1H-benzo[d]imidazole 1.00 g (47.4%) and 5(6)-(5-isoquinolylsulfonyl)-7(4)-nitro-2-propyl-1H-benzo[d]imidazole 240 mg (11.4%) were obtained.

5(6)-(5-isoquinolylsulfonyl)-6(5)-nitro-2-propyl-1H-benzo[d]imidazole

Melting point: 199–202° C.

Mass spectrometry (m/z): 397 (M+1)

Nuclear magnetic resonance spectrum (DMSO-$d_6$) δ: 9.49(1H,s), 8.65(1H,d), 8.56(1H,s), 8.53(1H,d), 8.43(1H,d), 8.32(1H,d), 8.27(1H,s), 7.91(1H,dd), 2.90(2H,t), 1.81(2H, q),0.94(3H,t).

Infrared absorption spectrum $v_{max}$ (KBr) cm$^{-1}$: 1540, 1310, 1130.

Element anlysis values (calculated as $C_{19}H_{16}N_4O_4S.4H_2O$)

|  | C (%) | H (%) | N (%) | S (%) |
|---|---|---|---|---|
| Theoretical values | 48.71 | 5.16 | 11.96 | 6.84 |
| Found values | 48.70 | 5.16 | 11.65 | 5.94 |

5(6)-(5-isoquinolylsulfonyl)-7(4)-nitro-2-propyl-1H-benzo[d]imidazole

Melting point: 159–161° C.

Mass spectrometry (m/z): 397 (M+1)

Nuclear magnetic resonance spectrum (DMSO-$d_6$) δ: 9.46(1H,s), 8.79(1H,d), 8.68(1H,d), 8.65(1H,s), 8.53(1H,d), 8.46(1H,d), 7.95(1H,dd), 2.90(2H,t), 1.78(2H,m), 0.92(3H, q).

Infrared absorption spectrum $v_{max}$ (KBr) cm$^{-1}$: 1520, 1320, 1130, 620.

EXAMPLE 79

6(5)-Chloro-5(6)-(5-isoquinolylsulfanyl)-2-propyl-1H-benzo[d]imidazole

4-Chloro-5-(5-isoquinolylsulfanyl)-1,2-benzene diamine 600 mg (2.0 mmol) was dissolved in 6N hydrochloric acid 9 ml, butyric acid 0.8 ml was added, and the mixture was heated and refluxed overnight. The reaction mixture was neutralized with saturated sodium bicarbonate, and extracted with ethyl acetate. The organic layer was washed with saturated sodium chloride, dried over anhydrous sodium sulfate, and concentrated under reduced pressure. The resulting residue was dissolved in methanol, 6N hydrochloric acid and ether were added, and the precipitates were collected to give 6(5)chloro-5(6)-(5-isoquinolylsulfanyl)-2-propyl-1H-benzo[d]imidazole hydrochloride 690 mg (81.4%) was obtained.

Melting point: 259–262° C.

Mass spectrometry (m/z): 354 (M+1)

Nuclear magnetic resonance spectrum (DMSO-$d_6$) δ: 9.92(1H,s), 8.71(1H,d), 8.57(1H,d), 8.43(1H,d), 8.14(1H,d), 8.06(1H,s), 7.97(1H,dd), 7.26(1H,s).

Infrared absorption spectrum $v_{max}$ (KBr) cm$^{-1}$: 1650, 1600, 1450, 960, 830.

Element anlysis values (calculated as $C_{19}H_{16}ClN_3S \cdot 2HCl \cdot 1/4H_2O$)

|  | C (%) | H (%) | N (%) |
|---|---|---|---|
| Theoretical values | 52.91 | 4.32 | 9.74 |
| Found values | 52.78 | 3.92 | 9.57 |

EXAMPLE 80

6(5)-Chloro-5(6)-(5-isoquinolylsulfonyl)-2-propyl-1H-benzo[d]imidazole

6(5)-Chloro-5(6)-(5-isoquinolylsulfanyl)-2-propyl-1H-benzo[d]imidazole dihydrochloride 630 mg (1.5 mmol) was dissolved in concentrated sulfuric acid 3.8 ml, Beckmann's reagent 5.7 ml ($K_2Cr_2O_7$ 1 g, $H_2SO_4$ 1 ml, $H_2O$ 9 ml) was added dropwise, and the mixture was stirred overnight at room temperature. The reaction mixture was neutralized with 4N sodium hydroxide solution, and the resulting precipitates were collected and washed with water and with ether. The resulting residue was purified by silica gel column chromatography (dichloromethane: ethyl acetate=2:1), and 6(5)-chloro-5(6)-(5-isoquinolylsulfonyl)-2-propyl-1H-benzo[d]imidazole 170 mg (29.1%) was obtained.

Melting point: 386° C.

Nuclear magnetic resonance spectrum (DMSO-$d_6$) δ: 9.46(1H,s), 8.72(1H,d), 8.66(1H,s), 8.53(1H,d), 8.13(1H,d), 7.95(1H,dd), 7.64(1H,s), 2.85(2H,t), 1.80(2H,dq), 0.93(3H,t).

Infrared absorption spectrum $v_{max}$ (KBr) cm$^{-1}$: 2960, 1620, 1460, 1320, 1125.

Element anlysis values (calculated as $C_{19}H_{16}ClN_3O_2S$)

|  | C (%) | H (%) | N (%) |
|---|---|---|---|
| Theoretical values | 59.14 | 4.18 | 10.89 |
| Found values | 59.38 | 3.97 | 10.60 |

EXAMPLE 81

2-Isopropyl-5(6)-(5-isoquinolylsulfanyl)-1H-benzo[d]imidazole 5-(5-Isoquinolylsulfanyl)-2-nitroaniline 3.10 g (10.4 mmol) was dissolved in concentrated hydrochloric acid 40 ml, stannous chloride dihydrate 10.01 g (44.5 mmol) and isobutylic acid 4.2 ml were added, and the mixture was heated and refluxed overnight. The reaction mixture was neutralized with saturated sodium bicarbonate and extracted with ethyl acetate. The organic layer was washed with saturated sodium chloride, dried over anhydrous sodium sulfate and concentrated under reduced pressure, and 2-isopropyl-5(6)-(5-isoquinolylsulfanyl)-1H-benzo[d]imidazole 2.75 g (82.1%) was obtained.

Mass spectrometry (m/z): 320 (M+1)

Nuclear magnetic resonance spectrum (DMSO-$d_6$) δ: 9.35(1H,s), 8.57(1H,d), 8.00–8.07(2H,m), 7.40–7.60(4H,m), 7.22(1H,d), 3.12(1H,m), 1.32(3H,s), 1.31(3H,s), 7.25 (1H,dd).

Infrared absorption spectrum $v_{max}$ (KBr) cm$^{-1}$: 1615, 1450, 1410, 1260, 815.

Element anlysis values (calculated as $C_{19}H_{17}N_3S \cdot 1/4H_2O$)

|  | C (%) | H (%) | N (%) | S (%) |
|---|---|---|---|---|
| Theoretical values | 70.45 | 5.45 | 12.97 | 9.90 |
| Found values | 70.08 | 5.74 | 13.00 | 9.60 |

EXAMPLE 82

2-Isopropyl-5(6)-(5-isoquinolylsulfonyl)-1H-benzo[d]imidazole and 2-[5(6)-(5-isoquinolylsulfonyl)-1H-benzo[d]imidazole-2-yl]-2-propanol 2-Isopropyl-5(6)-(5-isoquinolylsulfanyl)-1H-benzo[d]imidazole 5.00 g (15.7 mmol) was dissolved in concentrated sulfuric acid 50 ml, Beckmann's reagent 100 ml ($K_2Cr_2O_7$ 1 g, $H_2SO_4$ 1 ml, $H_2O$ 9 ml) was added dropwise, and the mixture was stirred overnight at room temperature. The reaction mixture was neutralized with 50% sodium hydroxide and extracted with ethyl acetate. The organic layer was washed with water and saturated sodium chloride, dried over anhydrous sodium sulfate, and concentrated under reduced pressure. The resulting residue was purified by silica gel column chromatography (methanol: ethyl acetate =1:50), and 2-isopropyl-5(6)-(5-isoquinolylsulfonyl)-1H-benzo[d]imidazole 610 mg (16.5%) and 2-[5(6)-(5-isoquinolylsulfonyl)-1H-benzo[d]imidazole-2-yl]-2-propanol 450 mg (11.7%) were obtained.

2-isopropyl-5(6)-(5-isoquinolylsulfonyl)-1H-benzo[d]imidazole

Melting point: 207–222° C.

Mass spectrometry (m/z): 352 (M+1)

Nuclear magnetic resonance spectrum (DMSO-$d_6$) δ: 9.43(1H,s), 8.62–8.67(2H,m), 8.47(1H,d), 8.42(1H,d), 8.15 (1H,s), 7.92(1H,dd), 7.69(1H,dd), 7.60(1H,d), 3.14(1H,m), 1.31(3H,s), 1.29(3H,s).

Infrared absorption spectrum $v_{max}$ (KBr) cm$^{-1}$: 1620, 1310, 1155, 1120, 630.

Element anlysis values (calculated as $C_{19}H_{17}N_3O_2S \cdot 1/2H_2O$)

|  | C (%) | H (%) | N (%) |
|---|---|---|---|
| Theoretical values | 63.31 | 5.03 | 11.66 |
| Found values | 63.13 | 4.69 | 11.34 |

2-[5(6)-(5-isoquinolylsulfonyl)-1H-benzo[d]imidazole-2-yl]-2-propanol

Melting point: 238–240° C.

Mass spectrometry (m/z): 368 (M+1)

Nuclear magnetic resonance spectrum (DMSO-$d_6$) δ: 9.43(1H,s), 8.63-8.67(2H,m), 8.47(1H,d), 8.41(1H,d), 8.19 (1H,s), 7.92(1H,dd), 7.73(1H,d), 7.64(1H,d), 5.75(1H,s), 1.53(6H,s).

Infrared absorption spectrum $v_{max}$ (KBr) cm$^{-1}$: 1620, 1310, 1150, 1120, 720, 630, 600.

Element anlysis values (calculated as $C_{19}H_{17}N_3O_3S$)

|                   | C (%) | H (%) | N (%) | S (%) |
|-------------------|-------|-------|-------|-------|
| Theoretical values| 62.11 | 4.65  | 11.44 | 8.73  |
| Found values      | 62.48 | 4.63  | 11.41 | 9.10  |

EXAMPLE 83

2-Isopropyl-5(6)-(5-isoquinolylsulfonyl)-6(5)-nitro-1H-benzo[d]imidazole and 2-isopropyl-5(6)-(5-isoquinolylsulfonyl)-7(4)-nitro-1H-benzo[d]imidazole According to the same method in Example 30, 2-isopropyl-5(6)-(5-isoquinolylsulfonyl)-1H-benzo[d] imidazole 500 mg (1.4 mmol) was nitrated, and 2-isopropyl-5(6)-(5-isoquinolylsulfonyl)-6(5)-nitro-1H-benzo[d] imidazole 305 mg (54.1%) and 2-isopropyl-5(6)-(5-isoquinolylsulfonyl)-7(4)-nitro-1H-benzo[d]imidazole 62 mg (11.0%) were obtained.

2-isopropyl-5(6)-(5-isoquinolylsulfonyl)-6(5)-nitro-1H-benzo[d]imidazole

Melting point: 231–234° C.

Mass spectrometry (m/z): 397 (M+1)

Nuclear magnetic resonance spectrum (DMSO-$d_6$) δ: 9.45(1H,s), 8.77(1H,d), 8.67(1H,d), 8.61(1H,brs), 8.52(1H,d), 8.48(1H,brs), 8.45(1H,d), 7.95(1H,dd), 2.91-2.95(1H,m), 1.30(3H,d), 1.29(3H,d).

Infrared absorption spectrum $\lambda_{max}$ (KBr) cm$^{-1}$: 3320, 1540, 1350, 1300, 1130, 820.

Element anlysis values (calculated as $C_{19}H_{16}N_4O_2S.1/4H_2O$)

|                   | C (%) | H (%) | N (%) | S (%) |
|-------------------|-------|-------|-------|-------|
| Theoretical values| 56.91 | 4.15  | 13.97 | 8.00  |
| Found values      | 57.07 | 3.96  | 13.99 | 8.25  |

2-isopropyl-5(6)-(5-isoquinolylsulfonyl)-7(4)-nitro-1H-benzo[d]imidazole

Melting point: 230–232° C.

Mass spectrometry (m/z): 397 (M+1)

Nuclear magnetic resonance spectrum (DMSO-$d_6$) δ: 9.44(1H,s), 8.74(1H,dd), 8.67(1H,d), 8.55(1H,s), 8.45-8.52 (3H,m), 7.93(1H,d), 3.32-3.34(1H,m), 1.34(3H,s), 1.33(3H,s).

Infrared absorption spectrum $\lambda_{max}$ (KBr) cm$^{-1}$: 1520, 1380, 1320, 620

EXAMPLE 84

4-(5-Isoquinolylsulfanyl)-1,2-di(phenylcarboxamide)benzene 4-(5-Isoquinolylsulfanyl)-1,2-benzendiamine 1.00 g (3.7 mmol) was dissolved in a mixture of hexamethylphosphoramide 15 ml and acetonitril 1.5 ml, benzoyl chloride 1.0 ml was added, and the mixture was stirred for 1 hour at room temperature. The reaction mixture was poured into ice water, neutralized with 50% sodium hydroxide, and extracted with ethyl acetate. The organic layer was washed with saturated sodium chloride, dried over anhydrous sodium sulfate and concentrated under reduced pressure. The residue was crystallized from methanol-ether-hexane mixture, and 4-(5-isoquinolylsulfanyl)-1,2-di(phenylcarboxamide)benzene 1.55 g (87.1%) was obtained.

Melting point: 138–141° C.

Mass spectrometry (m/z): 476 (M+1)

Nuclear magnetic resonance spectrum (DMSO-$d_6$) δ: 10.65(2H,brs), 9.40(1H,s), 8.60(1H,d), 8.19(1H,d), 8.07 (1H,d), 7.88-7.92(5H,m), 7.47-7.74(10H,m), 7.17(1H,dd).

Infrared absorption spectrum $\lambda_{max}$ (KBr) cm$^{-1}$: 1660, 1500, 1470, 710.

EXAMPLE 85

5(6)-(5-Isoquinolylsulfanyl)-2-phenyl-1H-benzo[d] imidazole

A mixture of 4-(5-isoquinolylsulfanyl)-1,2-di (phenylcarboxamide)benzene 1.30 g (2.7 mmol), acetic acid 3.9 ml and hexamethylphosphoramide 17.0 ml was heated with stirring for 2 days at 180° C. Ethyl acetate was added to the reaction solution, the organic layer was washed with saturated sodium bicarbonate, with water and with saturated sodium chloride, dried over anhydrous magnesium sulfate and concentrated under reduced pressure. The resulting residue was dissolved in methanol, 2N hydrochloric acid was added, and the solution was concentrated under reduced pressure, and the residue was crystallized from methanol-ether to give 5(6)-(5-isoquinolylsulfanyl)-2-phenyl-1H-benzo[d]imidazole hydrochloride 650 mg (55.8%).

Melting point: >270° C.

Mass spectrometry (m/z): 354 (M+1)

Nuclear magnetic resonance spectrum (DMSO-$d_6$) δ: 9.81(1H,s), 8.69(1H,d), 8.35-8.45(4H,m), 8.04(1H,d), 7.89 (1H,dd), 7.80(1H,d), 7.65-7.69(4H,m), 7.45(1H,dd).

Infrared absorption spectrum $\lambda_{max}$ (KBr) cm$^1$: 1620, 840, 700.

Element anlysis values (calculated as $C_{25}H_{22}N_3S.2HCl$)

|                   | C (%) | H (%) | N (%) |
|-------------------|-------|-------|-------|
| Theoretical values| 61.97 | 4.02  | 9.86  |
| Found values      | 62.36 | 4.04  | 10.05 |

EXAMPLE 86

4-Chloro-5-(5-isoquinolylsulfanyl)-1,2-di(phenylcarboxamide)benzene

According to the same method in Example 84, 4-chloro-5-(5-isoquinolylsulfanyl)-1,2-di(phenylcarboxamide) benzene 1.19 g (75.2%) was obtained from 4-chloro-5-(5-isoquinolylsulfanyl)-1,2-benzenediamine 1.00 g (3.3 mmol), hexamethylphosphoramide 17.0 ml, acetonitril 1.5 ml and benzoyl chloride 0.9 ml.

Melting point: 200–202° C.

Mass spectrometry (m/z): 510 (M+1)

Nuclear magnetic resonance spectrum (DMSO-$d_6$) δ: 10.00(2H,brs), 9.41(1H,s), 8.61(1H,d), 8.24(1H,d), 7.89-8.01(5H,m), 7.73-7.80(3H,m), 7.41-7.56(6H,m), 7.25 (1H,s).

Infrared absorption spectrum $\lambda_{max}$ (KBr) cm$^{-1}$: 1650, 1520, 1460, 700.

Element anlysis values (calculated as $C_{29}H_{20}ClN_3O_2S.1/4H_2O$)

|  | C (%) | H (%) | N (%) | S (%) |
|---|---|---|---|---|
| Theoretical values | 67.76 | 4.02 | 8.17 | 6.23 |
| Found values | 67.64 | 3.85 | 8.00 | 6.63 |

EXAMPLE 87

6(5)-Chloro-5(6)-(5-isoquinolylsulfanyl)-2-phenyl-1H-benzo[d]imidazole

According to the method in Example 85, 6(5)-chloro-5(6)-(5-isoquinolylsulfanyl)-2-phenyl-1H-benzo[d]imidazole hydrochloride 420 mg (86.3%) was obtained from 4-chloro-5-(5-isoquinolylsulfanyl)-1,2-di(phenylcarboxamide) benzene 500 mg (1.0 mmol), acetic acid 1.5 ml and hexamethylphosphoramide 7.0 ml.

Melting point: >270° C.

Mass spectrometry (m/z): 388 (M+1)

Nuclear magnetic resonance spectrum (DMSO-d$_6$) δ: 9.97(1H,s), 8.73(1H,d), 8.57(1H,d), 8.52(1H,d), 8.28(2H,d), 8.10(1H,d), 7.97–8.00(2H,m), 7.01–7.62(3H,m), 7.36(1H, s).

Infrared absorption spectrum $\lambda_{max}$ (KBr) cm$^{-1}$: 1600, 1450, 1330, 830, 700.

Element anlysis values (calculated as $C_{22}H_{14}ClN_3S.2HCl.3/4H_2O$)

|  | C (%) | H (%) | N (%) | S (%) |
|---|---|---|---|---|
| Theoretical values | 55.70 | 3.72 | 8.86 | 6.76 |
| Found values | 55.58 | 3.49 | 8.67 | 6.95 |

EXAMPLE 88

6(5)-Chloro-5(6)-(5-isoquinolylsulfonyl)-2-phenyl-1H-benzo[d]imidazole

According to the method in Example 47, 6(5)-chloro-5(6)-(5-isoquinolylsulfonyl)-2-phenyl-1H-benzo[d]imidazole 60 mg (19.4%) was obtained from 6(5)-chloro-5(6)-(5-isoquinolylsulfanyl)-2-phenyl-1H-benzo[d]imidazole 350 mg (0.8 mmol), concentrated sulfuric acid 2.0 ml and Beckmann's reagent 3.0 ml.

Mass spectrometry (m/z): 420 (M+1)

Nuclear magnetic resonance spectrum (DMSO-$_6$) δ: 9.47 (1H,s), 8.76(1H,s), 8.75(1H,d), 8.57(1H,d), 8.55(1H,d), 8.22 (1H,d), 8.16(1H,d), 7.97(1H,dd), 7.74(1H,s), 7.59–7.60(3H, m).

Infrared absorption spectrum $\lambda_{max}$ (KBr) cm$^{-1}$: 1620, 1450, 1310, 1150, 1130, 700, 600, 580, 510.

Element anlysis values (calculated as $C_{22}H_{14}ClN_3O_2S.1/4H_2O$)

|  | C (%) | H (%) | N (%) |
|---|---|---|---|
| Theoretical values | 62.26 | 3.44 | 9.90 |
| Found values | 62.27 | 3.65 | 9.67 |

EXAMPLE 89

5(6)-(5-Isoquinolylsulfanyl)-2-trifluoromethyl-1H-benzo[d]imidazole 5-(5-Isoquinolylsulfanyl)-2-nitroaniline 500 mg (1.7 mmol) was dissolved in 4N hydrochloric acid 16 ml, stannous chloride dihydrate 1.73 g (7.7 mmol) and trifluoroacetic acid 370 μl were added, and the mixture was heated with stirring at 130° C. for 15 hours. The reaction mixture was cooled, and the supernatant was discarded, the residue was crystallized with ether, and 5(6)-(5-isoquinolylsulfanyl)-2-trifluoromethyl-1H-benzo[d]imidazole hydrochloride 540 mg (80.2%) was obtained.

Melting point: 74–77° C.

Mass spectrometry (m/z): 346 (M+1)

Nuclear magnetic resonance spectrum (DMSO-d$_6$) δ: 9.78(1H,s), 8.68(1H,d), 8.47(1H,d), 8.39(1H,d), 7.97(1H,d), 7.86(1H,t), 7.76(1H,d), 7.41(1H,d).

Infrared absorption spectrum $\lambda_{max}$ (KBr) cm$^{-1}$: 1640, 1540, 1305, 1150.

EXAMPLE 90

5(6)-(5-Isoquinolylsulfonyl)-2-trifluoromethyl-1H-benzo[d]imidazole

5(6)-(5-Isoquinolylsulfanyl)-2-trifluoromethyl-1H-benzo[d]imidazole 400 mg (0.9 mmol) was dissolved in concentrated sulfuric acid 3.0 ml, Beckmann's reagent 6.0 ml ($K_2Cr_2O_7$ 1 g, $H_2SO_4$ 1 ml, $H_2O$ 9 ml) was added dropwise, and the mixture was stirred overnight at room temperature. After adding water, the reaction mixture was neutralized with 4N sodium hydroxide, and the resulting precipitates were collected and washed with water. The resulting residue was dissolved in methanol, and methanol saturated with hydrogen chloride was added. The solution was concentrated under reduced pressure, the residue was crystallized with acetone, and 5(6)-(5-isoquinolylsulfonyl)-2-trifluoromethyl-1H-benzo[d]imidazole hydrochloride 140 mg (24.3%) was obtained.

Melting point: >270° C.

Mass spectrometry (m/z): 378 (M+1)

Nuclear magnetic resonance spectrum (DMSO-$_6$) δ: 9.66 (1H,s), 8.82(1H,d), 8.68(1H,d), 8.64(1H,d), 8.59(1H,d), 8.54(1H,s), 8.04(1H,s), 7.94–7.88(2H,m).

Infrared absorption spectrum $\lambda_{max}$ (KBr) cm$^{-1}$: 3025, 2975, 1650, 1540, 1320, 1150, 1120, 820, 720, 635, 540.

EXAMPLE 91

5(6)-(5-Isoquinolylsulfonyl)-2-hexyl-1H-benzo[d]imidazole

A mixture of 4-(5-isoquinolylsulfonyl)-1,2-benzenediamine 2.00 g (6.7 mmol), n-valeric acid 3.0 ml, and concentrated hydrochloric acid 27.0 ml was heated and refluxed overnight. The reaction solution was poured into ice water, neutralized with sodium hydroxide, and extracted with ethyl acetate. The organic layer was washed with saturated sodium chloride, dried over anhydrous sodium sulfate and concentrated under reduced pressure. The resulting residue was purified by silica gel column chromatography (ethyl acetate: methanol=9:1), and 5(6)-(5-isoquinolylsulfonyl)-2-hexyl-1H-benzo[d]imidazole 1.31 g (50.0%) was obtained.

Melting point: 72–82° C.

Mass spectrometry (m/z): 394 (M+1)

Nuclear magnetic resonance spectrum (DMSO-$d_6$) δ: 9.43(1H,d), 8.66(1H,dd), 8.62(1H,d), 8.47(1H,d), 8.43(1H,d), 8.14(1H,d), 7.92(1H,dd), 7.69(1H,dd), 7.60(1H,d), 2.80(2H,t), 1.71(2H,tt), 1.22–1.30(6H,m), 0.81(3H,t).

Infrared absorption spectrum $\lambda_{max}$ (KBr) cm$^{-1}$: 2930, 1620, 1310, 1120, 630.

Element anlysis values (calculated as $C_{22}H_{23}N_3O_2S$)

|  | C (%) | H (%) | N (%) |
|---|---|---|---|
| Theoretical values | 67.15 | 5.87 | 10.68 |
| Found values | 66.97 | 5.78 | 10.31 |

EXAMPLE 92

2-Cyclopropyl-5(6)-(5-isoquinolylsulfanyl)-1H-benzo[d]imidazole 4-(5-Isoquinolylsulfanyl)-1,2-benzenediamine 1.00 g (3.7 mmol) was dissolved in 4N hydrochloric acid 18 ml, cyclopropane carboxylic acid 0.8 ml was added, and the mixture was heated and refluxed overnight. After adding 40% sodium hydroxide to neutralize, the reaction mixture was extracted with ethyl acetate. The organic layer was washed with water and with saturated sodium chloride, dried over anhydrous sodium sulfate and concentrated under reduced pressure. The resulting residue was crystallized with ethyl acetate-hexane, and 2-cyclopropyl-5(6)-(5-isoquinolylsulfanyl)-1H-benzo[d]imidazole 1.07 g (90.1%) was obtained.

Mass spectrometry (m/z): 318 (M+1)

Nuclear magnetic resonance spectrum (DMSO-$d_6$) δ: 9.34(1H,s), 8.56(1H,d), 8.30(1H,s), 8.06(1H,d), 8.02(1H,d), 7.57(1H,dd), 7.44–7.49(3H,m), 7.18(1H,d).

Infrared absorption spectrum $\lambda_{max}$ (KBr) cm$^{-1}$: 1615, 1540, 1450, 820.

Element anlysis values (calculated as $C_{19}H_{15}N_3S.1/4H_2O$)

|  | C (%) | H (%) | N (%) | S (%) |
|---|---|---|---|---|
| Theoretical values | 70.89 | 4.85 | 13.05 | 9.96 |
| Found values | 70.56 | 5.17 | 12.90 | 9.92 |

EXAMPLE 93

2-Cyclopropyl-5(6)-(5-isoquinolylsulfonyl)-1H-benzo[d]imidazole

According to the method in Example 91, from a mixture of 4-(5-isoquinolylsulfonyl)-1,2-benzenediamine trihydrochloride 300 mg (0.7 mmol), cyclopropane carboxylic acid 0.5 ml and 4N hydrochloric acid 6.0 ml, 2-cyclopropyl-5(6)-(5-isoquinolylsulfonyl)-1H-benzo[d]imidazole 180 mg (70.2%) was obtained as powder.

Melting point: 240–244° C.

Mass spectrometry (m/z): 350 (M+1)

Nuclear magnetic resonance spectrum (DMSO-$d_6$) δ: 9.43(1H,s), 8.65(1H,d), 8.63(1H,d), 8.47(1H,d), 8.41(1H,d), 8.08(1H,s), 7.91(1H,dd), 7.68(1H,d), 7.55(1H,d).

Infrared absorption spectrum $\lambda_{max}$ (KBr) cm$^{-1}$: 1620, 1540, 1310, 1120, 630.

Element anlysis values (calculated as $C_{19}H_{15}N_3O_2S.1/4H_2O$)

|  | C(%) | H(%) | N(%) | S(%) |
|---|---|---|---|---|
| Theoretical values | 64.48 | 4.41 | 11.87 | 9.06 |
| Found values | 64.39 | 4.63 | 11.55 | 9.25 |

EXAMPLE 94

2-Cyclobutyl-5(6)-(5-isoquinolylsulfonyl)-1H-benzo[d]imidazole

According to the method in Example 91, from a mixture of 4-(5-isoquinolylsulfonyl)-1,2-benzenediamine 1.20 g (4.0 mmol), cyclobutane carboxylic acid 2.0 ml and concentrated hydrochloric acid 20.0 ml, 2-cyclobutyl-5(6)-(5-isoquinolylsulfonyl)-1H-benzo[d]imidazole 640 mg (44.0%) was obtained.

Melting point: 203–206° C.

Mass spectrometry (m/z): 364 (M+1)

Nuclear magnetic resonance spectrum (DMSO-$d_6$) δ: 9.43(1H,s), 8.66(1H,d), 8.63(1H,d), 8.47(1H,d), 8.42(1H,d), 8.16(1H,s), 7.90(1H,dd), 7.71(1H,dd), 7.60(1H,d), 3.68–3.75(1H,m), 2.28–2.39(4H,m), 1.98–2.07(1H,m), 1.85–1.92(1H,m).

Infrared absorption spectrum $\lambda_{max}$ (KBr) cm$^{-1}$: 1620, 1320, 1130, 630.

Element anlysis values (calculated as $C_{20}H_{17}N_3O_2S$)

|  | C(%) | H(%) | N(%) | S(%) |
|---|---|---|---|---|
| Theoretical values | 66.10 | 4.71 | 11.56 | 8.82 |
| Found values | 65.93 | 4.75 | 11.51 | 8.90 |

EXAMPLE 95

2-Cyclopentyl-5(6)-(5-isoquinolylsulfonyl)-1H-benzo[d]imidazole

According to the method in Example 91, from a mixture of 4-(5-isoquinolylsulfonyl)-1,2-benzenediamine 1.20 g (4.0 mmol), cyclopentane carboxylic acid 5.0 ml and concentrated hydrochloric acid 20.0 ml, 2-cyclopentyl-5(6)-(5-isoquinolylsulfonyl)-1H-benzo[d]imidazole 1.24 g (82.1%) was obtained.

Melting point: 249–253° C.

Mass spectrometry (m/z): 378 (M+1)

Nuclear magnetic resonance spectrum (DMSO-$d_6$) δ: 9.43(1H,s), 8.66(1H,d), 8.63(1H,d), 8.47(1H,d), 8.41(1H,d), 8.14(1H,s), 7.91(1H,dd), 7.71(1H,dd), 7.59(1H,d), 3.24–3.31(1H,m), 1.58–2.04(8H,m).

Infrared absorption spectrum $\lambda_{max}$ (KBr) cm$^{-1}$: 2950, 1620, 1450, 1310, 1280, 1130, 630.

Element anlysis values (calculated as $C_{22}H_{19}N_3O_2S$)

|  | C(%) | H(%) | N(%) |
|---|---|---|---|
| Theoretical values | 66.82 | 5.07 | 11.13 |
| Found values | 66.77 | 5.08 | 11.18 |

EXAMPLE 96

2-Cyclohexyl-5(6)-(5-isoquinolylsulfonyl)-1H-benzo[d]imidazole

According to the method in Example 91, from a mixture of 4-(5-isoquinolylsulfonyl)-1,2-benzenediamine 1.00 g (3.3 mmol), cyclohexane carboxylic acid 2.0 ml and concentrated hydrochloric acid 15.0 ml, 2-cyclohexyl-5(6)-(5-isoquinolylsulfonyl)-1H-benzo[d]imidazole 890 mg (69.1%) was obtained.

Melting point: 218–223° C.

Mass spectrometry (m/z): 392 (M+1)

Nuclear magnetic resonance spectrum (DMSO-$_6$) δ: 9.43 (1H,s), 8.63–8.66(2H,m), 8.42(1H,d), 8.13(1H,d), 7.91(1H,dd), 7.68(1H,dd), 7.59(1H,d), 1.95(1H,brs), 1.73–1.76(2H,m),1.64–1.67(1H,m), 1.51–1.59(2H,m), 1.33–1.38(2H,m), 1.20–1.25(2H,m).

Infrared absorption spectrum $v_{max}$ (KBr) cm$^{-1}$: 2930, 1620, 1310, 1130, 630.

Element anlysis values (calculated as $C_{22}H_{21}N_3O_2S.1/4H_2O$)

|  | C(%) | H(%) | N(%) |
|---|---|---|---|
| Theoretical values | 66.73 | 5.47 | 10.61 |
| Found values | 66.37 | 5.35 | 10.36 |

EXAMPLE 97

2-Cycloheptyl-5(6)-(5-isoquinolylsulfonyl)-1H-benzo[d]imidazole

According to the method in Example 91, from a mixture of 4-(5-isoquinolylsulfonyl)-1,2-benzenediamine 1.00 g (3.3 mmol), cycloheptane carboxylic acid 2.5 ml and concentrated hydrochloric acid 15.0 ml, 2-cycloheptyl-5(6)-(5-isoquinolylsulfonyl)-1H-benzo[d]imidazole 800 mg (59.3%) was obtained.

Melting point: 187–189° C.

Mass spectrometry (m/z): 406 (M+1)

Nuclear magnetic resonance spectrum (DMSO-d$_6$) δ: 9.43(1H,s), 8.65(1H,dd), 8.63(1H,d), 8.47(1H,d), 8.42(1H,d), 8.14(1H,d), 7.91(1H,dd), 7.70(1H,dd), 7.60(1H,d), 3.03–3.06(1H,m),1.95–2.08(2H,m), 1.45–1.81(10H,m).

Infrared absorption spectrum $v_{max}$ (KBr) cm$^{-1}$: 2950, 1620, 1520, 1450, 1310, 1280, 1130, 630.

Element anlysis values (calculated as $C_{23}H_{23}N_3O_2S$)

|  | C(%) | H(%) | N(%) |
|---|---|---|---|
| Theoretical values | 68.12 | 5.72 | 10.36 |
| Found values | 68.35 | 5.63 | 10.31 |

EXAMPLE 98

5-(5-Isoquinolylsulfanyl)-6-nitro-2,3-dihydro-1H-benzo[d]imidazole-2-one

To a DMF solution 15 ml of 5-fluoro-6-nitrobenzoimidazolinone 500 mg (2.5 mmol) and 5-isoquinolinethiol 450 mg (2.8 mmol), potassium carbonate 550 mg (4.0 mmol) was added, and the mixture was heated with stirring for 2 hours at 100° C. After adding water, the reaction mixture was extracted with ethyl acetate. The organic layer was washed with a saturated water solution of sodium chloride, dried over anhydrous magnesium sulfate, and concentrated under reduced pressure. The residue was crystallized from methanol, and 5-(5-isoquinolylsulfanyl)-6-nitro-2,3-dihydro-1H-benzo[d]imidazol-2-one 346 mg (40.3%) was obtained.

Melting point: >270° C.

Nuclear magnetic resonance spectrum (DMSO-d$_6$) δ: 9.47(1H,s), 8.55(1H,d), 8.41(1H,d), 8.26(1H,d), 7.89–7.84(2H,m), 7.80(1H,s), 5.93(1H,s).

Infrared absorption spectrum $\lambda_{max}$ (KBr) cm$^{-1}$: 1710, 1485, 1310.

EXAMPLE 99

5-(5-Isoquinolylsulfonyl)-6-nitro-2,3-dihydro-1H-benzo[d]imidazol-2-one 5-(5-Isoquinolylsulfanyl)-6-nitro-2,3-dihydro-1H-benzo[d]imidazol-2-one 340 mg (1.0 mmol) was dissolved in concentrated sulfuric acid 3.5 ml, Beckmann's reagent 7.0 ml ($K_2Cr_2O_7$ 1 g, $H_2SO_4$ 1 ml, $H_2O$ 9 ml) was added dropwise, and the mixture was stirred overnight at room temperature. After adding water, the resulting precipitates were collected and washed with water, and 5-(5-isoquinolylsulfonyl)-6-nitro-2,3-dihydro-1H-benzo[d]imidazol-2-one sulfate 270 mg (72.8%) was obtained.

Melting point: >270° C.

Mass spectrometry (m/z): 371 (M+1)

Nuclear magnetic resonance spectrum (DMSO-d$_6$) δ: 9.52(1H,s), 8.66(1H,d), 8.54(1H,d), 8.40(1H,d), 8.22(1H,d), 7.92(1H,t), 7.83(1H,s), 7.62(1H,s).

Infrared absorption spectrum $\lambda_{max}$ (KBr) cm$^{-1}$: 1720, 1530, 1500, 1340, 1320, 1305, 1235, 825.

Element anlysis values (calculated as $C_{16}H_{10}N_4O_5S.3/4H_2SO_4.H_2O$)

|  | C(%) | H(%) | N(%) | S(%) |
|---|---|---|---|---|
| Theoretical values | 41.60 | 2.95 | 12.13 | 12.15 |
| Found values | 41.78 | 2.53 | 11.80 | 12.46 |

EXAMPLE 100

5-(5-Isoquinolylsulfanyl)-6-nitro-2,3-dihydro-benzo[d][1,3]thiazol-2-one

To a DMF solution 12 ml of 5-chloro-6-nitro-2-benzothiazolinone 500 mg (2.2 mmol) and 5-isoquinolylthiol 390 mg (2.4 mmol), potassium carbonate 450 mg (3.3 mmol) was added, and the mixture was heated with stirring for 4 hours at 140° C. After adding water, the resulting precipitates were collected and washed with water and ether, and 5-(5-isoquinolylsulfanyl)-6-nitro-2,3-dihydro-benzo[d][1,3]thiazol-2-one 774 mg (91.2%) was obtained.

Melting point: >270° C.

Nuclear magnetic resonance spectrum (DMSO-d$_6$) δ: 9.45(1H,s), 8.53(1H,d), 8.39(1H,d), 8.24(1H,d), 8.20(1H,s), 7.90(1H,d), 7.84(1H,t), 5.70(1H,s).

Infrared absorption spectrum $\lambda_{max}$ (KBr) cm$^{-1}$: 1630, 1560, 1450, 1320, 1280.

EXAMPLE 101

5-(5-Isoquinolylsulfinyl)-6-nitro-2,3-dihydro-benzo[d][1,3]thiazol-2-one 5-(5-Isoquinolylsulfanyl)-6-nitro-2,3-dihydro-benzo[d][1,3]thiazol-2-one 300 mg (0.8 mmol) was dissolved in acetic acid 20 ml, 35% hydrogen peroxide 15 ml was added, and the mixture was stirred for 15 hours at room temperature. Saturated sodium thiosulfate was added to the reaction solution, the resulting precipitates were collected and washed with water, and 5-(5-isoquinolylsulfinyl)-6-nitro-2,3-dihydro-benzo[d][1,3]thiazol-2-one 190 mg (61.6%) was obtained.

Melting point: >270° C.

Nuclear magnetic resonance spectrum (DMSO-$d_6$) δ: 9.47(1H,s), 8.84(1H,s), 8.78(1H,d), 8.63(1H,d), 8.32(1H,d), 8.13(1H,s), 7.65–7.63(2H,m).

Infrared absorption spectrum $\lambda_{max}$ (KBr) cm$^{-1}$: 1710, 1520, 1320, 1185, 1110.

Element anlysis values (calculated as $C_{16}H_9N_3O_4S_2 \cdot H_2O$)

|  | C(%) | H(%) | N(%) | S(%) |
|---|---|---|---|---|
| Theoretical values | 49.35 | 2.85 | 10.79 | 16.47 |
| Found values | 49.38 | 2.74 | 10.47 | 16.36 |

EXAMPLE 102

5-(5-Isoquinlylsulfanyl)-6-nitro-2,3-dihydro-benzo[d][1,3]oxazol-2-one

5-Isoquinolinethiol 500 mg (3.1 mmol) was dissolved in DMF 30 ml, 5-chloro-6-nitro-2-benzooxazolinone 670 mg (3.1 mmol) and potassium carbonate 1.29 g (9.3 mmol) were added, and the mixture was heated with stirring overnight at 130° C. The reaction mixture was concentrated under reduced pressure, the residue was washed with water and chloroform, and 5-(5-isoquinlylsulfanyl)-6-nitro-2,3-dihydro-benzo[d][1,3]oxazol-2-one 400 mg (38.0%) was obtained.

Melting point: 158–170° C.

Mass spectrometry (m/z): 340 (M+1)

Nuclear magnetic resonance spectrum (DMSO-$d_6$) δ: 9.45(1H,s), 8.53(1H,d), 8.38(1H,dd), 7.88(1H,d), 7.84(1H,t), 7.68(1H,s), 5.53(1H,s).

Infrared absorption spectrum $\lambda_{max}$ (KBr) cm$^{-1}$: 1700, 1565, 1460, 1310, 1270.

EXAMPLE 103

5-(5-Isoquinolylsulfonyl)-6-nitro-2,3-dihydro-benzo[d][1,3]oxazol-2-one 5-(5-Isoquinolylsulfanyl)-6-nitro-2,3-dihydro-benzo[d][1,3]oxazole-2-one 140 mg (0.4 mmol) was dissolved in concentrated sulfuric acid 1.5 ml, Beckmann's reagent 3.0 ml ($K_2Cr_2O_7$ 1 g, $H_2SO_4$ 1 ml, $H_2O$ 9 ml) was added dropwise, and the mixture was stirred for 4 hours at 0° C. The resulting precipitates were collected and washed with water, and 5-(5-isoquinolylsulfonyl)-6-nitro-2,3-dihydro-benzo[d][1,3]oxazol-2-one sulfate 50 mg (30.3%) was obtained.

Melting point: >270° C.

Mass spectrometry (m/z): 372 (M+1)

Nuclear magnetic resonance spectrum (DMSO-$d_6$) δ: 9.58(1H,s), 8.69(1H,d), 8.61(1H,d), 8.48(1H,d), 8.30(1H,d), 8.22(1H,s), 7.99–7.95(2H,m).

Infrared absorption spectrum $\lambda_{max}$ (KBr) cm$^{-1}$: 1800, 1540, 1490, 1360, 1340, 1140, 830.

Element anlysis values (calculated as $C_{16}H_9N_3O_6S \cdot 3/2 H_2SO_4 \cdot H_2O$)

|  | C(%) | H(%) | S(%) |
|---|---|---|---|
| Theoretical values | 38.09 | 2.80 | 9.53 |
| Found values | 37.77 | 2.42 | 9.14 |

EXAMPLE 104

6-(5-Isoquinolylsulfanyl)-5-nitro-2,3-dihydro-benzo[d][1,3]oxazol-2-one

5-Isoquinolinethiol 500 mg (3.1 mmol) was dissolved in DMF 20 ml, 5-fluoro-6-nitro-benzooxazolinone 670 mg (3.1 mmol) and potassium carbonate 1.29 g (9.3 mmol) were added, and the mixture was heated with stirring overnight at 130° C. The reaction mixture was concentrated under reduced pressure, acetone 20 ml was added to the residue, and insoluble materials were filtered. Chloroform 50 ml was added to the organic layer, the resulting precipitates were collected to give 6-(5-isoquinolylsulfanyl)-5-nitro-2,3-dihydro-benzo[d][1,3]oxazol-2-one 400 mg (38.0%).

Melting point: 255–260° C.

Mass spectrometry (m/z): 340 (M+1)

Nuclear magnetic resonance spectrum (DMSO-$d_6$) δ: 9.42(1H,d), 8.52(1H,d), 8.30(1H,d), 8.09(1H,dd), 7.85(1H,d), 7.79(1H,d), 7.77(1H,d), 5.92(1H,s).

Infrared absorption spectrum $\nu_{max}$ (KBr) cm$^{-1}$: 1690, 1500, 1280.

EXAMPLE 105

6-(5-Isoquinolylsulfonyl)-5-nitro-2,3-dihydro-benzo[d][1,3]oxazole-2-one 6-(5-Isoquinolylsulfanyl)-5-nitro-2,3-dihydro-benzo[d][1,3]oxazole-2-one 250 mg (0.7 mmol) was dissolved in concentrated sulfuric acid 2.5 ml, Beckmann's reagent 5.0 ml ($K_2Cr_2O_7$ 1 g, $H_2SO_4$ 1 ml, $H_2O$ 9 ml) was added dropwise, and the mixture was stirred for 6 hours at room temperature. The reaction solution was neutralized with 4N sodium hydroxide, and the resulting precipitates were collected and washed with water, and 6-(5-isoquinolylsulfonyl)-5-nitro-2,3-dihydro-benzo[d][1,3]oxazol-2-one 110 mg (39.1%) was obtained.

Melting point:>270° C.

Mass spectrometry (m/z): 372 (M+1)

Nuclear magnetic resonance spectrum (DMSO-$d_6$) δ: 9.51(1H,s), 8.67(1H,d), 8.57(1H,d), 8.45–8.43(3H,m), 8.33(1H,d), 7.95(1H,t), 7.80(1H,s).

Infrared absorption spectrum $\nu_{max}$ (KBr) cm$^{-1}$: 1790, 1620, 1550, 1485, 1370, 1320, 1270, 1135.

Element anlysis values (calculated as $C_{16}H_9N_3O_6S \cdot H_2O$)

|  | C(%) | H(%) | N(%) | S(%) |
|---|---|---|---|---|
| Theoretical values | 49.35 | 2.85 | 10.79 | 8.24 |
| Found values | 49.39 | 2.35 | 10.37 | 8.50 |

EXAMPLE 106

6-(5-Isoquinolylsulfanyl)-2-methylbenzo[d][1,3]oxazole

Acetic anhydride 0.6 ml was added to 2-amino-5-(5-isoquinolylsulfanyl)phenol 210 mg (0.8 mmol), and the mixture was heated for 1 hour at 200° C. Ethyl acetate was added to the reaction solution, and the organic layer was washed with 0.5 N sodium hydroxide, water and saturated sodium chloride. The organic layer was dried over anhydrous sodium sulfate and concentrated under reduced pressure, and the resulting residue was purified by silica gel column chromatography (NH-silica gel, hexane:ethyl acetate=1:1), and 6-(5-isoquinolylsulfanyl)-2-methylbenzo[d][1,3]oxazole 120 mg (50.6%) was obtained.

Melting point: 140–142° C.

Mass spectrometry (m/z): 293 (M+1)

Nuclear magnetic resonance spectrum (DMSO-$d_6$) δ: 9.23(1H,s), 8.52(1H,d), 8.04(1H,d), 7.88(1H,d), 7.69(1H,d), 7.48–7.53(2H,m), 7.30(1H,d), 7.24(1H,dd), 2.56(3H,s).

Infrared absorption spectrum $v_{max}$ (KBr) cm$^{-1}$: 1620, 1570, 1455, 1420, 1260, 820, 750.

Element anlysis values (calculated as $C_{17}H_{12}N_2OS$)

|  | C(%) | H(%) | S(%) |
|---|---|---|---|
| Theoretical values | 69.84 | 4.14 | 10.97 |
| Found values | 69.83 | 4.32 | 10.57 |

EXAMPLE 107

5-(5-Isoquinolylsulfanyl)-2-methyl-6-nitrobenzo[d][1,3]thiazole

5-Isoquinolinethiol 250 mg (1.5 mmol) was dissolved in DMF 10 ml, 5-fluoro-2-methyl-6-nitrobenzothiazole 330 mg (1.5 mmol) and potassium carbonate 650 mg (4.7 mmol) were added, and the mixture was stirred for 1 hour at room temperature. The reaction mixture was concentrated under reduced pressure, the residue was crystallized from ether, and 5-(5-isoquinolylsulfanyl)-2-methyl-6-nitrobenzo[d][1,3]thiazole 180 mg (33.1%) was obtained.

Melting point: 217–220° C.

Mass spectrometry (m/z): 354 (M+1)

Nuclear magnetic resonance spectrum (DMSO-$d_6$) δ: 9.33(1H,s), 8.80(1H,s), 8.51(1H,d), 8.16–8.17(2H,m), 7.96(1H,d), 7.71(1H,dd), 7.00(1H,s), 2.72(3H,s).

Infrared absorption spectrum $v_{max}$ (KBr) cm$^{-1}$: 1540, 1500, 1420, 1335, 1300.

Element anlysis values (calculated as $C_{17}H_{11}N_3O_2S \cdot 1/2H_2O$)

|  | C(%) | H(%) | N(%) | S(%) |
|---|---|---|---|---|
| Theoretical values | 56.34 | 3.34 | 11.59 | 17.69 |
| Found values | 56.06 | 3.04 | 11.35 | 17.68 |

EXAMPLE 108

5(6)-(5-Isoquinolylsulfanyl)-4(7)-nitro-1H-benzo[d][1,2,3]triazole

5-Isoquinolinethiol 500 mg (3.1 mmol) was dissolved in DMF 20 ml, 4-fluoro-5-nitrobenzotriazole 560 mg (3.1 mmol) and potassium carbonate 1.29 g (9.3 mmol) were added, and the mixture was heated with stirring for 20 hours at 80° C. The reaction mixture was concentrated under reduced pressure, acetone 10 ml was added to the residue, and insoluble materials were filtered. Ethyl acetate 10 ml was added to the organic layer, the precipitates were collected, and 5(6)-(5-isoquinolylsulfanyl)-4(7)-nitro-1H-benzo[d][1,2,3]triazole 1.09 g (100.0%) was obtained.

Melting point: >270° C

Mass spectrometry (m/z): 324 (M+1)

Nuclear magnetic resonance spectrum (DMSO-$d_6$) δ: 9.39(1H,s), 8.51(1H,d), 8.21(1H,d), 7.93–7.90(2H,m), 7.74–7.70(2H,m), 6.47(1H,d).

Infrared absorption spectrum $v_{max}$ (KBr) cm$^{-1}$: 1500, 1300, 1250, 915, 825, 760.

EXAMPLE 109

5(6)-(5-Isoquinolylsulfonyl)-4(7)-nitro-1H-benzo[d][1,2,3]triazole

5(6)-(5-isoquinolylsulfanyl)-4(7)-nitro-1H-benzo[d][1,2,3]triazole 300 mg (0.9 mmol) was dissolved in concentrated sulfuric acid 3.0 ml, Beckmann's reagent 6.0 ml ($K_2Cr_2O_7$ 1 g, $H_2SO_4$ 1 ml, $H_2O$ 9 ml) was added dropwise, and the mixture was stirred for 1 day at room temperature. The reaction solution was neutralized with 4N sodium hydroxide, and the resulting precipitates were collected and washed with water, and 5(6)-(5-isoquinolylsulfonyl)-4(7)-nitro-1H-benzo[d][1,2,3]triazole 210 mg (64.0%) was obtained.

Melting point: >270° C.

Mass spectrometry (m/z): 356 (M+1)

Nuclear magnetic resonance spectrum (DMSO-$d_6$) δ: 9.51(1H,s), 8.67(1H,d), 8.61–8.58(2H,m), 8.33–8.28(2H,m), 8.22(1H,d), 7.98(1H,t).

Infrared absorption spectrum $v_{max}$ (KBr) cm$^{-1}$: 3100, 1620, 1550, 1360, 1320, 1140, 1120, 820, 740, 640.

Element anlysis values (calculated as $C_{15}H_9N_3O_4S \cdot 1/2H_2O$)

|  | C(%) | H(%) | N(%) | S(%) |
|---|---|---|---|---|
| Theoretical values | 49.45 | 2.84 | 19.22 | 8.80 |
| Found values | 46.66 | 2.48 | 19.16 | 9.29 |

EXAMPLE 110

6-(5-Isoquinolylsulfanyl)quinoxaline 4-(5-Isoquinolylsulfanyl)-1,2-benzenediamine 200 mg (0.7 mmol) was dissolved in water 10 ml, a water solution 6 ml of glyoxal-sodium bisulfite hydrate 580 mg (2.3 mmol) was added, and the mixture was stirred for 1 hour at 80° C. Potassium carbonate was added to the reaction solution to alkalize the solution, and the solution was extracted with ethyl acetate. The organic layer was washed with saturated sodium chloride, and concentrated under reduced pressure. The resulting residue was purified by silica gel column chromatography (chloroform:acetone=1:10), and 6-(5-isoquinolylsulfanyl)quinoxaline 90 mg (41.2%) was obtained.

Melting point: 143–145° C.

Mass spectrometry (m/z): 290 (M+1)

Nuclear magnetic resonance spectrum (DMSO-$d_6$) δ: 9.45(1H,s), 8.83(1H,d), 8.35(1H,d), 8.20(1H,d), 8.01(1H,d), 7.98(1H,s), 7.81(1H,dd), 7.62(1H,dd), 7.45(1H,d).

Infrared absorption spectrum $v_{max}$ (KBr) cm$^{-1}$: 1600, 1480, 1020, 880, 830.

Element anlysis values (calculated as $C_{17}H_{13}N_3S.1/4H_2O$)

|  | C(%) | H(%) | N(%) | S(%) |
| --- | --- | --- | --- | --- |
| Theoretical values | 69.48 | 3.94 | 14.30 | 10.91 |
| Found values | 69.64 | 3.80 | 14.47 | 10.92 |

EXAMPLE 111

6-(5-Isoquinolylsulfanyl)-7-nitroquinoxaline

A mixture of 5-isoquinolinethiol 220 mg (1.4 mmol), 6-fluoro-7-nitroquinoxaline 260 mg (1.4 mmol), potassium carbonate 380 mg (2.7 mmol) and DMF 3 ml was stirred for 2 hours at 100° C. The reaction solution was poured into water, the precipitates were collected and washed with water, and 6-(5-isoquinolylthio)-7-nitroquinoxaline 410 mg (90.4%) was obtained.

Melting point: 222–225° C.

Mass spectrometry (m/z): 335 (M+1)

Nuclear magnetic resonance spectrum (DMSO-$d_6$) δ: 9.36(1H,s), 9.01(1H,s), 8.80(1H,d), 8.71(1H,d), 8.52(1H,d), 8.22(1H,d), 8.20(1H,s), 7.97(1H,d), 7.95(1H,d), 7.12(1H,s).

Infrared absorption spectrum $v_{max}$ (KBr) cm$^{-1}$: 1600, 1540, 1340, 1200, 830.

Element anlysis values (calculated as $C_{17}H_{10}N_4O_2S.1/8H_2O$)

|  | C(%) | H(%) | N(%) | S(%) |
| --- | --- | --- | --- | --- |
| Theoretical values | 60.66 | 3.07 | 16.64 | 9.53 |
| Found values | 60.64 | 2.99 | 16.67 | 9.39 |

EXAMPLE 112

6-(5-Isoquinolylsulfonyl)quinoxaline

To a suspension of 4-(5-Isoquinolylsulfonyl)-1,2-benzenediamine 300 mg (1.0 mmol) in water, a 40% glyoxal solution 450 mg (3.1 mmol) and sodium bisulfite 650 mg (3.1 mmol) and water 8 ml were added, and the mixture was heated with stirring for 2 hours at 80° C. The reaction mixture was alkalized with 1N sodium hydroxide, and the solution was extracted with ethyl acetate. The organic layer was washed with saturated sodium chloride, and dried over anhydrous magnesium sulfate, and concentrated under reduced pressure. The resulting residue was purified by silica gel column chromatography (chloroform:acetone= 5:1), and 6-(5-isoquinolylsulfonyl)quinoxaline 210 mg (66.3%) was obtained.

Melting point: 187–189° C.

Nuclear magnetic resonance spectrum (DMSO-$d_6$) δ: 9.46(1H,s), 9.08(2H,d), 8.83(1H,d), 8.82(1H,s), 8.65(1H,d), 8.56(1H,d), 8.43(1H,d), 8.24(2H,s), 7.98(1H,dd).

Infrared absorption spectrum $v_{max}$ (KBr) cm$^{-1}$: 1620, 1490, 1310, 1140, 1120, 700.

Element anlysis values (calculated as $C_{17}H_{11}N_3O_2S$)

|  | C(%) | H(%) | N(%) | S(%) |
| --- | --- | --- | --- | --- |
| Theoretical values | 63.54 | 3.45 | 13.08 | 9.98 |
| Found values | 63.51 | 3.51 | 13.23 | 9.80 |

EXAMPLE 113

2,3-Dimethyl-6-(5-isoquinolylsulfonyl)quinoxaline

To a mixture of 4-(5-isoquinolylsulfonyl)benzenediamine 500 mg (1.7 mmol) and ethanol 10 ml, 2,3-butanedione 1.2 ml was added, and the mixture was heated with stirring for 2 hours at 90° C. The reaction mixture was concentrated under reduced pressure, and ether was added to the resulting residue to crystallize. The crystals were filtered, and 2,3-dimethyl-6-(5-isoquinolylsulfonyl)quinoxaline 490 mg (84.7%) was obtained.

Melting point: 198–200° C.

Mass spectrometry (m/z): 350 (M+1)

Nuclear magnetic resonance spectrum (DMSO-$d_6$) δ: 9.44(1H,s), 8.79(1H,d), 8.64(1H,d), 8.62(1H,d), 8.53(1H,d), 8.40(1H,d), 8.09(1H,dd), 8.07(1H,d), 7.96(1H,dd), 2.65(3H, s), 2.64(3H,s).

Infrared absorption spectrum $v_{max}$ (KBr) cm$^{-1}$: 1620, 1400, 1320, 1135, 830.

Element anlysis values (calculated as $C_{19}H_{15}N_3O_2S.1/2H_2O$)

|  | C(%) | H(%) | N(%) | S(%) |
| --- | --- | --- | --- | --- |
| Theoretical values | 63.67 | 4.50 | 11.72 | 8.95 |
| Found values | 63.82 | 4.29 | 12.05 | 8.79 |

EXAMPLE 114

2,3-Diphenyl-6-(5-isoquinolylsulfonyl)quinoxaline

According to the method in Example 113, 2,3-diphenyl-6-(5-isoquinolylsulfonyl)quinoxaline 620 mg (78.4%) was obtained from 4-(5-isoquinolylsulfonyl)-1,2-benzenediamine 500 mg (1.7 mmol), ethanol 50 ml and benzyl 700 mg (3.4 mmol).

Melting point: 219–222° C.

Mass spectrometry (m/z): 474 (M+1)

Nuclear magnetic resonance spectrum (DMSO-$d_6$) δ: 9.30(1H,s), 8.83(1H,d), 8.81(1H,dd), 8.62(1H,d), 8.48(1H, d), 8.25(1H,d), 8.23(1H,d), 8.16(1H,dd), 7.81(1H,dd), 7.46–7.48(4H,m), 7.30–7.40(6H,m).

Infrared absorption spectrum $v_{max}$ (KBr) cm$^{-1}$: 1620, 1310, 1150, 1130.

Element anlysis values (calculated as $C_{29}H_{19}N_3O_2S.1/2H_2O$)

|  | C(%) | H(%) | N(%) | S(%) |
| --- | --- | --- | --- | --- |
| Theoretical values | 72.18 | 4.18 | 8.70 | 6.64 |
| Found values | 72.24 | 4.45 | 8.85 | 6.59 |

EXAMPLE 115

7-(5-Isoquinolylsulfonyl)-1,2,3,4-tetrahydrophenazine

According to the method in Example 113, 7-(5-isoquinolylsulfonyl)-1,2,3,4-tetrahydrophenazine 200 mg (31.4%) was obtained from 4-(5-isoquinolylsulfonyl)-1,2-benzenediamine 500 mg (1.7 mmol), ethanol 50 ml and 1,2-cyclohexanedione 380 mg (3.4 mmol).

Melting point: 196–198° C.

Mass spectrometry (m/z): 376 (M+1)

Nuclear magnetic resonance spectrum (DMSO-$d_6$) δ: 9.28(1H,s), 8.76(1H,dd), 8.64(1H,d), 8.59(1H,d), 8.43(1H,d), 8.23(1H,d), 8.05(1H,dd), 8.01(1H,d), 7.79(1H,dd).

Infrared absorption spectrum $v_{max}$ (KBr) cm$^{-1}$: 2950, 1620, 1320, 1130.

Element anlysis values (calculated as $C_{21}H_{17}N_3O_2S.1/4H_2O$)

|  | C(%) | H(%) | N(%) | S(%) |
| --- | --- | --- | --- | --- |
| Theoretical values | 66.38 | 4.64 | 11.06 | 8.44 |
| Found values | 66.13 | 4.97 | 10.81 | 8.04 |

EXAMPLE 116

6-Chloro-7-(5-isoquinolylsulfonyl)-2,3-dimethylquinoxaline

According to the method in Example 113, 6-chloro-7-(5-isoquinolylsulfonyl)-2,3-dimethylquinoxaline 40 mg (72.9%) was obtained from 4-(5-isoquinolylsulfonyl)-1,2-benzenediamine 50 mg (0.2 mmol), ethanol 5 ml and 2,3-butanedione 70 mg (0.8 mmol).

Melting point: 231–233° C.

Mass spectrometry (m/z): 384 (M+1)

Nuclear magnetic resonance spectrum (DMSO-$d_6$) δ: 9.29(1H,s), 9.21(1H,s), 8.86(1H,d), 8.51(1H,d), 8.27(1H,d), 8.22(1H,d), 7.95(1H,s), 7.82(1H,dd), 2.78(3H,s), 2.74(3H,s).

Infrared absorption spectrum $v_{max}$ (KBr) cm$^{-1}$: 1610, 1400, 1320, 1160, 1140, 840.

Element anlysis values (calculated as $C_{19}H_{14}ClN_3O_2S$)

|  | C(%) | H(%) | N(%) | S(%) |
| --- | --- | --- | --- | --- |
| Theoretical values | 59.45 | 3.68 | 10.95 | 8.35 |
| Found values | 59.50 | 3.80 | 10.76 | 8.52 |

EXAMPLE 117

6-Chloro-7-(5-isoquinolylsulfonyl)-2,3-diphenylquinoxaline

According to the method in Example 113, 6-chloro-7-(5-isoquinolylsulfonyl)-2,3-diphenylquinoxaline 60 mg (80.1%) was obtained from 4-(5-isoquinolylsulfonyl)-1,2-benzenediamine 50 mg (0.2 mmol), ethanol 5 ml and benzyl 60 mg (0.3 mmol).

Melting point: 248–249° C.

Nuclear magnetic resonance spectrum (DMSO-$d_6$) δ: 9.50(1H,s), 9.23(1H,s), 8.86(1H,d), 8.62(1H,d), 8.60(1H,d), 8.37(1H,s), 8.23(1H,d), 8.02(1H,dd), 7.35–8.00(10H,m).

Infrared absorption spectrum $v_{max}$ (KBr) cm$^{-1}$: 1620, 1320, 1150, 1140, 700.

Element anlysis values (calculated as $C_{29}H_{18}ClN_3O_2S$)

|  | C(%) | H(%) | N(%) | S(%) |
| --- | --- | --- | --- | --- |
| Theoretical values | 68.57 | 3.57 | 8.27 | 6.31 |
| Found values | 68.73 | 3.74 | 8.29 | 6.69 |

EXAMPLE 118

9-(5-Isoquinolylsulfonyl)acenaphtho[1,2-b]quinoxaline

According to the method in Example 113, 9-(5-isoquinolylsulfonyl)acenaphtho[1,2-b]quinoxaline 250 mg (84.3%) was obtained from 4-(5-isoquinolylsulfonyl)-1,2-benzenediamine 200 mg (0.7 mmol), ethanol 20 ml and acenaphthene quinone 240 mg (1.3 mmol).

Melting point: >270° C.

Nuclear magnetic resonance spectrum (DMSO-$d_6$) δ: 9.48(1H,s), 8.88(1H,d), 8.85(1H,d), 8.76(1H,d), 8.57(1H,d), 8.52(1H,d), 8.43(2H,d), 8.33(2H,d), 8.32(1H,s), 8.25(1H,dd), 8.02(1H,dd), 7.91–7.97(2H,m).

Infrared absorption spectrum $v_{max}$ (KBr) cm$^{-1}$: 1620, 1420, 1320, 1125.

Element anlysis values (calculated as $C_{27}H_{15}N_3O_2S.1/2H_2O$)

|  | C(%) | H(%) | N(%) | S(%) |
| --- | --- | --- | --- | --- |
| Theoretical values | 71.35 | 3.55 | 9.25 | 7.06 |
| Found values | 71.58 | 3.83 | 9.62 | 7.45 |

EXAMPLE 119

9-Chloro-10-(5-isoquinolylsulfonyl)acenaphtho[1,2-b]quinoxaline

According to the method in Example 113, 9-chloro-10-(5-isoquinolylsulfonyl)acenaphtho[1,2-b]quinoxaline 30 mg (43.1%) was obtained from 4-(5-isoquinolylsulfonyl)-1,2-benzenediamine 50 mg (0.2 mmol), ethanol 5 ml and acenaphthene quinone 60 mg (0.3 mmol).

Melting point: >270° C.

Nuclear magnetic resonance spectrum (DMSO-$d_6$) δ: 9.50(1H,s), 9.25(1H,s), 8.89(1H,d), 8.63(1H,d), 8.61(1H,d), 8.52(1H,d), 8.46(1H,d), 8.40(1H,dd), 8.36(1H,s), 8.28(1H,d), 7.96–8.05(3H,m).

Infrared absorption spectrum $v_{max}$ (KBr) cm$^{-1}$: 1615, 1310, 1130.

Element anlysis values (calculated as $C_{27}H_{14}ClN_3O_2S$)

|  | C(%) | H(%) | N(%) | S(%) |
|---|---|---|---|---|
| Theoretical values | 67.57 | 2.94 | 8.76 | 6.68 |
| Found values | 67.91 | 3.20 | 8.92 | 7.01 |

EXAMPLE 120

11-(5-Isoquinolylsulfonyl)dibenzo[a,c]phenazine

According to the method in Example 113, 11-(5-isoquinolylsulfonyl)dibenzo[a,c]phenazine 260 mg (82.5%) was obtained from 4-(5-isoquinolylsulfonyl)-1,2-benzenediamine 200 mg (0.7 mmol), ethanol 20 ml and phenanthrenequinone 280 mg (1.3 mmol).

Melting point: >270° C.

Nuclear magnetic resonance spectrum (DMSO-$d_6$) δ: 9.46(1H,s), 9.22(1H,d), 9.19(1H,d), 8.95(1H,d), 8.85(1H,d), 8.68–8.69(3H,m), 8.56(1H,d), 8.54(1H,d), 8.42(1H,d), 8.30(1H,dd), 8.01(1H,dd), 7.76–7.87(4H,m).

Infrared absorption spectrum $v_{max}$ (KBr) cm$^{-1}$: 1620, 1610, 1320, 1155, 1140, 760.

Element anlysis values (calculated as $C_{29}H_{17}N_3O_2S$)

|  | C(%) | H(%) | N(%) | S(%) |
|---|---|---|---|---|
| Theoretical values | 73.87 | 3.63 | 8.91 | 6.80 |
| Found values | 73.66 | 3.68 | 8.92 | 6.47 |

EXAMPLE 121

5-(5-Isoquinolylsulfanyl)isoquinoline

To an aqueous 4N hydrochloric acid solution 24 ml of 5-aminoisoquinoline 1.00 g (6.9 mmol), a water solution 2 ml of sodium azide 480 mg (6.9 mmol) was added dropwise. The reaction mixture was stirred at 0° C. for 30 minutes and neutralized with sodium acetate, and insoluble materials were filtered. The filtrate was added to a sodium hydroxide solution (300 mg/3 ml) of 5-isoquinolinethiol 1.23 g (7.6 mmol), and the mixture was stirred for 1.5 hours at 80° C. After adding ethyl acetate, the reaction solution was washed with 1N sodium hydroxide and saturated sodium chloride, and dried over anhydrous magnesium sulfate. The organic layer was concentrated under reduced pressure, the resulting residue was purified by silica gel column chromatography (ethyl acetate), and 5-(5-isoquinolylsulfanyl)isoquinoline 230 mg (11.5%) was obtained.

Melting point: 138–140° C.

Mass spectrometry (m/z): 289 (M+1)

Nuclear magnetic resonance spectrum (DMSO-$d_6$) δ: 9.28(2H,s), 8.57(2H,d), 8.09(2H,dd), 7.91(2H,d), 7.44–7.49(4H,m).

Infrared absorption spectrum $v_{max}$ (KBr) cm$^{-1}$: 1610, 1570, 1480, 1360, 820, 750.

Element anlysis values (calculated as $C_{18}H_{12}N_2S$)

|  | C(%) | H(%) | N(%) | S(%) |
|---|---|---|---|---|
| Theoretical values | 74.97 | 4.19 | 9.71 | 11.12 |
| Found values | 74.74 | 4.17 | 9.82 | 10.93 |

EXAMPLE 122

5-(5-Isoquinolylsulfonyl)isoquinoline

According to the method in Example 2(b), 5-(5-isoquinolylsulfonyl)isoquinoline 60 mg (50.4%) was obtained from 5-(5-isoquinolylsulfanyl)isoquinoline 100 mg (0.4 mmol), concentrated sulfuric acid 1 ml and OXONE (trademark) 580 mg (0.9 mmol).

Melting point: 233–235° C.

Mass spectrometry (m/z): 321 (M+1)

Nuclear magnetic resonance spectrum (DMSO-$d_6$) δ: 9.27(2H,s), 8.78(2H,d), 8.56(2H,d), 8.28(2H,d), 8.22(2H,d), 7.80(2H,dd).

Infrared absorption spectrum $v_{max}$ (KBr) cm$^{-1}$: 1610, 1320, 1150, 1120, 980, 840, 710.

Element anlysis values (calculated as $C_{18}H_{12}N_2O_2S$)

|  | C(%) | H(%) | N(%) | S(%) |
|---|---|---|---|---|
| Theoretical values | 67.48 | 3.78 | 8.74 | 10.01 |
| Found values | 67.20 | 3.65 | 8.62 | 9.74 |

EXAMPLE 123

2-Cyclohexyl-5(6)-(5-isoquinolylsulfonyl)-6(5)-nitro-1H-benzo[d]imidazole and 2-cyclohexyl-5(6)-(5-isoquinolylsulfonyl)-7(4)-nitro-1H-benzo[d]imidazole According to the method in Example 52(b), 2-cyclohexyl-5(6)-(5-isoquinolylsulfonyl)-6(5)-nitro-1H-benzo[d]imidazole 5.90 g (65.2%) and 2-cyclohexyl-5(6)-(5-isoquinolylsulfonyl)-7(4)-nitro-1H-benzo[d]imidazole 600 mg (6.6%) were obtained from 2-cyclohexyl-5(6)-(5-isoquinolylsulfonyl)-1H-benzo[d]imidazole 7.83 g (20 mmol), fuming nitric acid 0.5 ml and concentrated sulfuric acid 5 ml.

2-Cyclohexyl-5(6)-(5-isoquinolylsulfonyl)-6(5)-nitro-1H-benzo[d]imidazole

Melting point: >270° C.

Mass spectrometry (m/z): 437 (M+1)

Nuclear magnetic resonance spectrum (DMSO-$d_6$) δ: 9.51(1H,s), 8.66(1H,d), 8.53(1H,s), 8.52(1H,d), 8.42(1H,d), 8.32(1H,d), 8.26(1H,s), 7.91(1H,dd), 2.95–2.99(1H,m), 2.03(2H,d), 1.77(2H,d), 1.57–1.69(3H,m), 1.17–1.42(3H, m).

Infrared absorption spectrum $v_{max}$ (KBr) cm$^{-1}$: 3320, 2930, 2850, 1540, 1350, 1290, 1130.

Element anlysis values (calculated as $C_{22}H_{20}N_4O_4S.1/2H_2O$)

|                    | C(%)  | H(%) | N(%)  | S(%) |
|--------------------|-------|------|-------|------|
| Theoretical values | 59.31 | 4.75 | 12.58 | 7.20 |
| Found values       | 59.34 | 5.01 | 12.21 | 7.10 |

2-Cyclohexyl-5(6)-(5-isoquinolylsulfonyl)-7(4)-nitro-1H-benzo[d]imidazole

Melting point: 236–237° C.

Mass spectrometry (m/z): 437 (M+1)

Nuclear magnetic resonance spectrum (DMSO-$d_6$) δ: 9.45(1H,s), 8.77(1H,d), 8.67(1H,d), 8.63(1H,s), 8.52(1H,d), 8.48(1H,s), 8.44(1H,d), 7.94(1H,dd), 2.99–3.05(1H,m), 1.94–1.97(1H,m), 1.56–1.77(5H,m), 1.23–1.38(4H,m).

Infrared absorption spectrum $v_{max}$ (KBr) cm$^{-1}$: 2930, 2920, 1630, 1620, 1510, 1130, 620.

Element anlysis values (calculated as $C_{22}H_{20}N_4O_4S$)

|                    | C(%)  | H(%) | N(%)  | S(%) |
|--------------------|-------|------|-------|------|
| Theoretical values | 60.54 | 4.62 | 12.84 | 7.35 |
| Found values       | 60.91 | 4.87 | 12.53 | 7.30 |

EXAMPLE 124

2-Cyclopentyl-5(6)-(5-isoquinolylsulfonyl)-6(5)-nitro-1H-benzo[d]imidazole and 2-cyclopentyl-5(6)-(5-isoquinolylsulfonyl)-7(4)-nitro-1H-benzo[d]imidazole According to the method in Example 52(b), 2-cyclopentyl-5(6)-(5-isoquinolylsulfonyl)-6(5)-nitro-1H-benzo[d]imidazole 6.73 g (74.4%) and 2-cyclopentyl-5(6)-(5-isoquinolylsulfonyl)-7(4)-nitro-1H-benzo[d]imidazole 840 mg (9.3%) were obtained from 2-cyclopentyl-5(6)-(5-isoquinolylsulfonyl)-1H-benzo[d]imidazole 8.10 g (21.4 mmol), fuming nitric acid 8.0 ml and concentrated sulfuric acid 80 ml.

2-Cyclopentyl-5(6)-(5-isoquinolylsulfonyl)-6-(5)-nitro-1H-benzo[d]imidazole

Melting point: 263–264° C.

Mass spectrometry (m/z): 423 (M+1)

Nuclear magnetic resonance spectrum (DMSO-$d_6$) δ: 9.50(1H,s), 8.66(1H,d), 8.54(1H,d), 8.53(1H,s), 8.43(1H,d), 8.31(1H,d), 8.25(1H,s), 7.92(1H,dd), 3.37–3.44(1H,m), 2.07–2.13(2H,m), 1.87–1.98(2H,m), 1.65–1.79(4H,m).

Infrared absorption spectrum $v_{max}$ (KBr) cm$^{-1}$: 3320, 1540, 1360, 1300.

Element anlysis values (calculated as $C_{21}H_{18}N_4O_4S$)

|                    | C(%)  | H(%) | N(%)  | S(%) |
|--------------------|-------|------|-------|------|
| Theoretical values | 59.70 | 4.29 | 13.26 | 7.59 |
| Found values       | 59.36 | 4.48 | 13.48 | 7.23 |

2-Cyclopentyl-5(6)-(5-isoquinolylsulfonyl)-7(4)-nitro-1H-benzo[d]imidazole

Melting point: 252–254° C.

Mass spectrometry (m/z): 423 (M+1)

Nuclear magnetic resonance spectrum (DMSO-$d_6$) δ: 9.45(1H,s), 8.77(1H,dd), 8.66(1H,d), 8.62(1H,s), 8.51(1H,d), 8.49(1H,d), 8.44(1H,d), 7.94(1H,dd), 3.44(1H,tt), 1.61–2.05(8H,m).

Infrared absorption spectrum $v_{max}$ (KBr) cm$^{-1}$: 1510, 1130, 620.

Element anlysis values (calculated as $C_{21}H_{18}N_4O_4S$)

|                    | C(%)  | H(%) | N(%)  | S(%) |
|--------------------|-------|------|-------|------|
| Theoretical values | 59.70 | 4.29 | 13.26 | 7.59 |
| Found values       | 59.79 | 4.46 | 13.16 | 7.62 |

EXAMPLE 125

6(5)-Chloro-2-cyclohexyl-5(6)-(5-isoquinolylsulfonyl)-1H-benzo[d]imidazole

According to the method in Example 91, 6(5)-chloro-2-cyclohexyl-5(6)-(5-isoquinolylsulfonyl)-1H-benzo[d]imidazole 200 mg (31.3%) was obtained from 4-chloro-5-(5-isoquinolylsulfonyl)-1,2-benzenediamine 500 mg (1.5 mmol), cyclohexanecarboxylic acid 510 mg (4.0 mmol) and 6N hydrochloric acid 10 ml.

Mass spectrometry (m/z): 426 (M+1)

Nuclear magnetic resonance spectrum (DMSO-$d_6$) δ: 9.46(1H,d), 8.72(1H,dd), 8.64(1H,s), 8.57(1H,d), 8.54(1H,d), 8.13(1H,d), 7.95(1H,dd), 7.63(1H,brs), 2.90–2.94(1H,m), 2.03(2H,d), 1.56–1.81(5H,m), 1.35–1.43(2H,m), 1.24–1.30(1H,m).

Infrared absorption spectrum $v_{max}$ (KBr) cm$^{-1}$: 2930, 2850, 1620, 1460, 1320, 1130.

Element anlysis values (calculated as $C_{22}H_{20}ClN_3O_2S \cdot 1/4H_2O$)

|                    | C(%)  | H(%) | N(%) |
|--------------------|-------|------|------|
| Theoretical values | 61.39 | 4.80 | 9.76 |
| Found values       | 61.32 | 4.67 | 9.69 |

EXAMPLE 126

6(5)-Chloro-2-cyclopentyl-5(6)-(5-isoquinolylsulfonyl)-1H-benzo[d]imidazole

According to the method in Example 91, 6(5)-chloro-2-cyclopentyl-5(6)-(5-isoquinolylsulfonyl)-1H-benzo[d]imidazole 430 mg (69.3%) was obtained from 4-chloro-5-(5-isoquinolylsulfonyl)-1,2-benzenediamine 500 mg (1.5 mmol), cyclopentylcarboxylic acid 500 mg (4.4 mmol) and 6N hydrochloric acid 10 ml.

Melting point: 212–214° C.

Mass spectrometry (m/z): 412 (M+1)

Nuclear magnetic resonance spectrum (DMSO-$d_6$) δ: 9.46(1H,d), 8.72(1H,dd), 8.64(1H,s), 8.57(1H,d), 8.53(1H, d), 8.13(1H,d), 7.95(1H,dd), 7.62(1H,s), 3.31–3.36(1H,m), 2.07–2.10(2H,m), 1.87–1.91(2H,m), 1.64–1.77(4H,m).

Infrared absorption spectrum $v_{max}$ (KBr) cm$^{-1}$: 3330, 1620, 1530, 1460, 1300, 1160.

Element anlysis values (calculated as $C_{21}H_{18}ClN_3O_2S$)

|                    | C(%)  | H(%) | S(%)  |
|--------------------|-------|------|-------|
| Theoretical values | 61.24 | 4.40 | 10.20 |
| Found values       | 61.47 | 4.75 | 10.44 |

EXAMPLE 127

6(5)-Chloro-2-cyclobutyl-5(6)-(5-isoquinolylsulfonyl)-1H-benzo[d]imidazole

According to the method in Example 91, 6(5)-chloro-2-cyclobutyl-5(6)-(5-isoquinolylsulfonyl)-1H-benzo[d]

imidazole 380 mg (64.0%) was obtained from 4-chloro-5-(5-isoquinolylsulfonyl)-1,2-benzenediamine 500 mg (1.5 mmol), cyclobutylcarboxylic acid 510 mg (5.1 mmol) and 6N hydrochloric acid 10 ml.

Melting point: 164° C.

Mass spectrometry (m/z): 398 (M+1)

Nuclear magnetic resonance spectrum (DMSO-$d_6$) δ: 9.46(1H,s), 8.72(1H,dd), 8.65(1H,s), 8.56(1H,d), 8.54(1H,d), 8.12(1H,d), 7.95(1H,dd), 7.63(1H,s), 3.77–3.80(1H,m), 2.35–2.37(4H,m), 2.04–2.08(1H,m), 1.91–1.94(1H,m).

Infrared absorption spectrum $v_{max}$ (KBr) cm$^{-1}$: 1620, 1460, 1320, 1140.

Element anlysis values (calculated as $C_{20}H_{16}N_3O_2S.3/4H_2O$)

| | C(%) | H(%) | N(%) | S(%) |
|---|---|---|---|---|
| Theoretical values | 58.34 | 4.29 | 10.21 | 7.79 |
| Found values | 58.29 | 4.14 | 9.81 | 7.66 |

EXAMPLE 128

5-(5-Isoquinolylsulfanyl)-2-nitro-4-(trifluoromethyl)aniline

According to the method in Example 10, 5-(5-isoquinolylsulfanyl)-2-nitro-4-(trifluoromethyl)aniline 2.04 g (79.4%) was obtained from 5-isoquinolinethiol 1.20 g (7.4 mmol), DMF 40 ml, potassium carbonate 2.00 g (14.5 mmol) and 5-chloro-2-nitro-4-(trifluoromethyl)aniline 1.70 g (7.1 mmol).

Melting point: 263–265° C.

Mass spectrometry (m/z): 366 (M+1)

Nuclear magnetic resonance spectrum (DMSO-$d_6$) δ: 9.48(1H,s), 8.60(1H,d), 8.42(1H,d), 8.27(1H,s), 8.22(1H,d), 7.85(1H,dd), 7.82(1H,d), 7.64(1H,s), 6.15(1H,s).

Infrared absorption spectrum $v_{max}$ (KBr) cm$^{-1}$: 3450, 1630, 1330, 1300, 1260.

Element analysis values (calculated as $C_{16}H_{10}F_3N_3O_2S$)

| | C(%) | H(%) | N(%) | S(%) |
|---|---|---|---|---|
| Theoretical values | 52.60 | 2.76 | 11.50 | 8.78 |
| Found values | 52.22 | 2.87 | 11.16 | 8.92 |

EXAMPLE 129

5-(5-Isoquinolylsulfonyl)-2-nitro-4-(trifluoromethyl)aniline

According to the method in Example 7(b), 5-(5-isoquinolylsulfonyl)-2-nitro-4-(trifluoromethyl)aniline sulfate 130 mg (46.1%) was obtained from 5-(5-isoquinolylsulfonyl)-2-nitro-4-(trifluoromethyl)aniline 200 mg (0.5 mmol), concentrated sulfuric acid 2 ml and OXONE (trademark) 680 mg (1.1 mmol). Melting point: >270° C.

Mass spectrometry (m/z): 398 (M+1)

Nuclear magnetic resonance spectrum (DMSO-$d_6$) δ: 9.78(1H,s), 8.76(1H,d), 8.75(1H,d), 8.63(1H,d), 8.37(1H,s), 8.32(1H,d), 8.08(1H,dd), 7.99(1H,s).

Infrared absorption spectrum $v_{max}$ (KBr) cm$^{-1}$: 3450, 1640, 1350, 1280, 1150, 1120.

Element analysis values (calculated as $C_{16}H_{10}F_3N_3O_4S.H_2SO_4$)

| | C (%) | H (%) | N (%) | S (%) |
|---|---|---|---|---|
| Theoretical values | 38.79 | 2.44 | 8.48 | 12.95 |
| Found values | 38.92 | 2.24 | 8.17 | 12.94 |

EXAMPLE 130

4-(5-Isoquinolylsulfonyl)-5-(trifluoromethyl)-1,2-benzenediamine

According to the method in Example 3, 4-(5-isoquinolylsulfonyl)-5-(trifluoromethyl)-1,2-benzenediamine was obtained from 5-(5-isoquinolylsulfonyl)-2-nitro-4-(trifluoromethyl)aniline sulfate 200 mg (0.4 mmol), concentrated hydrochloric acid 4 ml and stannous chloride dihydrate 350 mg (1.6 mmol). The resulting compound was changed to a hydrochloride and crystallized from methanol-ether, and 4-(5-isoquinolylsulfonyl)-5-(trifluoromethyl)-1,2-benzenediamine hydrochloride 160 mg (85.2%) was obtained.

Melting point: 215° C.

Mass spectrometry (m/z): 368 (M+1)

Nuclear magnetic resonance spectrum (DMSO-$d_6$) δ: 9.92(1H,d), 8.78(1H,d), 8.74(1H,d), 8.67(1H,d), 8.43(1H,d), 8.06(1H,dd), 7.73(1H,s), 7.09(1H,s).

Infrared absorption spectrum $v_{max}$ (KBr) cm$^{-1}$: 3350, 3200, 1620, 1140.

Element analysis values (calculated as $C_{16}H_{12}F_3N_3O_2S.2HCl$)

| | C (%) | H (%) | N (%) | S (%) |
|---|---|---|---|---|
| Theoretical values | 43.65 | 3.21 | 9.54 | 7.28 |
| Found values | 43.81 | 3.60 | 9.20 | 7.07 |

EXAMPLE 131

5(6)-(5-Isoquinolylsulfonyl)-2-methyl-6(5)-(trifluoromethyl)-1H-benzo[d]imidazole According to the method in Example 91, 5(6)-(5-isoquinolylsulfonyl)-2-methyl-6(5)-(trifluoromethyl)-1H-benzo[d]imidazole 80 mg (97.4%) was obtained from 4-(5-isoquinolylsulfonyl)-5-(trifluoromethyl)-1,2-benzenediamine 100 mg (0.2 mmol), acetic acid 0.1 ml and 6N hydrochloric acid 1.5 ml.

Melting point: 231–236° C.

Mass spectrometry (m/z): 392 (M+1)

Nuclear magnetic resonance spectrum (DMSO-$d_6$) δ: 9.48(1H,s), 8.59(1H,d), 8.52(1H,d), 8.48(1H,s), 8.34(1H,d), 8.17(1H,d), 8.09(1H,s), 7.88(1H,dd), 2.60(3H,s).

Infrared absorption spectrum $v_{max}$ (KBr) cm$^{-1}$: 1620, 1320, 1160, 1140.

Element analysis values (calculated as $C_{18}H_{12}F_3N_3O_2S$)

| | C (%) | H (%) | N (%) | S (%) |
|---|---|---|---|---|
| Theoretical values | 55.24 | 3.09 | 10.74 | 8.19 |
| Found values | 55.45 | 3.43 | 10.61 | 8.02 |

EXAMPLE 132

4-Bromo-5-(5-isoquinolylsulfanyl)-2-nitroaniline

According to the method in Example 10, 4-bromo-5-(5-isoquinolylsulfanyl)-2-nitroaniline 1.14 g (75.8%) was obtained as powder from 5-isoquinolinethiol 670 mg (4.2 mmol), DMF 15 ml, potassium carbonate 1.10 g (8.0 mmol) and 4-bromo-5-chloro-2-nitroaniline 1.00 g (4.0 mmol).

Melting point: >270° C.

Mass spectrometry (m/z): 377 (M+1)

Nuclear magnetic resonance spectrum (DMSO-$d_6$) δ: 9.47(1H,s), 8.59(1H,d), 8.42(1H,d), 8.21(1H,d), 8.14(1H,s), 7.82–7.85(2H,m), 7.26(2H,s), 5.92(1H,s).

Infrared absorption spectrum $v_{max}$ (KBr) cm$^{-1}$: 3450, 1610, 1480, 1460, 1260, 1240.

Element analysis values (calculated as $C_{15}H_{10}BrN_3O_2S$)

|  | C (%) | H (%) | N (%) | S (%) |
| --- | --- | --- | --- | --- |
| Theoretical values | 47.89 | 2.68 | 11.17 | 8.52 |
| Found values | 48.28 | 2.56 | 11.14 | 8.33 |

EXAMPLE 133

4-Bromo-5-(5-isoquinolylsulfonyl)-1,2-benzenediamine

According to the method in Example 3, 4-bromo-5-(5-isoquinolylsulfonyl)-1,2-benzenediamine 920 mg (21.5%) was obtained from 4-bromo-5-(5-isoquinolylsulfonyl)-2-nitroaniline 4.62 g (11.3 mmol), concentrated hydrochloric acid 140 ml and stannous chloride dihydrate 12.80 g (56.6 mmol).

Melting point: 219–220° C.

Mass spectrometry (m/z): 379 (M+1)

Nuclear magnetic resonance spectrum (DMSO-$d_6$) δ: 9.32(1H,s), 8.56(1H,d), 7.96(1H,d), 7.94(1H,d), 7.57(1H,dd), 7.20(1H,d), 6.87(1H,s), 6.69(1H,s), 5.15(2H,s), 4.78(2H,s).

Infrared absorption spectrum $v_{max}$ (KBr) cm$^{-1}$: 1620, 1560, 1490, 1310, 1130.

Element analysis values (calculated as $C_{15}H_{12}BrN_3O_2S$)

|  | C (%) | H (%) | N (%) | S (%) |
| --- | --- | --- | --- | --- |
| Theoretical values | 47.63 | 3.20 | 11.11 | 8.48 |
| Found values | 47.89 | 2.91 | 10.83 | 8.34 |

EXAMPLE 134

6(5)-Bromo-5(6)-(5-isoquinolylsulfonyl)-2-methyl-1H-benzo[d]imidazole

According to the method in Example 91, 6(5)-bromo-5(6)-(5-isoquinolylsulfonyl)-2-methyl-1H-benzo[d]imidazole 160 mg (75.2%) was obtained from 4-bromo-5-(5-isoquinolylsulfonyl)-1,2-benzenediamine 200 mg (0.5 mmol), acetic acid 0.2 ml and 6N hydrochloric acid 8.0 ml.

Melting point: 183–185° C.

Mass spectrometry (m/z): 403 (M+1)

Nuclear magnetic resonance spectrum (DMSO-$d_6$) δ: 9.43(1H,s), 8.67(1H,s), 8.66(1H,d), 8.54(1H,d), 8.49(1H,d), 8.16(1H,d), 7.91(1H,dd), 7.18(1H,s), 2.57(3H,s).

Infrared absorption spectrum $v_{max}$ (KBr) cm$^{-1}$: 1620, 1380, 1300, 1130.

Element analysis values (calculated as $C_{17}H_{12}BrN_3O_2S$)

|  | C (%) | H (%) | N (%) | S (%) |
| --- | --- | --- | --- | --- |
| Theoretical values | 50.76 | 3.01 | 10.45 | 7.97 |
| Found values | 50.75 | 3.06 | 10.53 | 8.34 |

EXAMPLE 135

6(5)-Bromo-2-ethyl-5(6)-(5-isoquinolylsulfonyl)-1H-benzo[d]imidazole

According to the method in Example 91, 6(5)-bromo-2-ethyl-5(6)-(5-isoquinolylsulfonyl)-1H-benzo[d]imidazole 140 mg (65.4%) was obtained from 4-bromo-5-(5-isoquinolylsulfonyl)-1,2-benzenediamine 200 mg (0.5 mmol), propionic acid 0.2 ml and 6N hydrochloric acid 8.0 ml.

Mass spectrometry (m/z): 417 (M+1)

Nuclear magnetic resonance spectrum (DMSO-$d_6$) δ: 9.46(1H,s), 8.72(1H,d), 8.70(1H,s), 8.55(1H,dd), 8.52(1H,d), 8.10(1H,d), 7.94(1H,dd), 7.81(1H,s), 2.91(2H,q), 1.33(3H,t).

Infrared absorption spectrum $v_{max}$ (KBr) cm$^{-1}$: 1620, 1450, 1310, 1130.

Element analysis values (calculated as $C_{18}H_{14}BrN_3O_2S$)

|  | C (%) | H (%) | N (%) |
| --- | --- | --- | --- |
| Theoretical values | 51.93 | 3.39 | 10.09 |
| Found values | 52.12 | 3.21 | 10.38 |

EXAMPLE 136

6(5)-Bromo-2-cyclohexyl-5(6)-(5-isoquinolylsulfonyl)-1H-benzo[d]imidazole

According to the method in Example 91, 6(5)-bromo-2-cyclohexyl-5(6)-(5-isoquinolylsulfonyl)-1H-benzo[d]imidazole 140 mg (65.4%) was obtained from 4-bromo-5-(5-isoquinolylsulfonyl)-1,2-benzenediamine 200 mg (0.5 mmol), cyclohexyl carboxylic acid 340 mg and 6N hydrochloric acid 8.0 ml.

Melting point: 249–250° C.

Mass spectrometry (m/z): 471 (M+1)

Nuclear magnetic resonance spectrum (DMSO-$d_6$) δ: 9.46(1H,s), 8.72(1H,dd), 8.69(1H,s), 8.56(1H,d), 8.53(1H,d), 8.13(1H,d), 7.94(1H,dd), 7.81(1H,s), 2.89–2.95(1H,m), 2.03(2H,d), 1.56–1.63(2H,m), 1.22–1.40(3H,m).

Infrared absorption spectrum $v_{max}$ (KBr) cm$^{-1}$: 3350, 2930, 2850, 1520, 1460, 1300, 1130.

Element analysis values (calculated as $C_{22}H_{20}BrN_3O_2S \cdot 1/4H_2O$)

|  | C (%) | H (%) | N (%) | S (%) |
| --- | --- | --- | --- | --- |
| Theoretical values | 55.64 | 4.35 | 8.85 | 6.76 |
| Found values | 55.65 | 4.24 | 8.60 | 6.96 |

EXAMPLE 137

Diethyl{[5(6)-(5-isoquinolylsulfonyl)-1H-benzo[d]imidazole-2-yl]ethyl}amine

According to the method in Example 91, diethyl{[5(6)-(5isoquinolylsulfonyl)-1H-benzo[d]imidazole-2-yl]

ethyl}amine hydrochloride 230 mg (44.9%) was obtained from 5-(5-isoquinolylsulfonyl)-1,2-benzenediamine 300 mg (1.0 mmol), N,N-diethyl-β-alanine hydrochloride 550 mg (3.0 mmol) and 6N hydrochloric acid 4.0 ml.

Mass spectrometry (m/z): 409 (M+1)

Nuclear magnetic resonance spectrum (DMSO-$d_6$) δ: 9.86(1H,s), 8.94(1H,d), 8.73–8.77(3H,m), 8.41(1H,s), 8.14 (1H,dd), 7.99(1H,d), 7.87(1H,d), 3.63–3.65(4H,m), 3.18 (4H,q), 1.26(6H,t).

Infrared absorption spectrum $v_{max}$ (KBr) cm$^{-1}$: 1650, 1630, 1320, 1140.

Element analysis values (calculated as $C_{22}H_{24}N_4O_2S \cdot 5/2HCl$)

|  | C (%) | H (%) | N (%) |
|---|---|---|---|
| Theoretical values | 52.88 | 5.35 | 11.21 |
| Found values | 52.76 | 5.66 | 10.84 |

EXAMPLE 138

Diethyl{[5(6)-(5-isoquinolylsulfonyl)-6(5)-nitro-1H-benzo[d]imidazole-2-yl]ethyl}amine According to the method in Example 52(b), diethyl{[5 (6)-(5-isoquinolylsulfonyl)-6(5)-nitro-1H-benzo[d] imidazol-2-yl]ethyl}amine 40 mg (39.2%) was obtained from diethyl{[5(6)-(5-isoquinolylsulfonyl)-6(5)-nitro-1H-benzo[d]imidazol-2-yl]ethyl}amine 100 mg (0.2 mmol), fuming nitric acid 0.1 ml and concentrated sulfuric acid 1 ml.

Melting point: 147–156° C.

Mass spectrometry (m/z): 454 (M+1)

Nuclear magnetic resonance spectrum (DMSO-$d_6$) δ: 9.44(1H,s), 8.59(1H,d), 8.51(1H,s), 8.48(1H,d), 8.37(1H,d), 8.26(1H,d), 8.21(1H,s), 7.86(1H,dd), 2.99(2H,t), 2.87(2H,t), 2.50(4H,q), 0.90(6H,t).

Infrared absorption spectrum $v_{max}$ (KBr) cm$^{-1}$: 2980, 1620, 1540, 1320, 1130.

Element analysis values (calculated as $C_{22}H_{23}N_5O_4S$)

|  | C (%) | H (%) | N (%) |
|---|---|---|---|
| Theoretical values | 58.26 | 5.11 | 15.44 |
| Found values | 57.93 | 4.89 | 15.64 |

EXAMPLE 139

6(5)-Chloro-5(6)-(5-isoquinolylsulfonyl)-1H-benzo [d]imidazol-2-carbamic acid methyl ester To a mixture of 4-chloro-5-(5-isoquinolylsulfonyl)-1,2-benzenediamine 100 mg (0.3 mmol), 2-methylthiopseudourea-1,3-dicarboxylic dimethylester 60 mg (0.3 mmol) and ethanol 10 ml, concentrated hydrochloric acid 2 drops were added, and the mixture was heated and refluxed 8 hours. The reaction mixture was cooled to room temperature, the precipitates were collected. The resulting precipitates were washed with saturated sodium bicarbonate, ethanol and ether, and 6(5)-chloro-5(6)-(5-isoquinolylsulfonyl)-1H-benzo[d]imidazole-2-carbamic acid methyl ester 50 mg (41.6%) was obtained.

Melting point: 260° C.

Mass spectrometry (m/z): 417 (M+1)

Nuclear magnetic resonance spectrum (DMSO-$d_6$) δ: 9.57(1H,s), 8.75(1H,d), 8.58–8.66(3H,m), 8.19(1H,d), 8.00 (1H,dd), 7.52(1H,d), 3.79(3H,s).

Infrared absorption spectrum $v_{max}$ (KBr) cm$^{-1}$: 3420, 1720, 1650, 1310, 1240.

Element analysis values (calculated as $C_{18}H_{13}ClN_4O_4S \cdot H_2O$)

|  | C (%) | H (%) | N (%) | S (%) |
|---|---|---|---|---|
| Theoretical values | 49.72 | 3.48 | 12.88 | 7.37 |
| Found values | 50.06 | 3.35 | 12.89 | 7.57 |

EXAMPLE 140

2-Amino-4-(5-isoquinolylsulfanyl)-1-(4-methylphenyl)sulfonamide-5-nitrobenzene

To a solution 5 ml of 4-(5-isoquinolylsulfanyl)-5-nitro-1, 2-benzenediamine 100 mg (0.3 mmol) in pyridine 5 ml, p-toluenesulfonyl chloride 70 mg (0.4 mmol) was added, and the mixture was stirred for 1 hour at room temperature. The reaction mixture was concentrated under reduced pressure, 4N sodium hydroxide was added, and the solution was extracted with ethyl acetate. The organic layer was washed with saturated sodium chloride, dried over magnesium sulfate, concentrated under reduced pressure, and 2-amino-4-(5-isoquinolylsulfanyl)-1-(4-methylphenyl) sulfonamide-5-nitrobenzene 110 mg (70.3%) was obtained.

Melting point: >270° C.

Mass spectrometry (m/z): 467 (M+1)

Nuclear magnetic resonance spectrum (DMSO-$d_6$) δ: 9.44(1H,s), 9.39(1H,brs), 8.55(1H,d), 8.37(1H,d), 8.19(1H, d), 7.81–7.82(2H,m), 7.79(1H,s), 7.57(2H,d), 7.35(2H,d), 6.23(2H,brs), 5.55(1H,s), 2.34(3H,s).

Infrared absorption spectrum $v_{max}$ (KBr) cm$^{-1}$: 3400, 1620, 1500, 1280, 1160.

Element analysis values (calculated as $C_{22}H_{18}N_4O_4S_2 \cdot 1/4H_2O$)

|  | C (%) | H (%) | N (%) | S (%) |
|---|---|---|---|---|
| Theoretical values | 56.10 | 3.96 | 11.89 | 13.61 |
| Found values | 56.33 | 4.16 | 11.58 | 13.40 |

EXAMPLE 141

3-Fluoro-4-(5-isoquinolylsulfonyl)benzonitrile

According to the method in Example 7(b), 3-fluoro-4-(5-isoquinolylsulfonyl)benzonitrile 160 mg (63.8%) was obtained from 3-fluoro-4-(5-isoquinolylsulfanyl) benzonitrile 200 mg (0.7 mmol), concentrated sulfuric acid 2 ml, water 4 ml and OXONE (trademark) 1.10 g (1.8 mmol).

Melting point: 182–187° C.

Mass spectrometry (m/z): 313 (M+1)

Nuclear magnetic resonance spectrum (DMSO-$d_6$) δ: 9.50(1H,d), 8.73(1H,d), 8.63(1H,d), 8.62(1H,d), 8.52(1H, dd), 8.16(1H,d), 7.89–8.04(3H,m).

Infrared absorption spectrum $v_{max}$ (KBr) cm$^{-1}$: 3450, 1605, 1480, 1420, 1320, 1160, 1140.

Element analysis values (calculated as $C_{16}H_9N_2O_2S \cdot 1/4H_2SO_4 \cdot 1/2H_2O$)

|                   | C (%) | H (%) | N (%) | S (%) |
|-------------------|-------|-------|-------|-------|
| Theoretical values | 54.16 | 3.27  | 7.89  | 11.30 |
| Found values       | 54.25 | 2.87  | 7.52  | 11.57 |

EXAMPLE 142

3-Chloro-4-(5-isoquinolylsulfonyl)benzonitrile

According to the method in Example 7(b), 3-chloro-4-(5-isoquinolylsulfonyl)benzonitrile 170 mg (66.0%) was obtained from 3-chloro-4-(5-isoquinolylsulfanyl)benzonitrile 200 mg (0.7 mmol), concentrated sulfuric acid 2 ml, water 4 ml and OXONE (trademark) 1.00 g (1.6 mmol).

Melting point: 214–217° C.

Mass spectrometry (m/z): 329 (M+1)

Nuclear magnetic resonance spectrum (DMSO-$d_6$) δ: 9.69(1H,s), 8.88(1H,d), 8.73(1H,d), 8.71(1H,d), 8.65(1H,d), 8.21–8.24(3H,m), 8.01(1H,dd).

Infrared absorption spectrum $v_{max}$ (KBr) cm$^{-1}$: 2240, 1620, 1380, 1340.

Element analysis values (calculated as $C_{16}H_9ClN_2O_2S \cdot 1/2H_2SO_4 \cdot 1/2H_2O$)

|                    | C (%) | H (%) | N (%) | S (%) |
|--------------------|-------|-------|-------|-------|
| Theoretical values | 49.68 | 2.87  | 7.24  | 12.43 |
| Found values       | 49.78 | 2.64  | 7.08  | 12.16 |

EXAMPLE 143

4-(5-Isoquinolylsulfonyl)-3-nitrobenzamide

According to the method in Example 7(b), 4-(5-isoquinolylsulfonyl)-3-nitrobenzamide 180 mg (85.9%) was obtained from 4-(5-isoquinolylsulfanyl)-3-nitrobenzonitrile 200 mg (0.7 mmol), concentrated sulfuric acid 2 ml and OXONE (trademark) 600 mg (1.0 mmol).

Melting point: 259–261° C.

Mass spectrometry (m/z): 358 (M+1)

Nuclear magnetic resonance spectrum (DMSO-$d_6$) δ: 9.52(1H,s), 8.67(1H,d), 8.61(1H,d), 8.56(1H,d), 8.54(1H,dd), 8.43(1H,d), 8.38(1H,s), 8.34(1H,dd), 8.21(1H,d), 7.99(1H,dd), 7.90(1H,s).

Infrared absorption spectrum $v_{max}$ (KBr) cm$^{-1}$: 3450, 1680, 1540, 1320.

Element analysis values (calculated as $C_{16}H_{11}N_3O_5S$)

|                    | C (%) | H (%) | N (%)  | S (%) |
|--------------------|-------|-------|--------|-------|
| Theoretical values | 53.77 | 3.10  | 11.76  | 8.97  |
| Found values       | 54.09 | 3.44  | 11.46  | 8.85  |

EXAMPLE 144

5-(5-Chloro-2-nitrophenylsulfanyl)isoquinoline

According to the method in Example 10, a mixture of 5-isoquinolinethiol 500 mg (3.1 mmol), DMF 10 ml, potassium carbonate 700 mg (5.1 mmol) and 4-chloro-2-fluoronitrobenzene 800 mg (5.0 mmol) was stirred at room temperature for 2 hours, and 5-(5-chloro-2-nitrophenylsulfanyl)isoquinoline 910 mg (92.7%) was obtained.

Melting point: 151–153° C.

Mass spectrometry (m/z): 317 (M+1)

Nuclear magnetic resonance spectrum (DMSO-$d_6$) δ: 9.49(1H,s), 8.57(1H,d), 8.44(1H,d), 8.34(1H,d), 8.30(1H,dd), 7.92(1H,d), 7.88(1H,dd), 7.44(1H,dd), 6.33(1H,d).

Infrared absorption spectrum $v_{max}$ (KBr) cm$^{-1}$: 1580, 1560, 1510, 1330, 860, 820.

Element analysis values (calculated as $C_{15}H_9ClN_2O_2S$)

|                    | C (%) | H (%) | N (%) | S (%) |
|--------------------|-------|-------|-------|-------|
| Theoretical values | 56.88 | 2.86  | 8.84  | 10.12 |
| Found values       | 56.85 | 2.87  | 8.85  | 10.11 |

EXAMPLE 145

5-[5-(1H-1-imidazolyl)-2-nitrophenylsulfanyl]isoquinoline

According to the method in Example 10, a mixture of 5-(5-chloro-2-nitrophenylsulfanyl)isoquinoline 630 mg (2.0 mmol), DMF 5 ml, potassium carbonate 300 mg (2.2 mmol) and imidazole 140 mg (2.1 mmol) was stirred at 140° C. for 3 hours, and 5-[5-(1H-1-imidazolyl)-2-nitrophenylsulfanyl]isoquinoline 340 mg (49.0%) was obtained.

Melting point: 178–188° C.

Mass spectrometry (m/z): 349 (M+1)

Nuclear magnetic resonance spectrum (DMSO-$d_6$) δ: 9.45(1H,d), 8.52(1H,d), 8.43(1H,d), 8.40(1H,d), 8.29(1H,dd), 7.92(1H,d), 7.85(1H,dd), 7.77(1H,dd), 7.65(1H,dd), 7.10(1H,dd), 6.95(1H,dd), 6.52(1H,d).

Infrared absorption spectrum $v_{max}$ (KBr) cm$^{-1}$: 1580, 1500, 1330, 1300.

EXAMPLE 146

5-(5-Chloro-2-nitrophenylsulfonyl)isoquinoline

According to the method in Example 7(b), 5-(5-chloro-2-nitrophenylsulfonyl)isoquinoline 160 mg (62.3%) was obtained from 5-(5-chloro-2-nitrophenylsulfanyl)isoquinoline 230 mg (0.7 mmol), concentrated sulfuric acid 2 ml and OXONE (trademark) 900 mg (1.5 mmol).

Melting point: 162–168° C.

Mass spectrometry (m/z): 349 (M+1)

Nuclear magnetic resonance spectrum (DMSO-$d_6$) δ: 9.54(1H,s), 8.70(1H,d), 8.61(1H,d), 8.52(1H,dd), 8.51(1H,s), 8.26(1H,d), 8.10–8.15(2H,m), 7.97(1H,dd).

Infrared absorption spectrum $v_{max}$ (KBr) cm$^{-1}$: 3100, 1540, 1370, 1330, 1160, 600.

Element analysis values (calculated as $C_{15}H_9ClN_2O_4S$)

|                    | C (%) | H (%) | N (%) | S (%) |
|--------------------|-------|-------|-------|-------|
| Theoretical values | 51.00 | 2.71  | 7.93  | 9.08  |
| Found values       | 50.74 | 2.49  | 7.58  | 9.16  |

EXAMPLE 147

5-[4-(1H-1-imidazolyl)-2-nitrophenylsulfanyl]isoquinoline

According to the method in Example 10, a mixture of 5-isoquinolinethiol 360 mg (2.2 mmol), DMF 9 ml, potassium carbonate 600 mg (4.3 mmol) and 1-(4-chloro-3-nitrophenyl)-1H-imidazole 420 mg (2.0 mmol) was stirred at 100° C. for 2.5 hours, and 5-[4-(1H-1-imidazolyl)-2-nitrophenylsulfanyl)isoquinoline 680 mg (97.6%) was obtained.

Melting point: 187–189° C.

Mass spectrometry (m/z): 349 (M+1)

Nuclear magnetic resonance spectrum (DMSO-$d_6$) δ: 9.47(1H,s), 8.56(1H,dd), 8.41(1H,d), 8.30(1H,s), 8.29(1H,d), 7.93(1H,d), 7.86(1H,dd), 7.79(1H,s), 7.72(1H,dd), 7.09 (1H,s), 6.58(1H,d).

Infrared absorption spectrum $v_{max}$ (KBr) cm$^{-1}$: 1620, 1520, 1340, 1320, 1250.

Element analysis values (calculated as $C_{18}H_{12}N_4O_2S$)

|  | C (%) | H (%) | N (%) | S (%) |
|---|---|---|---|---|
| Theoretical values | 62.06 | 3.47 | 16.08 | 9.20 |
| Found values | 61.87 | 3.52 | 16.36 | 8.84 |

EXAMPLE 148

5-[4-(1H-1-imidazolyl)-2-nitrophenylsulfonyl)isoquinoline

According to the method in Example 7(b), 5-[4-(1H-1-imidazolyl)-2-nitrophenylsulfonyl)isoquinoline 140 mg (66.0%) was obtained from 5-[4-(1H-1-imidazolyl)-2-nitrophenylsulfanyl)isoquinoline 200 mg (0.6 mmol), concentrated sulfuric acid 2 ml and OXONE (trademark) 700 mg (1.1 mmol).

Melting point: 243–245° C.

Mass spectrometry (m/z): 381 (M+1)

Nuclear magnetic resonance spectrum (DMSO-$d_6$) δ: 9.52(1H,s), 8.69(1H,d), 8.61(1H,d), 8.57(1H,d), 8.50–8.53 (3H,m), 8.30(1H,d), 8.24(1H,dd), 7.99(1H,d), 7.97(1H,dd), 7.16(1H,s).

Infrared absorption spectrum $v_{max}$ (KBr) cm$^{-1}$: 3100, 1610, 1550, 1160, 1130, 620.

Element analysis values (calculated as $C_{18}H_{12}N_4O_4S$)

|  | C (%) | H (%) | N (%) | S (%) |
|---|---|---|---|---|
| Theoretical values | 56.84 | 3.18 | 14.73 | 8.43 |
| Found values | 56.78 | 3.24 | 15.02 | 8.12 |

EXAMPLE 149

5-{[4-Phenylsulfonyl)phenyl]sulfanyl}isoquinoline

According to the method in Example 10, a mixture of 5-isoquinolinethiol 340 mg (2.0 mmol), DMF 10 ml, potassium carbonate 550 mg (4.3 mmol) and 1-chloro-(4-phenylsulfonyl)benzene 500 mg (2.0 mmol) was stirred at 140° C. for 3 hours, and 5-{[4-phenylsulfonyl)phenyl]sulfanyl}isoquinoline 710 mg (95.5%) was obtained.

Melting point: 189–191° C.

Mass spectrometry (m/z): 378 (M+1)

Nuclear magnetic resonance spectrum (DMSO-$d_6$) δ: 9.43(1H,s), 8.53(1H,d), 8.34(1H,d), 8.15(1H,d), 7.87–7.91 (3H,m), 7.77–7.86(3H,m), 7.65(1H,dd), 7.58(2H,dd), 7.15 (2H,d).

Infrared absorption spectrum $v_{max}$ (KBr) cm$^{-1}$: 1580, 1310, 1160, 1080, 820, 615, 565.

Element analysis values (calculated as $C_{12}H_{15}NO_2S_2$)

|  | C(%) | H(%) | S(%) |
|---|---|---|---|
| Theoretical values | 66.82 | 4.01 | 16.99 |
| Found values | 66.76 | 3.84 | 17.13 |

EXAMPLE 150

5-{[4-Phenylsulfonyl)phenyl]sulfonyl}isoquinoline

According to the method in Example 7(b), 5-{[4-phenylsulfonyl)phenyl]sulfonyl}isoquinoline 410 mg (75.9%) was obtained from 5-{[4-phenylsulfonyl)phenyl]sulfanyl}isoquinoline 500 mg (1.3 mmol), concentrated sulfuric acid 5 ml and OXONE (trademark) 1.63 g (2.7 mmol).

Melting point: 192–195° C.

Mass spectrometry (m/z): 410 (M+1)

Nuclear magnetic resonance spectrum (DMSO-$d_6$) δ: 9.46(1H,s), 8.72(1H,d), 8.63(1H,d), 8.55(1H,d), 8.24–8.27 (3H,m), 8.15(1H,d), 7.94–7.97(3H,m), 7.69(1H,dd), 7.60 (2H,dd).

Infrared absorption spectrum $v_{max}$ (KBr) cm$^{-1}$: 1320, 1160, 620, 580.

Element analysis values (calculated as $C_{21}H_{15}NO_4S_2 \cdot 1/16 H_2O$)

|  | C(%) | H(%) | S(%) |
|---|---|---|---|
| Theoretical values | 61.43 | 3.71 | 15.62 |
| Found values | 61.64 | 4.00 | 15.45 |

EXAMPLE 151

6-(5-Isoquinolylsulfanyl)-3-nitro-2-pyridylamine

According to the method in Example 10, a mixture of 5-isoquinolinethiol 300 mg (1.9 mmol), DMF 10 ml, potassium carbonate 520 mg (3.7 mmol) and 2-amino-6-chloro-3-nitropyridine 300 mg (1.9 mmol) was stirred at room temperature for 30 minutes, and 6-(5-isoquinolylsulfanyl)-3-nitro-2-pyridylamine 460 mg (86.7%) was obtained.

Melting point: 224–227° C.

Mass spectrometry (m/z): 299 (M+1)

Nuclear magnetic resonance spectrum (DMSO-$d_6$) δ: 9.45(1H,dd), 8.59(1H,dd), 8.38(1H,d), 8.24(1H,dd), 8.07 (1H,d), 7.99(1H,brs), 7.94(1H,d), 7.82(1H,dd), 5.84(1H,d).

Infrared absorption spectrum $v_{max}$ (KBr) cm$^{-1}$: 3470, 1620, 1560, 1340, 1250.

Element analysis values (calculated as $C_{14}H_{10}N_4O_2S \cdot 1/4 H_2O$)

|  | C(%) | H(%) | N(%) | S(%) |
|---|---|---|---|---|
| Theoretical values | 55.53 | 3.49 | 18.50 | 10.59 |
| Found values | 55.37 | 3.27 | 18.40 | 10.84 |

EXAMPLE 152

6-(5-Isoquinolylsulfonyl)-3-nitro-2-pyridylamine

According to the method in Example 7(b), 6-(5-isoquinolylsulfonyl)-3-nitro-2-pyridylamine 210 mg (66.0%) was obtained from 6-(5-isoquinolylsulfanyl)-3-nitro-2-pyridylamine 200 mg (0.7 mmol), concentrated sulfuric acid 2 ml and OXONE (trademark) 620 mg (1.0 mmol).

Melting point: 208–212° C.

Mass spectrometry (m/z): 331 (M+1)

Nuclear magnetic resonance spectrum (DMSO-$d_6$) δ: 9.68(1H,s), 8.76(1H,dd), 8.71(1H,d), 8.69(1H,d), 8.65(1H,d), 8.60(1H,d), 8.10(1H,brs), 8.06(1H,dd), 7.52(1H,dd).

Infrared absorption spectrum $v_{max}$ (KBr) cm$^{-1}$: 3450, 1630, 1340, 1260, 1120, 600.

Element analysis values (calculated as $C_{14}H_{10}N_4O_4S \cdot 2/3H_2SO_4$)

|  | C(%) | H(%) | N(%) | S(%) |
| --- | --- | --- | --- | --- |
| Theoretical values | 42.49 | 2.89 | 14.16 | 13.51 |
| Found values | 42.55 | 3.00 | 14.14 | 13.39 |

EXAMPLE 153

6-(5-Isoquinolylsulfanyl)-2,3-pyridinediamine

According to the method in Example 3, 6-(5-isoquinolylsulfanyl)-2,3-pyridinediamine 250 mg (97.7%) was obtained from 6-(5-isoquinolylsulfanyl)-3-nitro-2-pyridylamine 300 mg (1.0 mmol), concentrated hydrochloric acid 5 ml and stannous chloride dihydrate 800 mg (3.5 mmol).

Melting point: 198–199° C.

Mass spectrometry (m/z): 269 (M+1)

Nuclear magnetic resonance spectrum (DMSO-$d_6$) δ: 9.32(1H,d), 8.53(1H,d), 8.02(1H,d), 7.99(1H,d), 7.66(1H,d), 7.60(1H,dd), 6.63(1H,d), 6.34(1H,d), 5.68(2H,s), 4.88(2H,s).

Infrared absorption spectrum $v_{max}$ (KBr) cm$^{-1}$: 3420, 1620, 1460.

Element analysis values (calculated as $C_{14}H_{12}N_4S$)

|  | C(%) | H(%) | N(%) | S(%) |
| --- | --- | --- | --- | --- |
| Theoretical values | 62.66 | 4.51 | 20.88 | 11.95 |
| Found values | 62.83 | 4.72 | 20.72 | 12.02 |

EXAMPLE 154

5-(5-Isoquinolylsulfanyl)-2-methyl-1(3)H-imidazo[4,5-b]pyridine

According to the method in Example 91, 5-(5-isoquinolylsulfanyl)-2-methyl-1(3)H-imidazo[4,5-b]pyridine 150 mg (65.5%) was obtained from 6-(5-isoquinolylsulfanyl)-2,3-pyridinediamine 200 mg (0.8 mmol), acetic acid 0.3 ml and 6N hydrochloric acid 4.5 ml.

Melting point: 189–193° C.

Mass spectrometry (m/z): 293 (M+1)

Nuclear magnetic resonance spectrum (DMSO-$d_6$) δ: 9.39(1H,s), 8.51(1H,d), 8.26(1H,d), 8.10(1H,d), 7.97(1H,d), 7.76(1H,d), 7.72(1H,d), 6.86(1H,d).

Infrared absorption spectrum $v_{max}$ (KBr) cm$^{-1}$: 1620, 1400, 1260, 830.

Element analysis values (calculated as $C_{16}H_{12}N_4S \cdot 1/8H_2O$)

|  | C(%) | H(%) | N(%) | S(%) |
| --- | --- | --- | --- | --- |
| Theoretical values | 65.23 | 4.19 | 19.02 | 10.88 |
| Found values | 65.12 | 4.51 | 18.91 | 10.65 |

EXAMPLE 155

7-(5-Isoquinolylsulfanyl)-2-methyl-6-nitro-3,4-dihydro-4-quinazolinone

According to the method in Example 10, a mixture of 5-isoquinolinethiol 150 mg (0.9 mmol), DMF 5 ml, potassium carbonate 250 mg (1.8 mmol) and 7-chloro-2-methyl-6-nitro-3,4-dihydro-4-quinazolinone 200 mg (0.8 mmol) was stirred at room temperature for 2 hours, and 7-(5-isoquinolylsulfanyl)-2-methyl-6-nitro-3,4-dihydro-4-quinazolinone 260 mg (83.7%) was obtained.

Melting point: >270° C.

Mass spectrometry (m/z): 365 (M+1)

Nuclear magnetic resonance spectrum (DMSO-$d_6$) δ: 9.48(1H,s), 8.83(1H,s), 8.54(1H,d), 8.44(1H,d), 8.30(1H,d), 7.95(1H,d), 7.88(1H,dd), 6.37(1H,s), 2.18(3H,s).

Infrared absorption spectrum $v_{max}$ (KBr) cm$^{-1}$: 1700, 1600, 1360, 1340.

Element analysis values (calculated as $C_{18}H_{12}N_4O_3S \cdot 1/2H_2O$)

|  | C(%) | H(%) | N(%) | S(%) |
| --- | --- | --- | --- | --- |
| Theoretical values | 57.90 | 3.51 | 15.01 | 8.59 |
| Found values | 57.83 | 3.15 | 15.35 | 8.42 |

EXAMPLE 156

7-(5-Isoquinolylsulfonyl)-2-methyl-6-nitro-3,4-dihydro-4-quinazolinone

According to the method in Example 7(b), 7-(5-isoquinolylsulfonyl)-2-methyl-6-nitro-3,4-dihydro-4-quinazolinone 80 mg (58.2%) was obtained from 7-(5-isoquinolylsulfanyl)-2-methyl-6-nitro-3,4-dihydro-4-quinazolinone 120 mg (0.3 mmol), concentrated sulfuric acid 1.5 ml and OXONE (trademark) 400 mg (0.7 mmol).

Melting point: >270° C.

Nuclear magnetic resonance spectrum (DMSO-$d_6$) δ: 9.53(1H,s), 8.68(1H,d), 8.62(1H,d), 8.61(1H,s), 8.58(1H,d), 8.38(1H,s), 8.21(1H,d), 7.98(1H,dd), 2.42(3H,s).

Infrared absorption spectrum $v_{max}$ (KBr) cm$^{-1}$: 1690, 1610, 1540, 1360, 1340, 1130.

Element analysis values (calculated as $C_{18}H_{12}N_4O_5S \cdot 1/4H_2O$)

|  | C(%) | H(%) | N(%) | S(%) |
| --- | --- | --- | --- | --- |
| Theoretical values | 53.93 | 3.14 | 13.98 | 8.00 |
| Found values | 53.70 | 3.18 | 13.61 | 8.16 |

EXAMPLE 157

5-(5-Isoquinolylsulfanyl)-2-nitrobenzonitrile

According to the method in Example 10, a mixture of 5-isoquinolinethiol 1.20 g (7.4 mmol), DMF 40 ml, potassium carbonate 2.00 g (14.5 mmol) and 5-chloro-2-nitrobenzonitrile 1.30 g (7.1 mmol) was stirred at room temperature for 2 hours, and 5-(5-isoquinolylsulfanyl)-2-nitrobenzonitrile 2.14 g (97.8%) was obtained.

Melting point: 177–180° C.

Mass spectrometry (m/z): 308 (M+1)

Nuclear magnetic resonance spectrum (DMSO-$d_6$) δ: 9.47(1H,s), 8.58(1H,d), 8.41(1H,d), 8.26(1H,dd), 8.15(1H, d), 7.93(1H,d), 7.91(1H,d), 7.85(1H,dd), 7.20(1H,dd).

Infrared absorption spectrum $v_{max}$ (KBr) cm$^{-1}$: 2030, 1560, 1515, 1330.

Element analysis values (calculated as $C_{16}H_9N_3O_2S$)

|  | C(%) | H(%) | N(%) | S(%) |
| --- | --- | --- | --- | --- |
| Theoretical values | 62.53 | 2.95 | 13.67 | 10.43 |
| Found values | 62.36 | 2.94 | 13.75 | 10.47 |

EXAMPLE 158

2-Amino-5-(5-isoquinolylsulfanyl)benzonitrile

According to the method in Example 3, 2-amino-5-(5-isoquinolylsulfanyl)benzonitrile 220 mg (49.2%) was obtained from 5-(5-isoquinolylsulfanyl)-2-nitrobenzonitrile 500 mg (1.6 mmol), concentrated hydrochloric acid 15 ml and stannous chloride dihydrate 1.30 g (5.8 mmol).

Melting point: 197–201° C.

Mass spectrometry (m/z): 278 (M+1)

Nuclear magnetic resonance spectrum (DMSO-$d_6$) δ: 9.33(1H,d), 8.58(1H,d), 7.98–8.02(2H,m), 7.56–7.63(2H, m), 7.41(1H,d), 7.39(1H,d), 6.84(1H,d), 6.47(2H,s).

Infrared absorption spectrum $v_{max}$ (KBr) cm$^{-1}$: 3450, 2200, 1650, 1500, 1260.

Element analysis values (calculated as $C_{16}H_{11}N_3S$)

|  | C(%) | H(%) | N(%) | S(%) |
| --- | --- | --- | --- | --- |
| Theoretical values | 69.29 | 4.00 | 15.15 | 11.56 |
| Found values | 68.92 | 3.97 | 15.09 | 11.49 |

EXAMPLE 159

7-(5-Isoquinolylsulfanyl)-1,2,3,4-tetrahydro-9-acrydinylamine

A mixture of 2-amino-5-(5-isoquinolylsulfanyl) benzonitrile 150 mg (0.5 mmol), cyclohexanone 1 ml and zinc chloride 75 mg (0.5 mmol) was stirred overnight at 100° C. To the reaction mixture, 0.5 N sodium hydroxide was added, and the mixture was extracted with ethyl acetate. The organic layer was washed with water and saturated sodium chloride, dried over anhydrous sodium sulfate, and concentrated under reduced pressure. The resulting residue was crystallized from methanol-ether, and 7-(5-isoquinolylsulfanyl)-1,2,3,4-tetrahydro-9-acrydinylamine 58 mg (30.0%) was obtained.

Melting point: 248–254° C.

Mass spectrometry (m/z): 358 (M+1)

Nuclear magnetic resonance spectrum (DMSO-$d_6$) δ: 9.35(1H,d), 8.57(1H,d), 8.51(1H,d), 8.08(1H,d), 8.05(1H,d), 7.55–7.62(3H,m), 7.32(1H,dd), 6.47(2H,s), 2.80(2H,dd), 2.52(2H,dd), 1.79(4H,m).

Infrared absorption spectrum $v_{max}$ (KBr) cm$^{-1}$: 3460, 1650, 1560, 1480, 1370, 810.

Element analysis values (calculated as $C_{22}H_{19}N_3S \cdot 1/4H_2O$)

|  | C(%) | H(%) | S(%) |
| --- | --- | --- | --- |
| Theoretical values | 73.00 | 5.43 | 8.86 |
| Found values | 72.86 | 5.57 | 8.74 |

EXAMPLE 160

5-[(5-Nitro-2-pyridyl)-sulfanyl)isoquinoline

According to the method in Example 10, a mixture of 5-isoquinolinethiol 1.12 g (6.9 mmol), DMF 20 ml, potassium carbonate 1.92 g (13.9 mmol) and 2-chloro-5-nitropyridine 1.00 g (6.3 mmol) was stirred at 100° C. for 2 hours, and 5-[(5-nitro-2-pyridyl)-sulfanyl)isoquinoline 1.40 g (78.4%) was obtained.

Melting point: 115–117° C.

Mass spectrometry (m/z): 284 (M+1)

Nuclear magnetic resonance spectrum (DMSO-$d_6$) δ: 9.46(1H,s), 9.11(1H,d), 8.57(1H,d), 8.40(1H,d), 8.32(1H, dd), 8.26(1H,dd), 7.91(1H,d), 7.84(1H,dd), 7.05(1H,d).

Infrared absorption spectrum $v_{max}$ (KBr) cm$^{-1}$: 1590, 1570, 1510, 1350.

Element analysis values (calculated as $C_{14}H_9N_3O_2S$)

|  | C(%) | H(%) | N(%) | S(%) |
| --- | --- | --- | --- | --- |
| Theoretical values | 59.35 | 3.20 | 14.83 | 11.32 |
| Found values | 59.33 | 3.55 | 14.96 | 11.33 |

EXAMPLE 161

5-[(5-Nitro-2-pyridyl)-sulfonyl)isoquinoline

According to the method in Example 7(b), 5-[(5-nitro-2-pyridyl)sulfonyl)isoquinoline 50 mg (47.6%) was obtained from 5-[5-nitro-2-pyridyl)sulfanyl)isoquinoline 100 mg (0.4 mmol), concentrated sulfuric acid 1 ml and OXONE (trademark) 430 mg (0.7 mmol).

Melting point: 186–190° C.

Mass spectrometry (m/z): 316 (M+1)

Nuclear magnetic resonance spectrum (DMSO-$d_6$) δ: 9.49(1H,s), 9.34(1H,d), 8.89(1H,dd), 8.75(1H,dd), 8.66(1H, d), 8.65(1H,d), 8.61(1H,d), 8.30(1H,d), 7.99(1H,dd).

Infrared absorption spectrum $v_{max}$ (KBr) cm$^{-1}$: 1600, 1530, 1360, 1310, 1160, 1100.

Element analysis values (calculated as $C_{14}H_9N_3O_4S$)

|  | C(%) | H(%) | N(%) | S(%) |
| --- | --- | --- | --- | --- |
| Theoretical values | 53.33 | 2.88 | 13.33 | 10.17 |
| Found values | 53.25 | 3.05 | 13.21 | 9.79 |

EXAMPLE 162

N1-{4-chloro-2-(ethylcarboxamide)-5-[(8-nitro-6-isoquinolyl)sulfanyl]phenyl}propanamide The following reference shows synthesis of starting materials for producing the title compounds.

Reference example 1

4-Chloro-2-nitro-5-thiocyanatoaniline

A solution 8 ml of bromine 7.00 g in methanol was added dropwise to a suspension 8 ml of 4-chloro-2-nitroaniline 6.61 g (38.3 mmol) and ammonium thiocyanate 7.00 g (92.0 mmol) in methanol, and the mixture was stirred for 2 hours at room temperature. The reaction mixture was poured into ice water and alkalized with 4N sodium hydroxide, and the precipitated crystals were filtered. The crystals were washed with water and with ether and dried under reduced pressure, and 4-chloro-2-nitro-5-thiocyanatoaniline 7.88 g (89.6%) was obtained.

Nuclear magnetic resonance spectrum (DMSO-$d_6$) δ: 8.41(1H,s), 7.91(2H,s), 7.30(1H,s).

Reference example 2

4-Chloro-2-nitro-5-thiocyanato-1,2-benzenediamine

4-Chloro-2-nitro-5-thiocyanatoaniline 7.85 g (34.2 mmol) was suspended in concentrated hydrochloric acid 25 ml, stannous chloride dihydrate 53.2 g (236 mmol) was added, and the mixture was stirred at room temperature for 2.5 hours. 4N sodium hydroxide was added to alkalize, and the mixture was extracted with ethyl acetate. The organic layer was washed with saturated sodium chloride, dried over anhydrous magnesium sulfate and concentrated under reduced pressure. The resulting residue was purified by silica gel column chromatography, and 4-chloro-2-nitro-5-thiocyanato-1,2-benzenediamine 3.55 g (52.0%) was obtained.

Nuclear magnetic resonance spectrum (DMSO-$d_6$) δ: 6.83(1H,s), 6.67(1H,s), 5.35(2H,s), 4.96(2H,s).

Reference example 3

N1-[4-chloro-2-(ethylcarboxamide)-5-thiocyanatophenyl]propanamide

Anhydrous propionic acid was added to a solution of 4-chloro-2-nitro-5-thiocyanato-1,2-benzenediamine 2.73 g (13.7 mmol) in pyridine, and the mixture was stirred overnight at room temperature. The reaction mixture was poured into ice water, and the precipitates were collected and washed with water and with ether, N1-[4-chloro-2-(ethylcarboxamide)-5-thiocyanatophenyl]propaneamide 4.07 g (95.6%) was obtained.

Nuclear magnetic resonance spectrum (DMSO-$d_6$) δ: 9.46(2H,s), 8.06(1H,s), 8.01(1H,s), 2.37–2.42(2H,m), 1.07–1.10(6H,m).

Reference Example 4

N1-[4-chloro-2-(ethynlcarboxamide)-5-sulfanylphenyl]propanamide

Sodium borohydride 280 mg (6.6 mmol) was added to a DMF solution of N1-[4-chloro-2-(ethylcarboxamide)-5-thiocyanatophenyl]propaneamide 2.00 g (6.4 mmol), and the mixture was stirred for 1 hour at room temperature. The reaction mixture was poured into ice water, acidified with 1N hydrochloric acid, and extracted with ethyl acetate. The organic layer was washed with saturated sodium chlorid, dried over anhydrous magnesium sulfate and concentrated under reduced pressure, and N1-[4-chloro-2-(ethylcarboxamide)-5-sulfanylphenyl]propanamide 1.40 g (76.2%) was obtained.

Nuclear magnetic resonance spectrum (DMSO-$d_6$) δ: 9.24(1H,s), 9.22(1H,s), 7.73(1H,s), 7.66(1H,s), 5.77(1H,s), 2.33–2.36(4H,m), 1.05–1.09(6H,m).

According to the method in Example 10, a mixture of N1-[4-chloro-2-(ethylcarboxamide)-5-sulfanylphenyl] propanamide 500 mg (1.7 mmol), DMF 17 ml, potassium carbonate 480 mg (3.5 mmol) and 5-chloro-8-nitroisoquinoline 360 mg (1.7 mmol) was stirred at room temperature for 1 hour, and N1-{4-chloro-2-(ethylcarboxamide)-5-[(8-nitro-6-isoquinolyl)sulfanyl]phenyl}propaneamide 660 mg (83.2%) was obtained.

Melting point: 197–199° C.

Mass spectrometry (m/z): 459 (M+1)

Nuclear magnetic resonance spectrum (DMSO-$d_6$) δ: 9.89(1H,s), 9.47(1H,s), 9.44(1H,s), 8.81(1H,d), 8.37(1H,d), 8.21(1H,d), 8.11(1H,s), 7.90(1H,s), 7.27(1H,d), 2.42(4H,q), 1.10 (3H,t), 1.04(3H,t).

Infrared absorption spectrum $v_{max}$ (KBr) cm$^{-1}$: 1700, 1660, 1520, 1380.

Element analysis values (calculated as $C_{21}H_{19}ClN_4O_4S$)

|  | C(%) | H(%) | N(%) | S(%) |
|---|---|---|---|---|
| Theoretical values | 54.96 | 4.17 | 12.21 | 6.99 |
| Found values | 54.96 | 4.22 | 12.17 | 6.81 |

EXAMPLE 163

6(5)-Chloro-2-ethyl-5(6)-[(8-nitro-5-isoquinolyl)sulfanyl)]-1H-benzo[d]imidazole According to the method in Example 72, 6(5)-chloro-2-ethyl-5(6)-[(8-nitro-5-isoquinolyl)sulfanyl]-1H-benzo[d]imidazole 420 mg (78.2%) was obtained from N1-{4-chloro-2-(ethylcarboxamide)-5-[(8-nitro-6-isoquinolyl)sulfanyl]phenyl}propanamide 640 mg (1.4 mmol) and 6N hydrochloric acid 25 ml.

Melting point: 133–137° C.

Mass spectrometry (m/z): 385 (M+1)

Nuclear magnetic resonance spectrum (DMSO-$d_6$) δ: 9.89(1H,s), 8.80(1H,d), 8.27(1H,d), 8.23(1H,d), 7.92(1H,s), 7.87(1H,s), 7.01(1H,d), 2.87(2H,q), 1.32(3H,t).

Infrared absorption spectrum $v_{max}$ (KBr) cm$^{-1}$: 1520, 1320, 1270, 850.

Element analysis values (calculated as $C_{18}H_{13}ClN_4O_2S \cdot H_2O$)

|  | C(%) | H(%) | N(%) | S(%) |
|---|---|---|---|---|
| Theoretical values | 53.67 | 3.75 | 13.92 | 7.96 |
| Found values | 53.56 | 3.85 | 13.95 | 8.00 |

EXAMPLE 164

6(5)-Chloro-2-ethyl-5(6)-[(8-nitro-5-isoquinolyl)sulfonyl)]-1H-benzo[d]imidazole According to the method in Example 7(b), 6(5)-chloro-2-ethyl-5(6)-[(8-nitro-5-isoquinolyl)sulfonyl]-1H-benzo[d] imidazole 150 mg (67.4%) was obtained from 6(5)-chloro-2-ethyl-5(6)-[(8-nitro-5-isoquinolyl)sulfanyl)]-1H-benzo[d] imidazole 200 mg (0.5 mmol), concentrated sulfuric acid 2 ml and OXONE (trademark) 640 mg (1.0 mmol).

Mass spectrometry (m/z): 417 (M+1)

Nuclear magnetic resonance spectrum (DMSO-$d_6$) δ: 9.69(1H,s), 8.84(1H,d), 8.72(1H,d), 8.68(1H,s), 8.56(1H,d), 8.29(1H,d), 7.67(1H,s), 2.90(2H,q), 1.32(3H,t).

Infrared absorption spectrum $v_{max}$ (KBr) cm$^{-1}$: 1620, 1540, 1320, 1140, 820.

Element analysis values (calculated as $C_{18}H_{13}ClN_4O_4S.1/2H_2O$)

|  | C(%) | H(%) | N(%) | S(%) |
|---|---|---|---|---|
| Theoretical values | 50.77 | 3.31 | 13.13 | 7.53 |
| Found values | 50.73 | 3.45 | 12.99 | 7.25 |

EXAMPLE 165

2-Cyclopentyl-5(6)-(5-isoquinolylsulfanyl)-6(5)-nitro-1H-benzo[d]imidazole

According to the method in Example 91, 2-cyclopentyl-5(6)-(5-isoquinolylsulfanyl)-6(5)-nitro-1H-benzo[d]imidazole 410 mg (65.6%) was obtained from 4-(5-isoquinolylsulfanyl)-nitro-1,2-benzenediamine 500 mg (1.6 mmol), 6N hydrochloric acid 20 ml and cyclopentylcarboxylic acid 1.83 g (16.0 mmol).

Melting point: 234–238° C.

Mass spectrometry (m/z): 391 (M+1)

Nuclear magnetic resonance spectrum (DMSO-d$_6$) δ: 9.43(1H,s), 8.52(1H,d), 8.39(1H,s), 8.35(1H,d), 8.16(1H,d), 7.94(1H,d), 7.81(1H,dd), 3.22(1H,tt), 1.96–2.01(2H,m), 1.58–1.82(2H,m).

Infrared absorption spectrum $v_{max}$ (KBr) cm$^{-1}$: 1630, 1510, 1460, 1310, 830.

Element analysis values (calculated as $C_{21}H_{18}N_4O_2S.1/4H_2O$)

|  | C(%) | H(%) | N(%) | S(%) |
|---|---|---|---|---|
| Theoretical values | 63.86 | 4.72 | 14.19 | 8.12 |
| Found values | 63.93 | 4.70 | 14.09 | 8.35 |

EXAMPLE 166

6(5)-Chloro-2-cyclopentyl-5(6)-(5-isoquinolylsulfanyl)-1H-benzo[d]imidazole

According to the method in Example 91, 6(5)-chloro-2-cyclopentyl-5(6)(5-isoquinolylsulfanyl)-1H-benzo[d]imidazole 3.50 g (50.6%) was obtained as powder from 4-chloro-5-(5-isoquinolylsulfanyl)-1,2-benzenediamine 5.49 g (18.2 mmol), 6N hydrochloric acid 60 ml and cyclopentylcarboxylic acid 3.69 g (32.3 mmol).

Melting point: 228–230° C.

Mass spectrometry (m/z): 380 (M+1)

Nuclear magnetic resonance spectrum (DMSO-d$_6$) δ: 9.39(1H,s), 8.57(1H,d), 8.15(1H,d), 8.00(1H,d), 7.65–7.71(3H,m), 7.17(1H,s), 1.62–2.01(8H,m).

Infrared absorption spectrum $v_{max}$ (KBr) cm$^{-1}$: 1620, 1450, 830.

Element analysis values (calculated as $C_{21}H_{18}ClN_3S$)

|  | C(%) | H(%) | N(%) | S(%) |
|---|---|---|---|---|
| Theoretical values | 66.39 | 4.78 | 11.06 | 8.44 |
| Found values | 66.47 | 4.91 | 11.18 | 8.58 |

EXAMPLE 167

2-(Cyclopentylmethyl)-5(6)-(5-isoquinolylsulfonyl)-1H-benzo[d]imidazole

According to the method in Example 91, 2-(cyclopentylmethyl)-5(6)-(5-isoquinolylsulfonyl)-1H-benzo[d]imidazole 2.96 g (75.5%) was obtained from 5-(5-isoquinolylsulfonyl)-1,2-benzenediamine 3.00 g (10.0 mmol), cyclopentylacetic acid 5.0 ml (39.9 mmol) and 6N hydrochloric acid 50 ml.

Mass spectrometry (m/z): 392 (M+1)

Nuclear magnetic resonance spectrum (DMSO-d$_6$) δ: 9.43(1H,s), 8.67(1H,d), 8.63(1H,d), 8.47(1H,d), 8.43(1H,d), 8.16(1H,s), 7.92(1H,dd), 7.72(1H,dd), 7.61(1H,d), 2.80(2H,d), 2.29–2.35(1H,m), 1.45–1.69(6H,m), 1.19–1.23(2H,m).

Infrared absorption spectrum $v_{max}$ (KBr) cm$^{-1}$: 1620, 1310, 1130, 630.

Element analysis values (calculated as $C_{22}H_{21}N_3O_2S.1/4H_2O$)

|  | C(%) | H(%) | N(%) | S(%) |
|---|---|---|---|---|
| Theoretical values | 66.72 | 5.47 | 10.61 | 8.10 |
| Found values | 66.65 | 5.75 | 10.39 | 8.19 |

EXAMPLE 168

2-(Cyclopentylmethyl)-5(6)-(5-isoquinolylsulfonyl)-6(5)-nitro-1H-benzo[d]imidazole According to the method in Example 52(b), 2-(cyclopentylmethyl)-5(6)-(5-isoquinolylsulfonyl)-6(5)-nitro-1H-benzo[d]imidazole 520 mg (17.3%) was obtained from 2-(cyclopentylmethyl)-5(6)-(5-isoquinolylsulfonyl)-1H-benzo[d]imidazole 2.70 g (6.9 mmol), fuming nitric acid 2.5 ml and concentrated sulfuric acid 25 ml.

Mass spectrometry (m/z): 437 (M+1)

Nuclear magnetic resonance spectrum (DMSO-d$_6$) δ: 9.71(1H,s), 8.72(1H,d), 8.66(1H,d), 8.61(1H,s), 8.54(1H,dd), 8.31(1H,d), 8.01(1H,dd), 2.95(1H,d), 2.37–2.40(1H,m), 1.50–1.74(6H,m), 1.23–1.27(2H,m).

Infrared absorption spectrum $v_{max}$ (KBr) cm$^{-1}$: 1550, 1350, 1140.

EXAMPLE 169

6(5)-Chloro-2-ethyl-5(6)-[(8-amino-5-isoquinolyl)sulfonyl]-1H-benzo[d]imidazole

According to the method in Example 3, 6(5)-chloro-2-ethyl-5(6)-[(8-amino-5-isoquinolyl)sulfonyl]-1H-benzo[d]imidazole 55 mg (16.9%) was obtained from 6(5)-chloro-2-ethyl-5(6)-[(8-nitro-5-isoquinolyl)sulfonyl]-1H-benzo[d]imidazole 350 mg (0.8 mmol), concentrated hydrochloric acid 10 ml and stannous chloride dihydrate 1.02 g (4.5 mmol).

Mass spectrometry (m/z): 387 (M+1)

Nuclear magnetic resonance spectrum (DMSO-d$_6$) δ: 9.52(1H,s), 8.50(1H,s), 8.38(1H,d), 8.33(1H,d), 7.91(1H,d), 7.57(1H,s), 7.48(2H,s), 2.88(2H,q), 1.32(3H,t).

EXAMPLE 170

Suppressive effect on colchicine-induced neuronal cell death

To examine the possible effect on neuronal apoptosis, we estimated suppressive effect by using a model of colchicine-induced neuronal cell death (Nakagawa-Yagi, Biochemical and Biophysical Research Communications, Vol.199, pp807–817 (1994)) to study the effect for neuron apoptosis. Human neuroblastoma SH-SY5Y cells (3×10$^5$/60 mm culture dish) were respectively poured into Dulbecco's modified Eagle's medium containing 10% fetal calf serum, and retinoic acid (10 μM) was added the next day to cultivate for 5 days. Five days later, the medium was changed to Dulbecco's modified Eagle's medium containing 10% fetal calf serum and compounds of the present invention. After culturing for 30 min, colchicine (1 μM) was added and cultured for 3 days. Cell death was quantified by the release of LDH (lactate dehydrogenase) into the culture medium solution. The results were shown in FIG. 1. Date are expressed as a percent inhibition for the amount of LDH release induced by colchicine. By adding the compounds of the present invention, it was confirmed that neuronal cell death was remarkably inhibited.

EXAMPLE 171

Suppressive effect on 6-hydroxydopamine (6-OHDA)-inducing neuronal cell death

Data were obtained using 6-OHDA (200 μM) instead of colchicine in Example 170. The results were shown in FIGS. 2–4. Data are expressed as a percent inhibition for the amount of LDH release induced by 6-OHDA. By adding the compounds of the present invention, it was confirmed that neuronal cell death was remarkably inhibited.

In the following, the compound of the present invention in Examples are shown by formulas.

Example 1

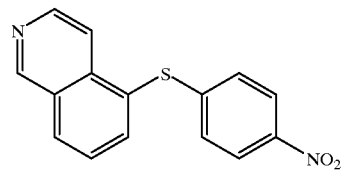

Example 2

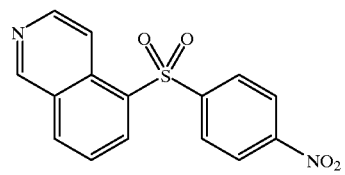

Example 3

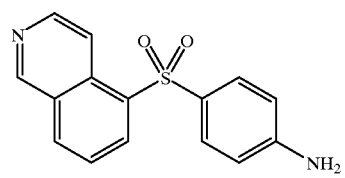

Example 4

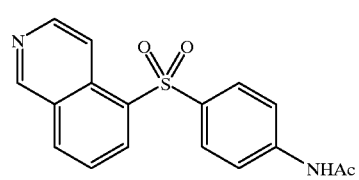

-continued

Example 5

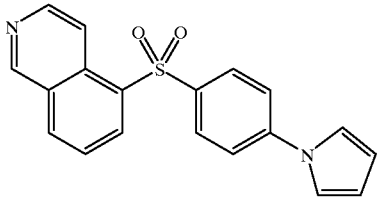

Example 6

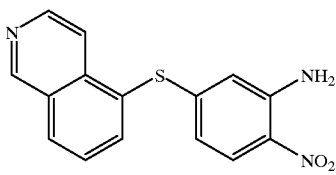

Example 7

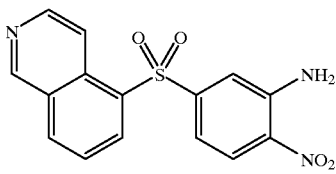

Example 8

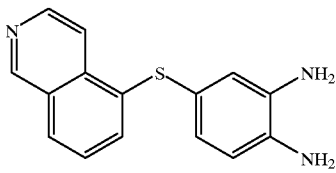

Example 9

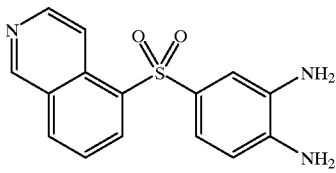

Example 10

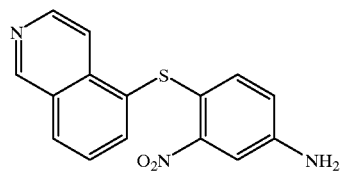

Example 11

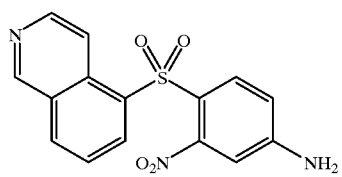

Example 12

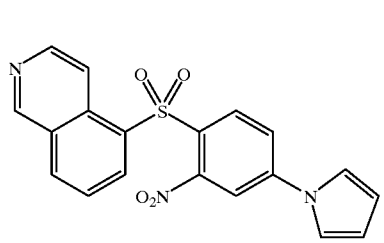

-continued

Example 13

Example 14

Example 15

Example 16

Example 17

Example 18

Example 19

-continued

Example 20

Example 21

Example 22

Example 23

Example 24

Example 25

Example 26

-continued
Example 27
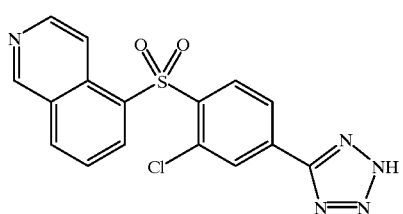
Example 28
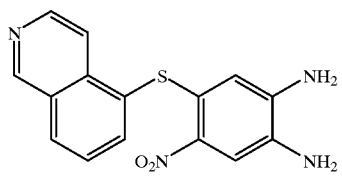
Example 29
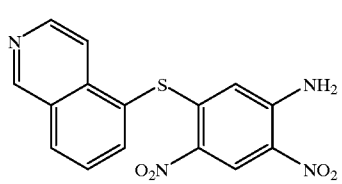
Example 30
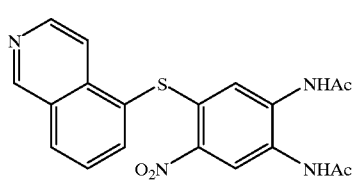
Example 31
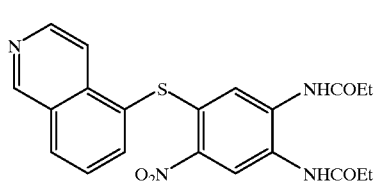
Example 32
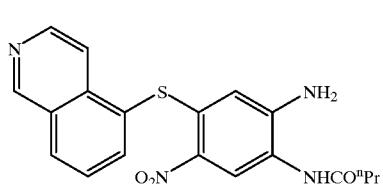
Example 33
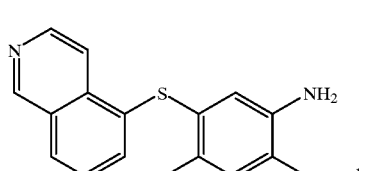
Example 34
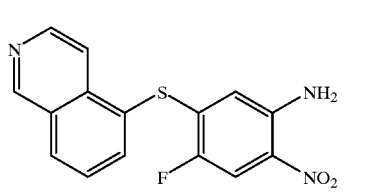
-continued
Example 35
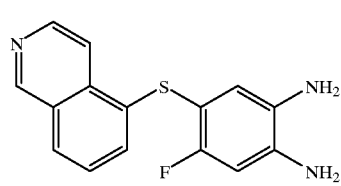
Example 36
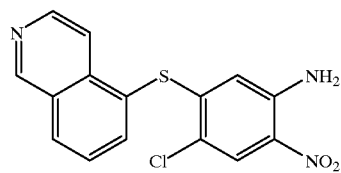
Example 37
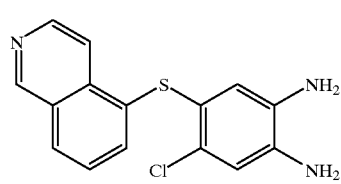
Example 38
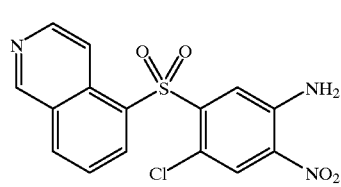
Example 39
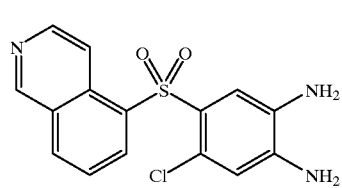
Example 40
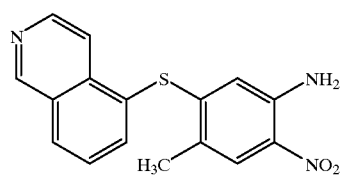
Example 41
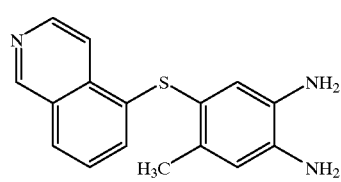
Example 42
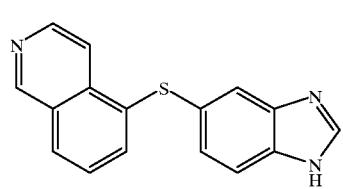

-continued

Example 43

Example 44

Example 45

Example 46

Example 47

Example 48

Example 49

Example 50

-continued

Example 51

Example 52

Example 52

Example 53

Example 54

Example 55

Example 56

-continued

Example 57

Example 58

Example 59

Example 60

Example 61

Example 62

Example 63

Example 64

-continued

Example 65

Example 66

Example 67

Example 68

Example 69

Example 70

Example 71

-continued

Example 72

Example 73

Example 73

Example 74

Example 75

Example 76

Example 77

Example 78

-continued

Example 78

Example 79

Example 80

Example 81

Example 82

Example 82

Example 83

-continued

Example 83

Example 84

Example 85

Example 86

Example 87

Example 88

Example 89

Example 90

-continued

Example 91

Example 92

Example 93

Example 94

Example 95

Example 96

Example 97

Example 98

Example 99
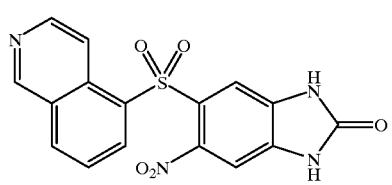
Example 100
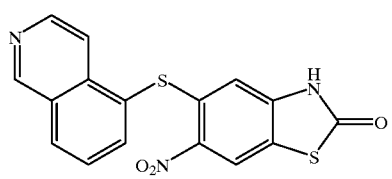
Example 101
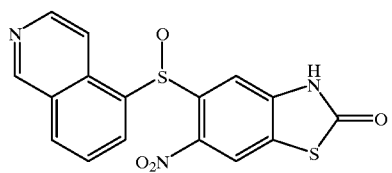
Example 102
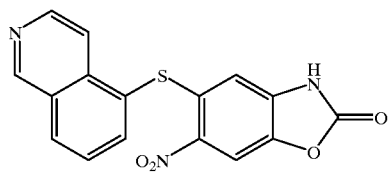
Example 103
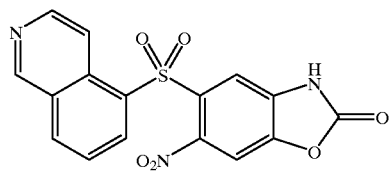
Example 104
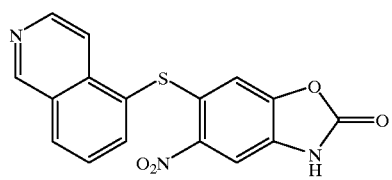
Example 105
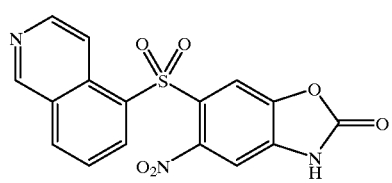
Example 106
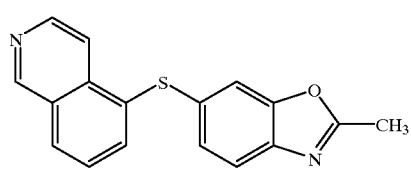
Example 107
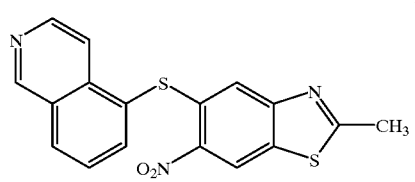
Example 108
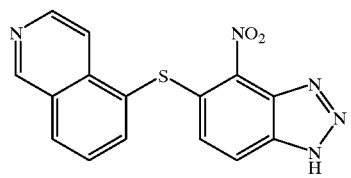
Example 109
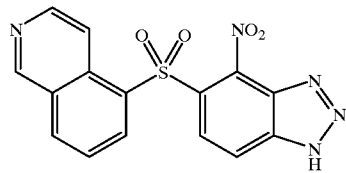
Example 110
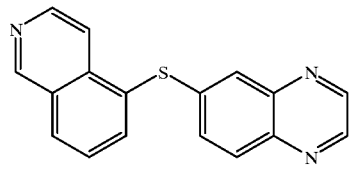
Example 111
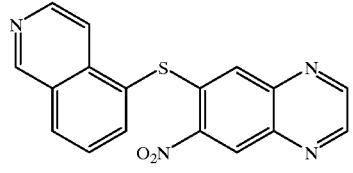
Example 112
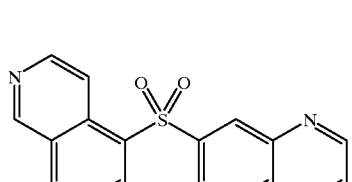
Example 113
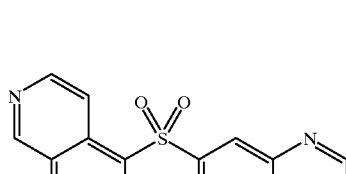
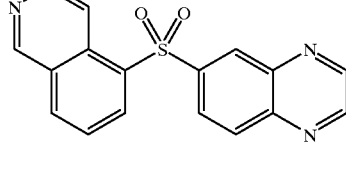

-continued

Example 114

Example 115

Example 116

Example 117

Example 118

Example 119

-continued

Example 120

Example 121

Example 122

Example 123

Example 123

Example 124

Example 124

107
-continued

Example 125

Example 126

Example 127

Example 128

Example 129

Example 130

Example 131

108
-continued

Example 132

Example 133

Example 134

Example 135

Example 136

Example 137

Example 138

Example 139
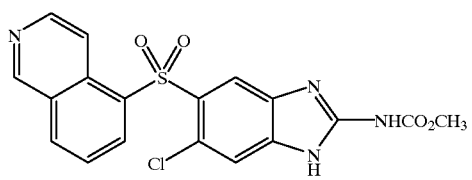
Example 140
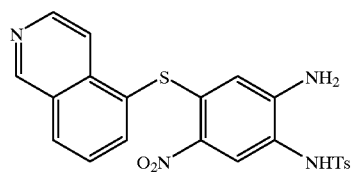
Example 141
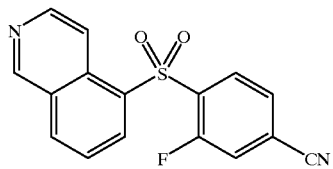
Example 142
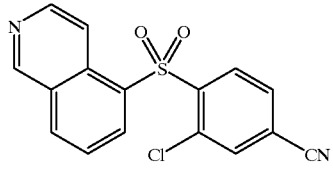
Example 143
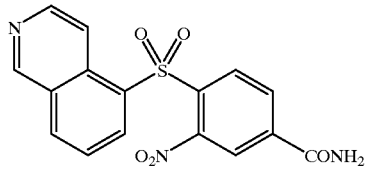
Example 144
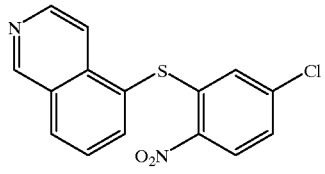
Example 145
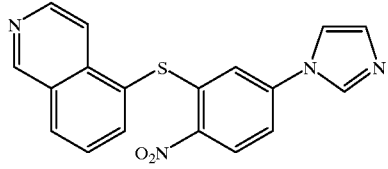
Example 146
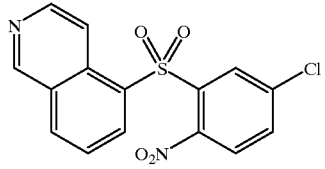
Example 147
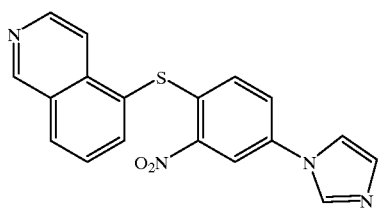
Example 148
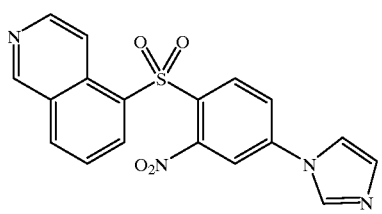
Example 149
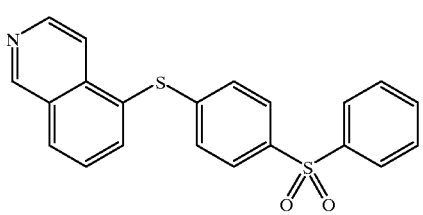
Example 150
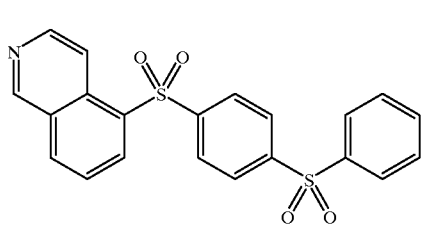
Example 151
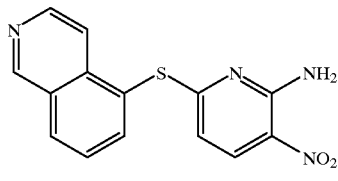
Example 152
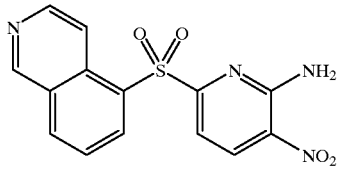
Example 153
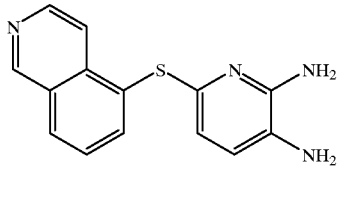

-continued

Example 154

Example 155

Example 156

Example 157

Example 158

Example 159

Example 160

Example 161

Example 162

Example 163

Example 164

Example 165

Example 166

Example 167

-continued

Example 168

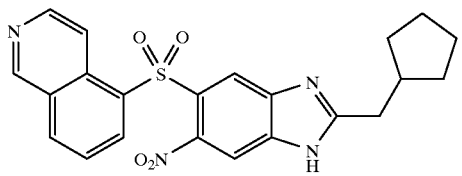

Example 169

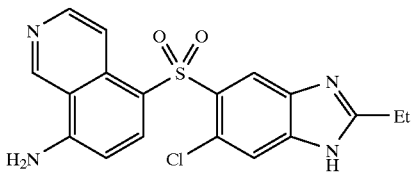

Industrial Applicability

As shown in the above results, new isoquinoline derivatives and their pharmaceutically acceptable acid addition salts can be provided by the present invention. The new isoquinoline derivatives and their pharmaceutically acceptable acid addition salts of the present invention have inhibitory activity on neuronal cell death (apoptotic cell death-type) caused by excessive apoptosis in a nervous system and they are useful for prevention or treatment of neurodegenerative disorders such as Alzheimer's disease, Parkinson's disease, Huntington's chorea and amyotrophic lateral sclerosis, cerebral ischemic injury such as stroke, and peripheral neutropathy in diabetes mellitus.

We claim:

1. A compound of formula I

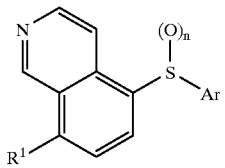

wherein Ar is an aromatic ring or a heterocycle which may be substituted, n is 0, 1 or 2, and $R^1$ is hydrogen, nitro or amino, and wherein S is bonded directly to a carbon atom of Ar;

or a pharmaceutically acceptable salt of said compound.

2. A compound according to claim 1, wherein Ar is

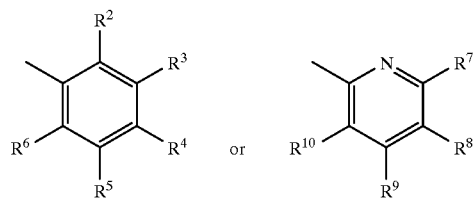

wherein $R^2$–$R^{10}$ are the same or different substituted groups selected from the group consisting of hydrogen, nitro, amino, lower alkyl amide, phenyl amide, lower alkyl amino, phenyl amino, phenyl lower alkyl amino, carbamoyl, hydroxy, cyano, lower alkyl substituted by halogen, phenyl sulfonyl, phenyl sulfonamide, imidazole, tetrazole, pyrrole, and halogen.

3. A compound according to claim 1, wherein Ar is selected from the group consisting of

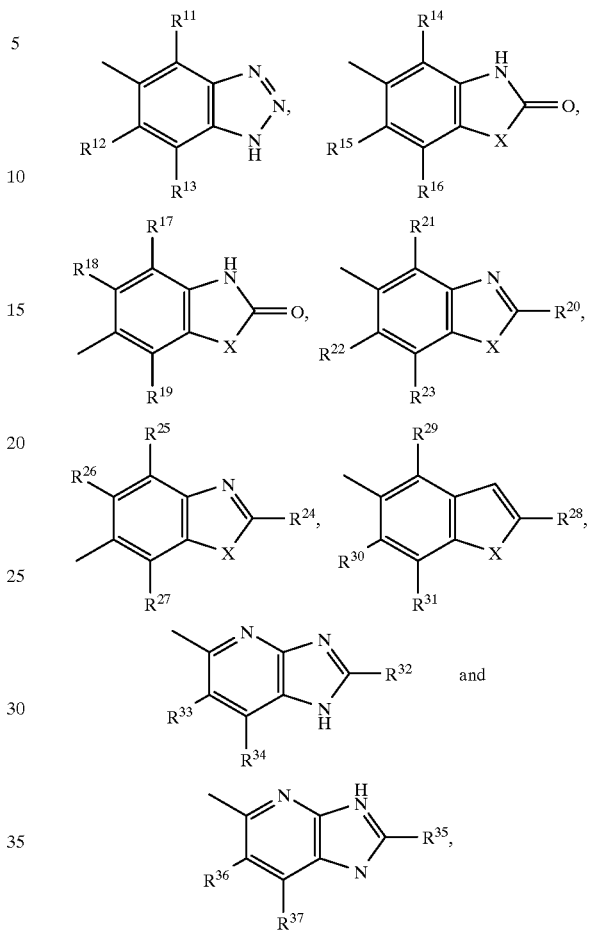

wherein X is NH, O or S, $R^{11}$–$R^{37}$ are the same or different substituted groups selected from the group consisting of hydrogen, lower alkyl, lower alkyl substituted by halogen, aryl, aralkyl, nitro, amino, cyano and halogen.

4. A compound according to claim 1, wherein Ar is

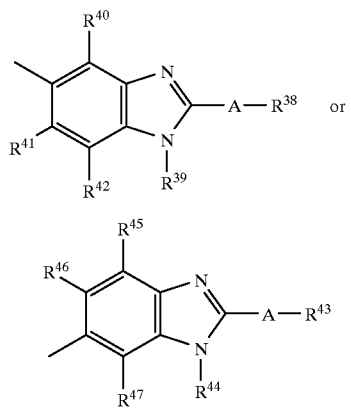

wherein $R^{38}$–$R^{47}$ are the same or different subtituted groups selected from the group of hydrogen, lower alkyl, cycloalkyl, lower alkyl substituted by halogen, aryl, aralkyl, nitro, —$NR^{48}R^{49}$, —$NHCO_2R^{50}$, hydroxy, cyano and halogen, A is a substituted group selected from a single bond or lower alkylene, and $R^{48}$–$R^{50}$ are the same or different substituted groups selected from hydrogen and lower alkyl.

5. A compound according to claim 1 wherein Ar is substituted by

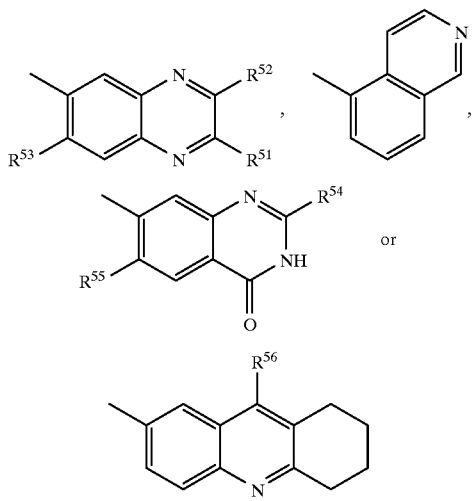

wherein $R^{51}$–$R^{56}$ are the same or different substituted groups selected from the group consisting of hydrogen, lower alkyl, lower alkyl substituted by halogen, aryl, aralkyl, nitro, amino, cyano and halogen atom; or $R^{51}$ and $R^{52}$ are joined to form a single ring or a polycyclic ring.

6. A compound according to claim 1 wherein said sulfur atom is directly bonded to a carbon atom of an aromatic ring of said Ar.

7. A compound according to claim 1 wherein n is 0 or 1.

8. A compound according to claim 1, selected from the group consisting of 4-(5-isoquinolylsulfonyl)aniline; 4-(5-isoquinolylsulfonyl)-3-nitroaniline; 5-[2-nitro-4-(pyrrol-1-yl)phenylsulfonyl]isoquinoline; 5(6)-(5-isoquinolylsulfanyl)-2-methyl-1H-benzo[d]imidazole; 5(6)-(5-isoquinolylsulfonyl)-2-methyl-6(5)-nitro-1H-benzo[d]imidazole; 6(5)-chloro-5(6)-(5-isoquinolylsulfonyl)-2-methyl-1H-benzo[d]imidazole; 5(6)-(5-isoquinolylsulfonyl)-2-methyl-1H-benzo[d]imidazole-6(5)-carbonitrile; 2-ethyl-5(6)-(5-isoquinolylsulfonyl)-6(5)-nitro-1H-benzo[d]imidazole; 6(5)-chloro-2-ethyl-5(6)-(5-isoquinolylsulfonyl)-1H-benzo[d]imidazole; 5(6)-(5-isoquinolylsulfonyl)-6(5)-nitro-2-propyl-1H-benzo[d]imidazole; 5(6)-(5-isoquinolylsulfonyl)-7(4)-nitro-2-propyl-1H-benzo[d]imidazole; 6(5)-chloro-5(6)-(5-isoquinolylsulfonyl)-2-propyl-1H-benzo[d]imidazole; 2-isopropyl-5(6)-(5-isoquinolylsulfonyl)-1H-benzo[d]imidazole; 2-isopropyl-5(6)-(5-isoquinolylsulfonyl)-6(5)-nitro-1H-benzo[d]imidazole; 2-cyclopropyl-5(6)-(5-isoquinolylsulfanyl)-1H-benzo[d]imidazole; 2-cyclobutyl-5(6)-(5-isoquinolylsulfonyl)-1H-benzo[d]imidazole; 2-cyclopentyl-5(6)-(5-isoquinolylsulfonyl)-1H-benzo[d]imidazole; 2-cyclohexyl-5(6)-(5-isoquinolylsulfonyl)-1H-benzo[d]imidazole; 2-cycloheptyl-5(6)-(5-isoquinolylsulfonyl)-1H-benzo[d]imidazole; 5-(5-isoquinolylsulfonyl)-6-nitro-2,3-dihydro-1H-benzo[d]imidazole-2-one; 5(6)-(5-isoquinolylsulfanyl)-4(7)-nitro-1H-benzo[d][1,2,3]triazole; 2,3-diphenyl-6-(5-isoquinolylsulfonyl)quinoxaline; 2-cyclohexyl-5(6)-(5-isoquinolylsulfonyl)-6(5)-nitro-1H-benzo[d]imidazole; 2-cyclopentyl-5(6)-(5-isoquinolylsulfonyl)-6(5)-nitro-1H-benzo[d]imidazole; 6(5)-chloro-2-cyclohexyl-5(6)-(5-isoquinolylsulfonyl)-1H-benzo[d]imidazole; 6(5)-chloro-2-cyclopentyl-5(6)-(5-isoquinolylsulfonyl)-1H-benzo[d]imidazole; 6(5)-chloro-2-cyclobutyl-5(6)-(5-isoquinolylsulfonyl)-1H-benzo[d]imidazole; 6(5)-bromo-5(6)-(5-isoquinolylsulfonyl)-2-methyl-1H-benzo[d]imidazole; 6(5)-bromo-2-ethyl-5(6)-(5-isoquinolylsulfonyl)-1H-benzo[d]imidazole; and 6(5)-bromo-2-cyclohexyl-5(6)-(5-isoquinolylsulfonyl)-1H-benzo[d]imidazole; or a pharmaceutically acceptable acid addition salt thereof.

9. A compound according to claim 1, selected from the group consisting of 5(6)-(5-isoquinolylsulfonyl)-2-methyl-6(5)-nitro-1H-benzo[d]imidazole; 5(6)-(5-isoquinolylsulfonyl)-2-methyl-1H-benzo[d]imidazole-6(5)-carbonitrile; 2-ethyl-5(6)-(5-isoquinolylsulfonyl)-6(5)-nitro-1H-benzo[d]imidazole; 6(5)-chloro-2-ethyl-5(6)-(5-isoquinolylsulfonyl)-1H-benzo[d]imidazole; 2-cyclobutyl-5(6)-(5 -isoquinolylsulfonyl)-1H-benzo[d]imidazole; 2-cyclopentyl-5(6)-(5-isoquinolylsulfonyl)-1H-benzo[d]imidazole; 2-cyclohexyl-5(6)-(5-isoquinolylsulfonyl)-1H-benzo[d]imidazole; 2-cycloheptyl-5(6)-(5-isoquinolylsulfonyl)-1H-benzo[d]imidazole; 2-cyclohexyl-5(6)-(5-isoquinolylsulfonyl)-6(5)-nitro-1H-benzo[d]imidazole; 2-cyclopentyl-5(6)-(5-isoquinolylsulfonyl)-6(5)-nitro-1H-benzo[d]imidazole; 6(5)-chloro-2-cyclohexyl-5(6)-(5-isoquinolylsulfonyl)-1H-benzo[d]imidazole; 6(5)-chloro-2-cyclopentyl-5(6)-(5-isoquinolylsulfonyl)-1H-benzo[d]imidazole; 6(5)-chloro-2-cyclobutyl-5(6)-(5-isoquinolylsulfonyl)-1H-benzo[d]imidazole; 6(5)-bromo-5(6)-(5-isoquinolylsulfonyl)-2methyl-1H-benzo[d]imidazole; 6(5)-bromo-2-ethyl-5(6)-(5-isoquinolylsulfonyl)-1H-benzo[d]imidazole; and 6(5)-bromo-2-cyclohexyl-5(6)-(5-isoquinolylsulfonyl)-1H-benzo[d]imidazole; or a pharmaceutically acceptable acid addition salt thereof.

* * * * *